(12) United States Patent
Hamasaki et al.

(10) Patent No.: US 8,981,108 B2
(45) Date of Patent: Mar. 17, 2015

(54) OPTICAL FILM, RETARDATION PLATE, ELLIPTICA POLARIZING PLATE, LIQUID CRYSTAL DISPLAY DEVICE AND COMPOUND

(71) Applicant: FUJIFILM Corporation, Minato-ku (JP)

(72) Inventors: Ryo Hamasaki, Ashigarakami-gun (JP); Hideyuki Nishikawa, Ahigarakami-gun (JP); Makoto Takahashi, Ashigarakami-gun (JP); Takashi Miyahara, Ashigarakami-gun (JP); Masuji Motoki, Ashigarakami-gun (JP); Masaaki Tsukase, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 13/954,119

(22) Filed: Jul. 30, 2013

(65) Prior Publication Data

US 2013/0317229 A1 Nov. 28, 2013

Related U.S. Application Data

(62) Division of application No. 12/726,640, filed on Mar. 18, 2010, now Pat. No. 8,524,334.

(30) Foreign Application Priority Data

Mar. 19, 2009 (JP) ................................. 2009-068293
Mar. 17, 2010 (JP) ................................. 2010-060267

(51) Int. Cl.
*C09K 19/34* (2006.01)
*C07D 413/14* (2006.01)
*G02B 5/30* (2006.01)
*C09K 19/04* (2006.01)

(52) U.S. Cl.
CPC ............ *C09K 19/348* (2013.01); *C07D 413/14* (2013.01); *C09K 19/3475* (2013.01); *G02B 5/3033* (2013.01); *G02B 5/3083* (2013.01); *C09K 2019/0429* (2013.01)
USPC .................... 548/131; 252/299.01; 252/299.6

(58) Field of Classification Search
CPC .. C07D 413/14; C07D 417/00; C07D 417/10; C09K 19/348; C09K 19/375; C09K 2019/0429; G02B 5/3083; G02B 5/32
USPC .............. 428/1.1, 1.3, 1.6; 548/131; 349/117, 349/118, 75, 121; 252/299.01, 299.6
See application file for complete search history.

(56) References Cited

U.S. PATENT DOCUMENTS

| 5,583,679 | A | 12/1996 | Ito et al. |
| 7,696,353 | B2 | 4/2010 | Takahashi et al. |
| 8,304,554 | B2 | 11/2012 | Takahashi et al. |

(Continued)

FOREIGN PATENT DOCUMENTS

| CN | 1010689796 A | 11/2007 |
| EP | 1506991 A2 | 2/2005 |
| JP | 8-050206 A | 2/1996 |

(Continued)

OTHER PUBLICATIONS

Office Action issued in corresponding Japanese Patent Application No. 2010-060267 dated Dec. 24, 2013 with English excerpt.
Office Action issued in corresponding Chinese Patent Application No. 201010143104.X dated Jan. 30, 2014 with English translation.
Office Action issued on Mar. 19, 2014, by the Taiwan Patent Office in corresponding Taiwanese Patent Application No. 099108166 and an English translation of the Office Action. (10 pages).
Office Action issued in corresponding Chinese Patent Application No. 201010143104.X dated May 20, 2013.

*Primary Examiner* — Gwendolyn Blackwell
*Assistant Examiner* — Ruiyun Zhang
(74) *Attorney, Agent, or Firm* — Buchanan, Ingersoll & Rooney PC

(57) ABSTRACT

An optical film including at least one compound represented by formula (1) is disclosed. In the formula, $Y^{11}$, $Y^{12}$ and $Y^{13}$ each independently represent methine or a nitrogen atom; $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C). In the formulae, $L^{12}$, $L^{22}$, and $L^{32}$ each represent a 5-membered heterocyclic group.

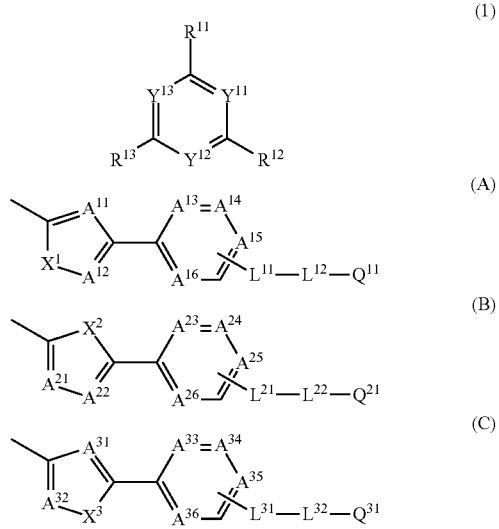

4 Claims, No Drawings

(56) References Cited

U.S. PATENT DOCUMENTS

| | | |
|---|---|---|
| 2005/0208387 A1 | 9/2005 | Minabe et al. |
| 2008/0064879 A1 | 3/2008 | Takahashi et al. |
| 2009/0068378 A1* | 3/2009 | Takahashi .................. 428/1.1 |
| 2009/0233009 A1 | 9/2009 | Tanaka et al. |
| 2010/0222594 A1 | 9/2010 | Takahashi et al. |

FOREIGN PATENT DOCUMENTS

| | | |
|---|---|---|
| JP | 2005225819 A * | 8/2005 |
| JP | 2006-522826 A | 10/2006 |
| JP | 2007-002220 A | 1/2007 |
| JP | 2007-204705 A | 8/2007 |
| WO | WO 2004/091502 A2 | 10/2004 |

* cited by examiner

OPTICAL FILM, RETARDATION PLATE, ELLIPTICA POLARIZING PLATE, LIQUID CRYSTAL DISPLAY DEVICE AND COMPOUND

CROSS-REFERENCE TO RELATED APPLICATIONS

The present application is a Divisional Application of U.S. application Ser. No. 12/726,640, filed Mar. 18, 2010, which claims benefit of priority under 35 U.S.C. 119 to Japanese Patent Application Nos. 2009-068293, filed on Mar. 19, 2009, and 2010-060267, filed on Mar. 17, 2010, which are expressly incorporated herein by reference in its entirety.

BACKGROUND OF THE INVENTION

1. Technical Field

The present invention relates to an optical film useful for liquid crystal display devices or the like, and to a retardation plate, elliptical polarizing plate and liquid crystal display device having the same. The present invention relates also to compounds which are useful for producing optical films.

2. Background Art

It is known that discotic liquid crystal compounds are important as a material for optical compensation sheets. Examples of a liquid crystal compound exhibiting a discotic liquid crystallinity include 2,3,6,7,10,11-hexa{4-(4-acryloyloxyhexyloxy)benzoyloxy}triphenylene (for example, JPA No. 8-50206).

Usually, retardation, Δnd, of an optical compensation film may be determined depending on the optical properties of a liquid crystal cell to be compensated by the film. Retardation of an optically anisotropic layer, Δnd, is a product of birefringence, Δn, of the layer and the thickness, d, of the layer. Even if the layer is thin, the layer, having large birefringence, Δn, would be able to compensate birefringence of a liquid crystal cell. On the other hand, the layer having small birefringence, Δn, wouldn't be able to compensate birefringence of a liquid crystal cell unless the layer is thick. Forming a thick layer containing aligned liquid crystal molecules suffers from more defects in the alignment compared with forming a thin layer containing aligned liquid crystal molecules. Therefore, compound having higher Δn may be more useful for producing optically anisotropic layers or the like.

In JPA No. 2007-2220, compounds having high Δn are disclosed.

In JPA No. 2007-204705, liquid crystal compounds, having a skeleton similar to that of the compounds disclosed in JPA No. 2007-2220 and two side chains, are disclosed.

SUMMARY OF THE INVENTION

When any optical element such as an optical compensation sheet is produced by using a discotic liquid crystal compound, not only the temperature at which the compound starts to exhibit a liquid crystal phase such as a discotic-nematic phase is important, but also the temperature range in which the compound continues to exhibit the liquid crystal phase is important. A compound having a higher temperature at which it starts to exhibit a liquid crystal phase and a wider temperature range in which it continues to exhibit the liquid crystal phase are preferable since the latitude for producing optical films such as optical compensation sheets can be widened.

One object of the present invention is to provide an optical film, useful for optical compensation of liquid crystal display devices, which can be produced stably with a large latitude, and a retardation plate, elliptical polarizing plate and liquid crystal display device employing the film.

Another object of the present invention is to provide a novel compound useful for producing optical elements such as retardation plates.

Another object of the present invention is to provide a liquid crystal compound having a high temperature at which it starts to exhibit a liquid crystal phase and a wide temperature range in which it continues to exhibit the liquid crystal phase, and a novel intermediate.

The means for achieving the above-mentioned objects are as follows.

[1] An optical film comprising at least one compound represented by formula (1):

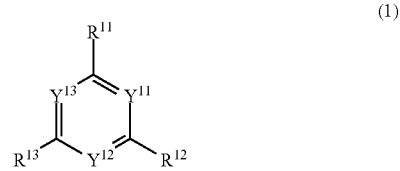

(1)

where $Y^{11}$, $Y^{12}$ and $Y^{13}$ each independently represent methine or a nitrogen atom; $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C):

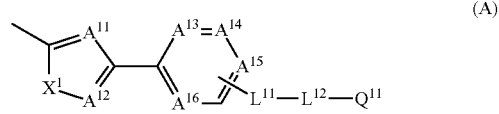

(A)

where $A^{11}$ and $A^{12}$ each independently represent a nitrogen atom or methine; $A^{13}$, $A^{14}$, $A^{15}$ and $A^{16}$ each independently represent a nitrogen atom or methine, provided that any hydrogen atom(s) in methine may be replaced with a group, -$L^{11}$-$L^{12}$-$Q^{11}$; $X^1$ represents an oxygen atom, a sulfur atom, methylene or imino; $L^{11}$ represents a 5-membered heterocyclic group; $L^{12}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{11}$ represents a polymerizable group, a hydrogen atom, OH, COOH or a halogen atom;

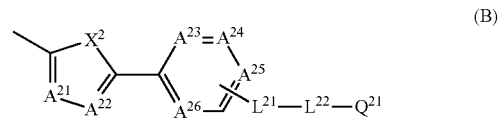

(B)

where $A^{21}$ and $A^{22}$ each independently represent a nitrogen atom or methine; $A^{23}$, $A^{24}$, $A^{25}$ and $A^{26}$ each independently represent a nitrogen atom or methine, provided that any hydrogen atom(s) in methine may be replaced with a group, $-L^{21}-L^{22}-Q^{21}$; $X^2$ represents an oxygen atom, a sulfur atom, methylene or imino; $L^{21}$ represents a 5-membered heterocyclic group; $L^{22}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{21}$ represents a polymerizable group, a hydrogen atom, OH, COOH or a halogen atom;

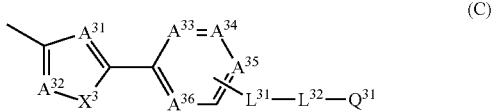

(C)

where $A^{31}$ and $A^{32}$ each independently represent a nitrogen atom or methine; $A^{33}$, $A^{34}$, $A^{35}$ and $A^{36}$ each independently represent a nitrogen atom or methine, provided that any hydrogen atom(s) in methine may be replaced with a group, $-L^{31}-L^{32}-Q^{31}$; $X^3$ represents an oxygen atom, a sulfur atom, methylene or imino; $L^{31}$ represents a 5-membered heterocyclic group; $L^{32}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{31}$ represents a polymerizable group, a hydrogen atom, OH, COOH or a halogen atom.

[2] The optical film of [1], wherein $L^{11}$, $L^{21}$ and $L^{31}$ in the formula each independently represent a 5-membered heterocyclic group denoted by any one of the following formulae:

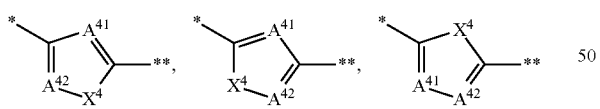

where "*" indicates a site binding to the 6-membered ring; "**" indicates a site binding to $L^{12}$, $L^{22}$ or $L^{32}$; $A^{41}$ and $A^{42}$ each independently represent methine or a nitrogen atom; and $X^4$ represents an oxygen atom, a sulfur atom, methylene or imino.

[3] The optical film of [1] or [2], wherein $A^{11}$, $A^{12}$, $A^{21}$, $A^{22}$, $A^{31}$ and $A^{32}$ in the formulae represent a nitrogen atom.

[4] The optical film of any one of [1]-[3], wherein $X^1$, $X^2$ and $X^3$ in the formulae represent an oxygen atom.

[5] The optical film of any one of [1]-[4], wherein $A^{13}$, $A^{14}$, $A^{15}$, $A^{16}$, $A^{23}$, $A^{24}$, $A^{25}$, $A^{26}$, $A^{33}$, $A^{34}$, $A^{35}$ and $A^{36}$ in the formulae represent methine in which any hydrogen atom(s) may be replaced with a group, $-L^{11}-L^{12}-Q^{11}$, $-L^{21}-L^{22}-Q^{21}$, or $-L^{31}-L^{32}-Q^{31}$.

[6] The optical film of any one of [1]-[5], wherein $R^{11}$, $R^{12}$ and $R^{13}$ in the formula each represent a group denoted by formula (A) or (C).

[7] The optical film of claim any one of [1]-[6], wherein $Q^{11}$, $Q^{21}$ and $Q^{31}$ in the formulae represent a polymerizable group shown below:

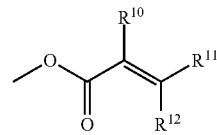

where $R^{10}$, $R^{11}$ and $R^{12}$ each independently represent a hydrogen atom or an alkyl.

[8] The optical film of any one of [1]-[7], wherein $Y^{11}$, $Y^{21}$ and $Y^{31}$ in the formula represent methine.

[9] A retardation plate comprising a transparent support and at least one optically anisotropic layer thereon, wherein the at least one optically anisotropic layer is an optical film as set forth in any one of [1]-[8].

[10] An elliptical polarizing plate comprising a retardation plate as set forth in [9] and a polarizing film.

[11] A liquid crystal display device comprising a retardation plate as set forth in [9].

[12] A liquid crystal display device comprising an elliptical polarizing plate as set forth in [11].

[13] A compound represented by formula (1a):

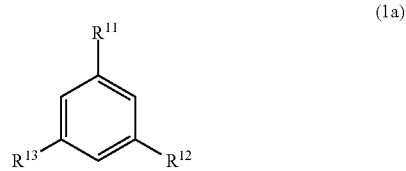

(1a)

where $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C):

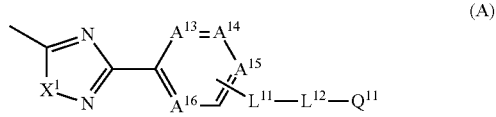

(A)

Where $A^{13}$, $A^{14}$, $A^{15}$ and $A^{16}$ each independently represent methine, provided that any hydrogen atom(s) in methine may be replaced with a group, $-L^{11}-L^{12}-Q^{11}$; $X^1$ represents an oxygen atom, a sulfur atom, methylene or imino; $L^{11}$ represents a 5-membered heterocyclic group; $L^{12}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{11}$ represents a polymerizable group, a hydrogen atom, OH, COOH or a halogen atom;

(B)
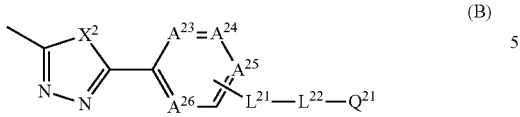

where $A^{23}$, $A^{24}$, $A^{25}$ and $A^{26}$ each independently represent methine, provided that any hydrogen atom(s) in methine may be replaced with a group, $-L^{21}-L^{22}-Q^{21}$; $X^2$ represents an oxygen atom, a sulfur atom, methylene or imino; $L^{21}$ represents a 5-membered heterocyclic group; $L^{22}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —SO$_2$—, —NR—, —NRSO$_2$— and —SO$_2$NR— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{21}$ represents a polymerizable group, a hydrogen atom, OH, COOH or a halogen atom;

(C)
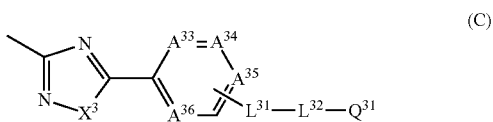

where $A^{33}$, $A^{34}$, $A^{35}$ and $A^{36}$ each independently represent a nitrogen atom or methine, provided that any hydrogen atom(s) in methine may be replaced with a group, $-L^{31}-L^{32}-Q^{31}$; $X^3$ represents an oxygen atom, a sulfur atom, methylene or imino; $L^{31}$ represents a 5-membered heterocyclic group; $L^{32}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —SO$_2$—, —NR—, —NRSO$_2$— and —SO$_2$NR— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{31}$ represents a polymerizable group, a hydrogen atom, OH, COOH or a halogen atom.

[14] A compound represented by formula (1b):

(1b)
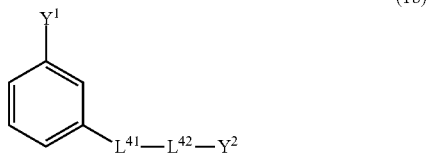

where $L^{41}$ represents formula (D), (E) or (F)

(D)
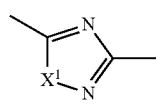

(E)
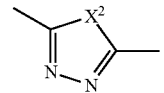

(F)
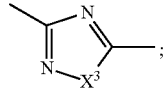

$X^1$, $X^2$ and $X^3$ each independently represent an oxygen atom, a sulfur atom, methylene or imino; $Y^1$ represents CN, COOH or amidoxime; $Y^2$ represents —COOH, —OH, $C_{1-4}$ alkyl, a halogen atom or a hydrogen atom; $L^{42}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —SO$_2$—, —NR—, —NRSO$_2$— and —SO$_2$NR— where R represents a hydrogen atom or a $C_{1-4}$ alkyl, or provided that one hydrogen atom or two or more hydrogen atoms in the alkylene or the alkenylene may be replaced with one halogen atom or two or more halogen atoms.

According to the present invention, it is possible to provide an optical film, useful for optical compensation of liquid crystal display devices, which can be produced stably with a large latitude, and a retardation plate, elliptical polarizing plate and liquid crystal display device employing the film.

According to the present invention, it is possible also to provide a novel compound useful for producing optical elements such as retardation plates.

According to the present invention, it is possible also to provide a liquid crystal compound having a high temperature at which it starts to exhibit a liquid crystal phase and a wide temperature range in which it continues to exhibit the liquid crystal phase, and a novel intermediate.

DETAILED DESCRIPTION OF THE INVENTION

The invention is described in detail hereinunder. Note that, in this patent specification, any numerical expressions in a style of "numerical value 1 to numerical value 2" will be used to indicate a range including the lower and upper limits represented by the numeral values 1 and 2 given before and after "to", respectively.

1. Optical Film
1.-(1) Compound of Formula (1)

The present invention relates to an optical film containing at least one compound represented by formula (1).

(1)
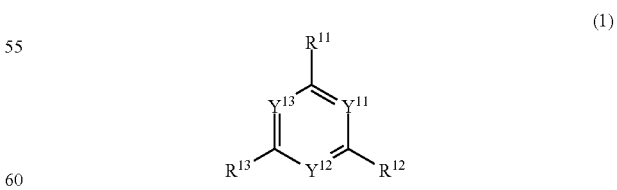

where $Y^{11}$, $Y^{12}$ and $Y^{13}$ each independently represent methine or a nitrogen atom. In the embodiments wherein $Y^{11}$, $Y^{12}$ and $Y^{13}$ represent methine, any hydrogen atom(s) in methine may be replaced with any substituent. Examples of the substituent which methine may have include alkyls, alkoxys, aryloxys, acyls alkoxycarbonyls, acyloxys, acylaminos, alkoxycarbonylaminos, alkylthios, arylthios, halogen atoms and cyano. Among these substituents, alkyls, alkoxys, alkoxycarbonyls, acyloxys, halogen atoms and cyano are more preferable; and $C_{1-12}$ alkyls, $C_{1-12}$ alkoxys, $C_{2-12}$ alkoxycarbonyls, $C_{2-12}$ acyloxys, halogen atoms and cyano are even more preferable.

In terms of ease or cost in its synthesis, the compounds in which all of $Y^{11}$, $Y^{12}$ and $Y^{13}$ are methine are preferable; and the compounds in which all of $Y^{11}$, $Y^{12}$ and $Y^{13}$ are non-substituted methine are more preferable. That is, preferable examples of the compound represented by formula (1) include those represented by formula (1a) in which $Y^{11}$, $Y^{12}$ and $Y^{13}$ are non-substituted methine.

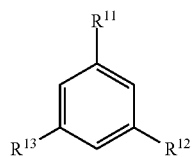

(1a)

In formulae (1) and (1a), $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C). In terms of its synthesis or its optical properties, formulae (A) and (C) are preferable; and formula (A) is more preferable. The compounds satisfying the condition of $R^{11}$=$R^{12}$=$R^{13}$ are also preferable.

And the compounds in which all of $R^{11}$, $R^{12}$ and $R^{13}$ represent formula (A), (B) or (C) are preferable since they tend to have a wider temperature range in which they continue to exhibit a liquid crystal phase.

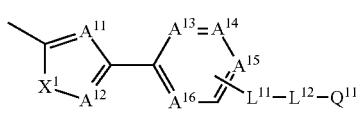

(A)

In formula (A), $A^{11}$ and $A^{12}$ each independently represent a nitrogen atom or methine; $A^{13}$, $A^{14}$, $A^{15}$ and $A^{16}$ each independently represent a nitrogen atom or methine, provided that any hydrogen atom(s) in methine may be replaced with a group, -$L^{11}$-$L^{12}$-$Q^{11}$.

Preferably at least one of $A^{11}$ and $A^{12}$ is a nitrogen atom, and more preferably, both of $A^{11}$ and $A^{12}$ are nitrogen atoms.

Preferably, at least three of $A^{13}$, $A^{14}$, $A^{15}$, and $A^{16}$ are methine, and more preferably, all of $A^{13}$, $A^{14}$, $A^{15}$, and $A^{16}$ are methine. Any hydrogen atom(s) in methine may be replaced with a group, -$L^{11}$-$L^{12}$-$Q^{11}$. In terms of high Δn, preferably, all of $A^{13}$, $A^{14}$, $A^{15}$, and $A^{16}$ are non-substituted methine (that is, a group, -L binds to the m-position of the 6-membered ring), or $A^{13}$, $A^{14}$, and $A^{16}$ are non-substituted methine and $A^{15}$ is a carbon atom binding to a group -$L^{11}$-$L^{12}$-$Q^{11}$ (that is, a group, -$L^{11}$-$L^{12}$-$Q^{11}$, binds to the p-position of the 6-membered ring); and in terms of wavelength-dispersion of Δn, all of $A^{13}$, $A^{14}$, $A^{15}$, and $A^{16}$ are non-substituted methine (that is, a group, -$L^{11}$-$L^{12}$-$Q^{11}$, binds to the m-position of the 6-membered ring).

When $A^{11}$-$A^{16}$ each independently represent methine, any hydrogen atom(s) in methine may be replaced with substituent(s) other than the group -$L^{11}$-$L^{12}$-$Q^{11}$. Examples of the substituent include halogen atoms such as a fluorine atom, chlorine atom, bromine atom and iodine atom; cyano, nitro, $C_{1-16}$ alkyls, $C_{2-16}$ alkenyls, $C_{2-16}$ alkynyls, $C_{1-16}$ halogenated alkyls, $C_{1-16}$ alkoxyls, $C_{2-16}$ acyls, $C_{1-16}$ alkylthios, $C_{2-16}$ acyloxys, $C_{2-16}$ alkoxycarbonyls, carbamoyl, $C_{2-16}$ alky substituted carbamoyls, and $C_{2-16}$ acylaminos. Among these, halogen atoms, cyano, $C_{1-16}$ alkyls and $C_{1-16}$ halogenated alkyls are preferable; halogen atoms, $C_{1-4}$ alkyls and $C_{1-4}$ halogenated alkyls are more preferable; and halogen atoms, $C_{1-3}$ alkyls and trifluoromethyl are even more preferable.

In formula (A), $X^1$ represents an oxygen atom, a sulfur atom, methylene or imino, and preferably, represents an oxygen atom.

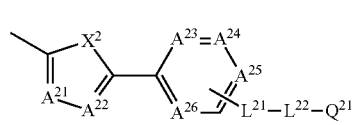

(B)

In formula (B), $A^{21}$ and $A^{22}$ each independently represent a nitrogen atom or methine; $A^{23}$, $A^{24}$, $A^{25}$ and $A^{26}$ each independently represent a nitrogen atom or methine, provided that any hydrogen atom(s) in methine may be replaced with a group, -$L^{21}$-$L^{22}$-$Q^{21}$.

Preferably at least one of $A^{21}$ and $A^{22}$ is a nitrogen atom, and more preferably, both of $A^{21}$ and $A^{22}$ are nitrogen atoms.

Preferably, at least three of $A^{23}$, $A^{24}$, $A^{25}$, and $A^{26}$ are methine, and more preferably, all of $A^{23}$, $A^{24}$, $A^{25}$, and $A^{26}$ are methine. Any hydrogen atom(s) in methine may be replaced with a group, -$L^{21}$-$L^{22}$-$Q^{21}$. In terms of high Δn, preferably, all of $A^{23}$, $A^{24}$, $A^{25}$, and $A^{26}$ are non-substituted methine (that is, a group, -$L^{21}$-$L^{22}$-$Q^{21}$, binds to the m-position of the 6-membered ring), or $A^{23}$, $A^{24}$, and $A^{26}$ are non-substituted methine and $A^{25}$ is a carbon atom binding to a group -$L^{21}$-$L^{22}$-$Q^{21}$ (that is, a group, -$L^{21}$-$L^{22}$-$Q^{21}$, binds to the p-position of the 6-membered ring); and in terms of wavelength-dispersion of Δn, all of $A^{23}$, $A^{24}$, $A^{25}$, and $A^{26}$ are non-substituted methine (that is, a group, -$L^{21}$-$L^{22}$-$Q^{21}$, binds to the m-position of the 6-membered ring).

When $A^{21}$-$A^{26}$ each independently represent methine, any hydrogen atom(s) in methine may be replaced with substituent(s) other than the group -$L^{21}$-$L^{22}$-$Q^{21}$. Examples of the substituent include those exemplified as a substituent of $A^{11}$-$A^{16}$ above.

In formula (B), $X^2$ represents an oxygen atom, a sulfur atom, methylene or imino, and preferably, represents an oxygen atom.

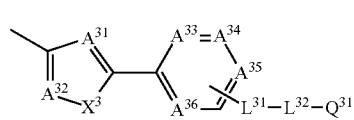

(C)

In formula (C), $A^{31}$ and $A^{32}$ each independently represent a nitrogen atom or methine; $A^{33}$, $A^{34}$, $A^{35}$ and $A^{36}$ each independently represent a nitrogen atom or methine, provided that any hydrogen atom(s) in methine may be replaced with a group, -$L^{31}$-$L^{32}$-$Q^{31}$.

Preferably at least one of $A^{31}$ and $A^{32}$ is a nitrogen atom, and more preferably, both of $A^{31}$ and $A^{32}$ are nitrogen atoms.

Preferably, at least three of $A^{33}$, $A^{34}$, $A^{35}$, and $A^{36}$ are methine, and more preferably, all of $A^{33}$, $A^{34}$, $A^{35}$, and $A^{36}$ are methine. Any hydrogen atom(s) in methine may be replaced with a group, -$L^{31}$-$L^{32}$-$Q^{31}$. In terms of high Δn, preferably, all of $A^{33}$, $A^{34}$, $A^{35}$, and $A^{36}$ are non-substituted methine (that is, a group, -$L^{31}$-$L^{32}$-$Q^{31}$, binds to the m-position of the 6-membered ring), or $A^{33}$, $A^{34}$, and $A^{36}$ are non-substituted methine and $A^{35}$ is a carbon atom binding to a group -$L^{31}$-$L^{32}$-$Q^{31}$, (that is, a group, -$L^{31}$-$L^{32}$-$Q^{31}$, binds to the p-position of the 6-membered ring); and in terms of wavelength-dispersion of $\Delta n$, all of $A^{33}$, $A^{34}$, $A^{35}$, and $A^{36}$ are non-substituted methine (that is, a group, -$L^{31}$-$L^{32}$-$Q^{31}$, binds to the m-position of the 6-membered ring).

When $A^{31}$-$A^{36}$ each independently represent methine, any hydrogen atom(s) in methine may be replaced with substituent(s) other than the group -$L^{31}$-$L^{32}$-$Q^{31}$ Examples of the substituent include those exemplified as a substituent of $A^{31}$-$A^{36}$ above.

In formula (C), $X^3$ represents an oxygen atom, a sulfur atom, methylene or imino, and preferably, represents an oxygen atom.

$L^{11}$ in formula (A), $L^{21}$ in formula (B) and $L^{31}$ in formula (C) each independently represent a 5-membered heterocyclic group. The 5-membered heterocyclic group is a 5-membered cyclic group in which at least one hetero atom such as a nitrogen atom, an oxygen atom and sulfur atom is embedded, and may be an aromatic or non-aromatic group. The groups shown below are preferable.

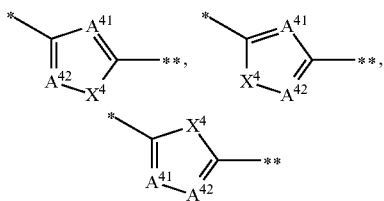

In the formulae, "*" indicates a site binding to the 6-membered ring; "**" indicates a site binding to $L^{12}$, $L^{22}$ or $L^{32}$; $A^{41}$ and $A^{42}$ each independently represent a nitrogen atom or methine; and $X^4$ represents an oxygen atom, a sulfur atom, methylene or imino.

Preferably, at least of $A^{41}$ and $A^{42}$ represents a nitrogen atom; and more preferably, both of $A^{41}$ and $A^{42}$ represent a nitrogen atom. Preferably, $X^4$ represents an oxygen atom.

Examples of $L^{11}$, $L^{21}$, and $L^{31}$ include those shown below.

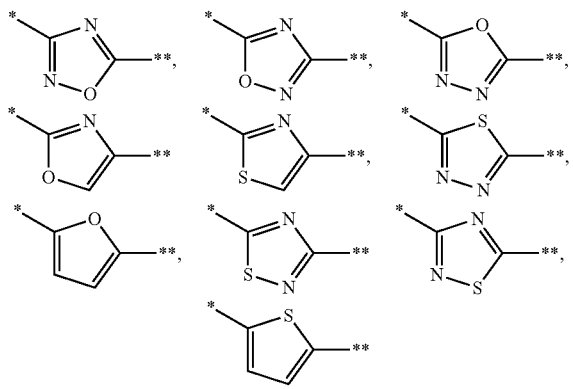

$L^{12}$ in formula (A), $L^{22}$ in formula (B) and $L^{32}$ in formula (C) each independently represent an alkylene or alkenylene, provided that one $CH_2$ or two or more $CH_2$ not adjacent to each other in the alkylene or alkenylene may be independently replaced with —O—, —COO—, —OCO—, —OCOO—, —CO—, —S—, —SO$_2$—, —NR—, —NRSO$_2$— or —SO$_2$NR— where R represents a hydrogen atom or a $C_{1-4}$ alkyl, or provided that one hydrogen atom or two or more hydrogen atoms in the alkylene or the alkenylene may be replaced with a halogen atom.

The alkylene group is preferably a $C_{1-20}$, more preferably $C_{1-16}$, and even more preferably $C_{1-12}$ alkylene group. The alkenylene group is preferably a $C_{2-20}$, more preferably $C_{2-16}$, and even more preferably $C_{2-12}$ alkenylene group One $CH_2$ or two or more $CH_2$ not adjacent to each other in the alkylene or alkenylene may be independently replaced with at least one selected from the divalent group consisting of —O—, —COO—, —OCO—, —OCOO—, —CO—, —S—, —SO$_2$—, —NR—, —NRSO$_2$— and —SO$_2$NR— where R represents a hydrogen atom or a $C_{1-4}$ alkyl. Two or more $CH_2$ may be replaced with two or more selected from the divalent group. Examples of the alkylene group include —$(CH_2)_m$-L-$(CH_2)_n$—. In the group, —$(CH_2)_m$-L-$(CH_2)_n$—, m and n represents a number of equal to or more than 1. The sum of m and n is preferably equal to or smaller than 20, more preferably equal to or smaller than 16, and even more preferably equal to or smaller than 12; and the sum is preferably equal to or greater than 2, and more preferably equal to or greater than 4. In the group, —$(CH_2)_m$-L-$(CH_2)_n$—, L represents one selected from the above-mentioned divalent group.

And, one hydrogen atom or two or more hydrogen atoms in the alkylene or the alkenylene may be replaced with one or two or more halogen atoms such as fluorine, chlorine, bromine and iodine atoms.

$Q^{11}$ in formula (A), $Q^{21}$ in formula (B) and $Q^{31}$ in formula (C) each independently represent a polymerizable group, a hydrogen atom, OH, COOH or a halogen atom such as a fluorine atom, a chlorine atom, a bromine atom and a bromine atom. For avoiding changing the properties of the optical film of the invention depending on the variation of the environment such as a temperature, preferably, $Q^{11}$, $Q^{21}$ and $Q^{31}$ each represent a polymerizable group. However, even when the compound represented by formula (1) having no polymerizable group is used, the alignment of the compound of formula (1) may be fixed by carrying out polymerization of other polymerizable compound to be used with the compound of formula (1). Preferably, polymerization is carried out according to an addition polymerization (including ring-opening polymerization) manner or a condensation polymerization manner. That is, preferably, the polymerizable group is selected from the group capable of carrying out addition polymerization or condensation polymerization. Examples of the polymerizable group are shown below.

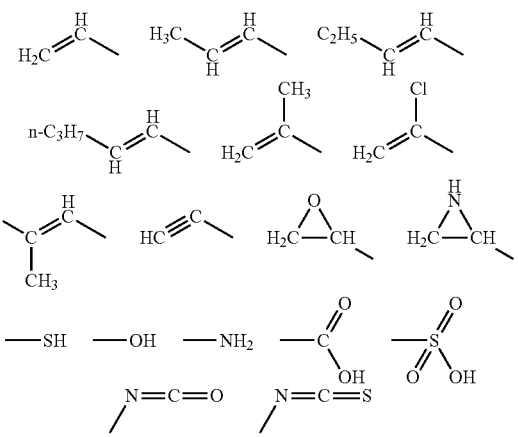

More preferably, the polymerizable group is selected from the group capable of carrying out addition polymerization.

Examples of such a polymerizable group include a polymerizable ethylenic unsaturated group and a ring-opening polymerizable group.

Examples of the group capable of carrying out addition polymerization include the group shown below.

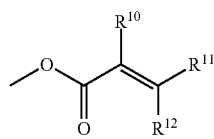

In the formula, $R^{10}$, $R^{11}$ and $R^{12}$ each independently represent a hydrogen atom or an alkyl. The alkyl group is preferably a $C_{1-5}$ alkyl, and more preferably $C_1$ alkyl, methyl. Examples of the group represented by formula include the acrylate group represented by formula (M-1) and the methacrylate group represented by formula (M-2).

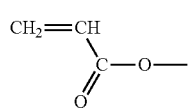

(M-1)

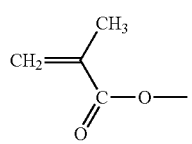

(M-2)

Other examples of the group capable of carrying out addition polymerization include the group shown below.

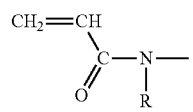

(M-3)

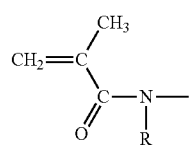

(M-4)

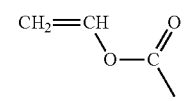

(M-5)

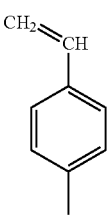

(M-6)

In formulae (M-3) and (M-4), R represents a hydrogen atom or an alkyl, and preferably represents a hydrogen atom or methyl.

Among formulae (M-1)-(M-6), formulae (M-1) and (M-2) are preferable, and formula (M-1) is more preferable.

Examples of the ring-opening polymerizable group include a cyclic ether group; and among these an epoxy group and oxethanyl group are more preferable, and an epoxy group is even more preferable.

Examples of the compound represented by formula (1) include, however are not limited to, those shown below.

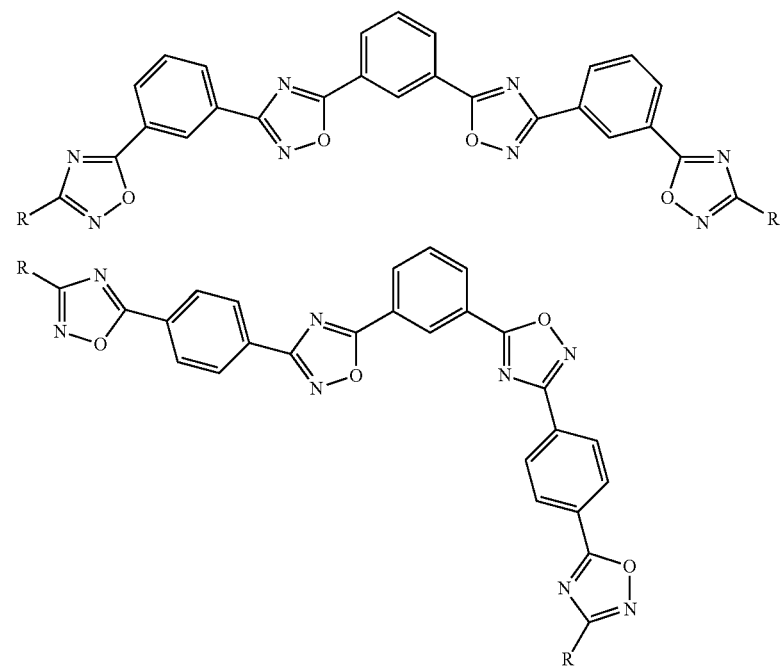

-continued
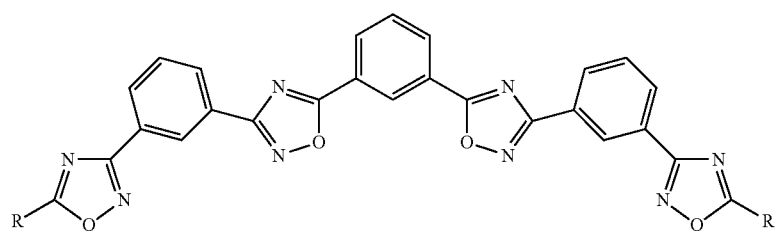
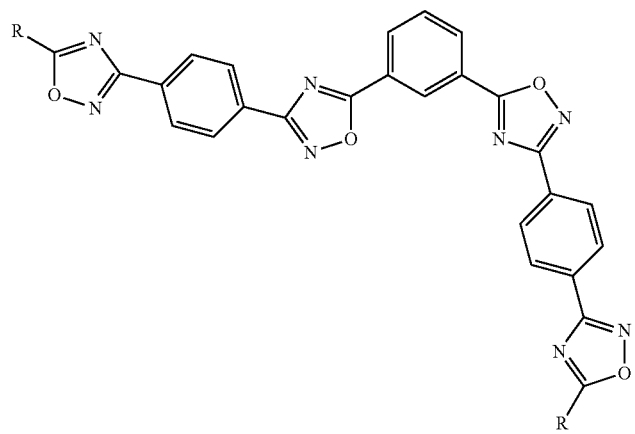
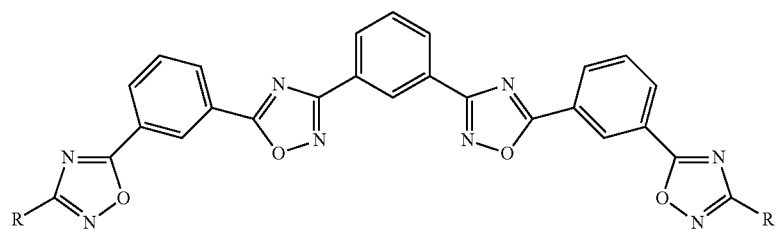
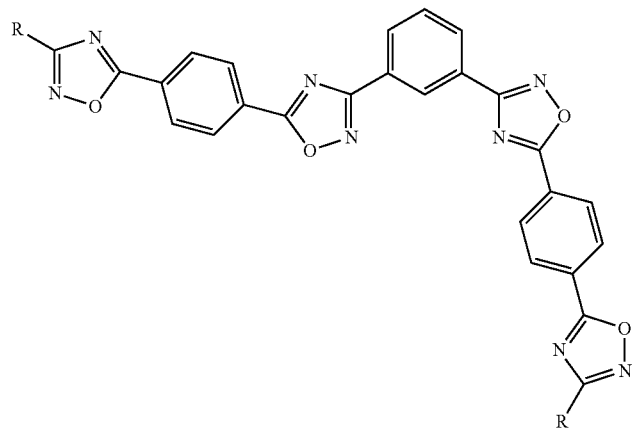
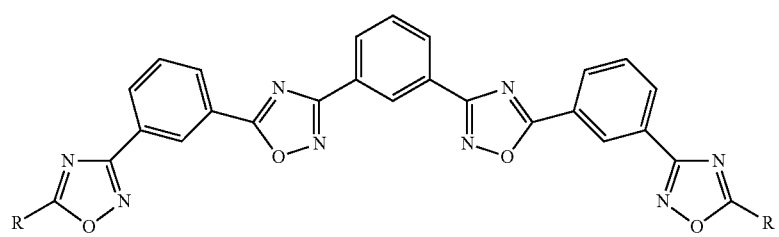

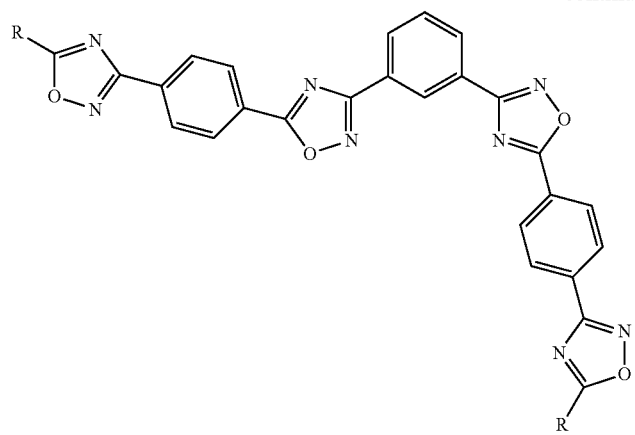
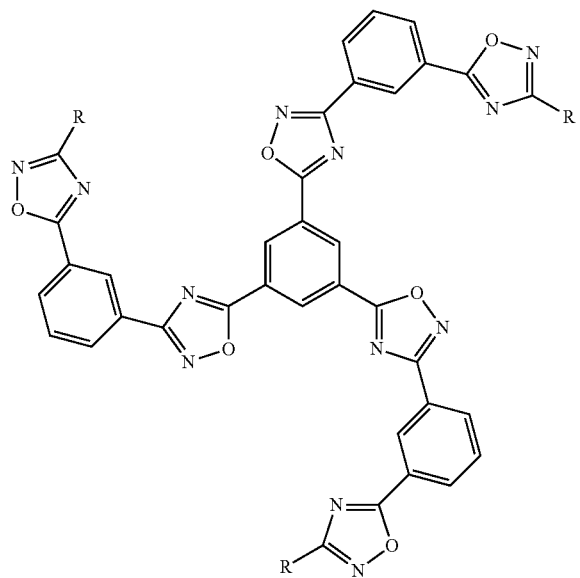
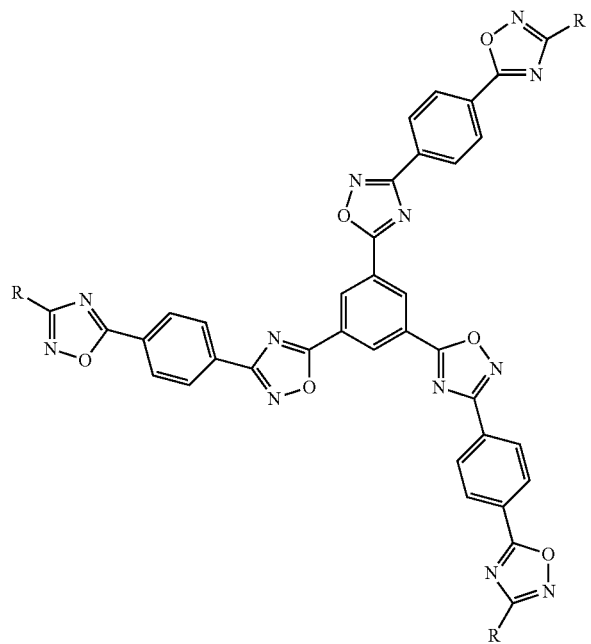

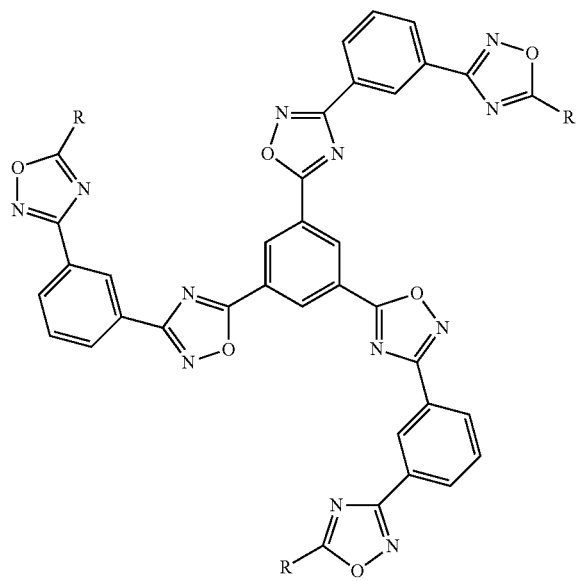
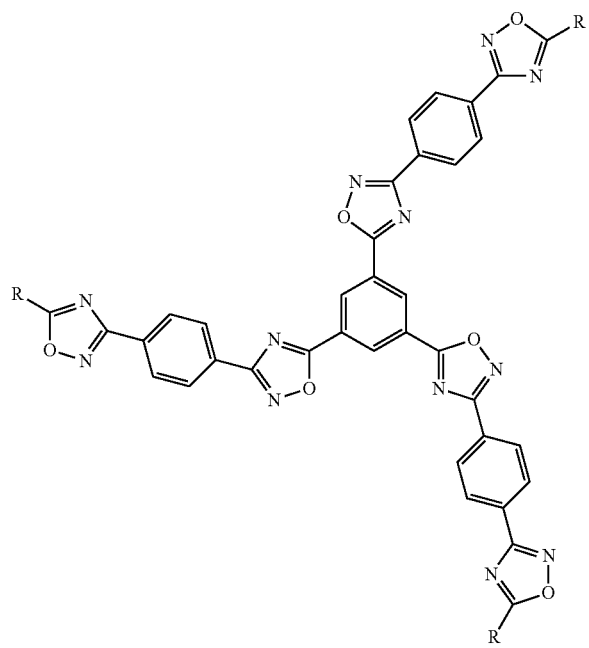

-continued
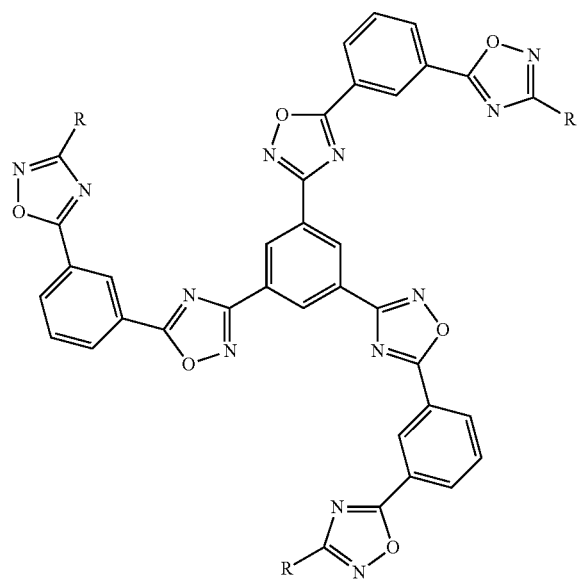
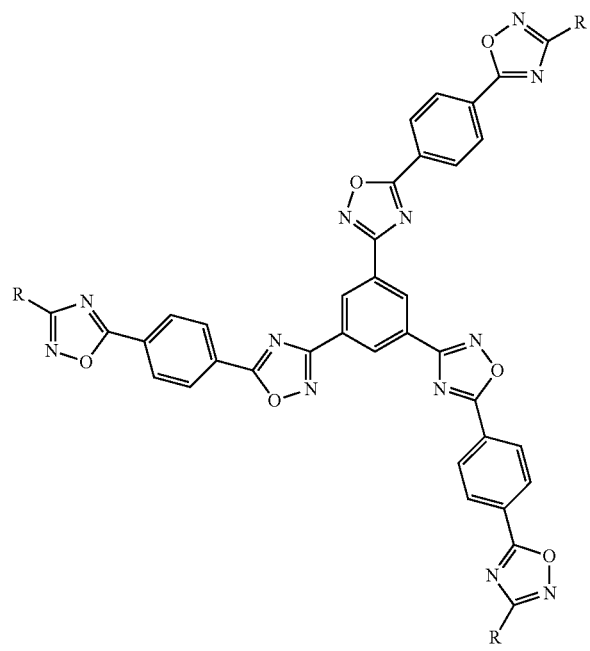

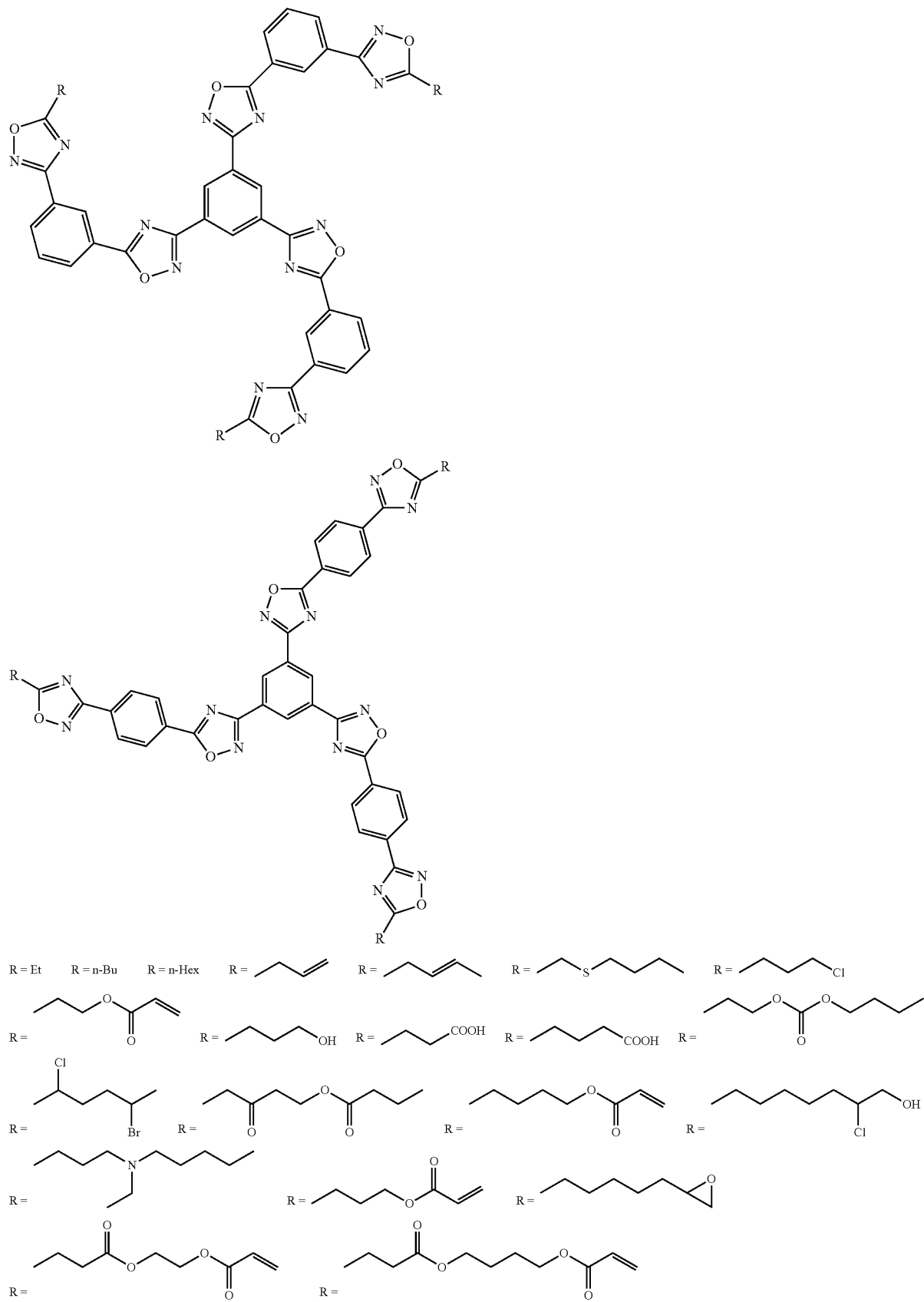

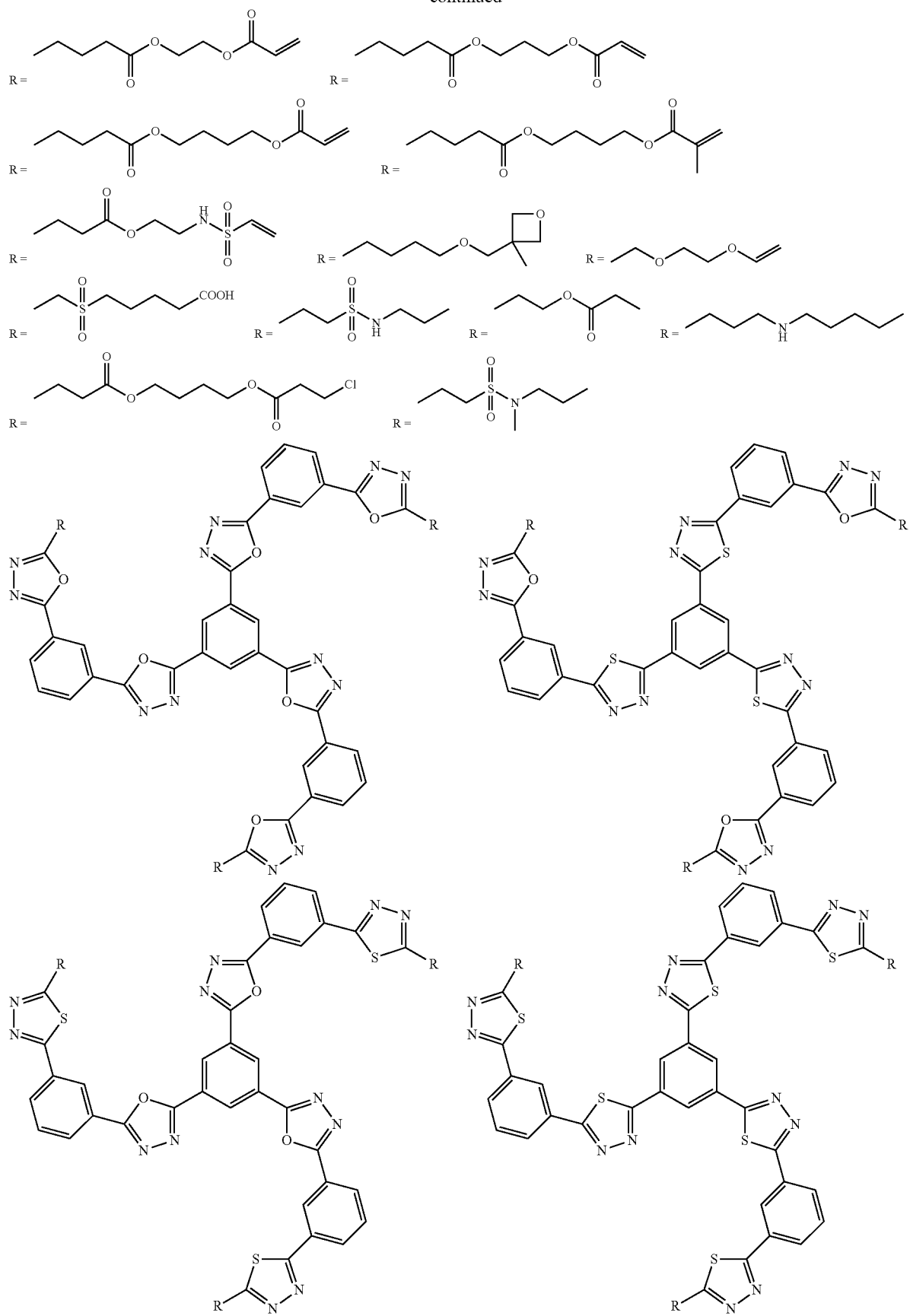

25
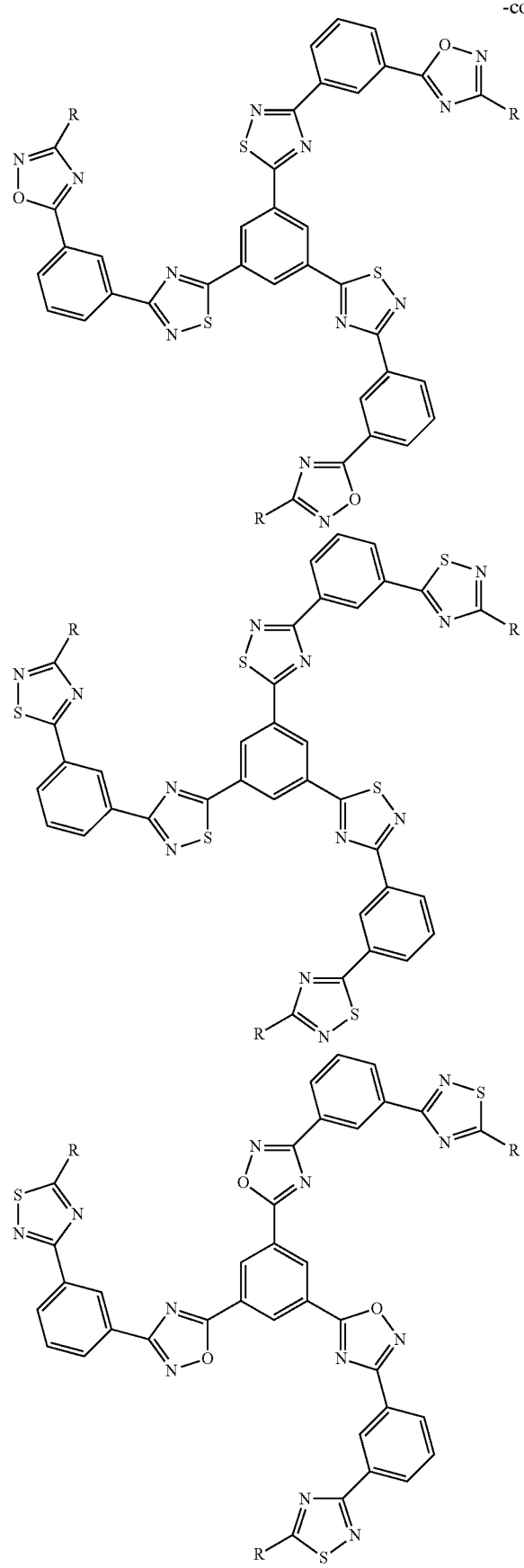
26
-continued
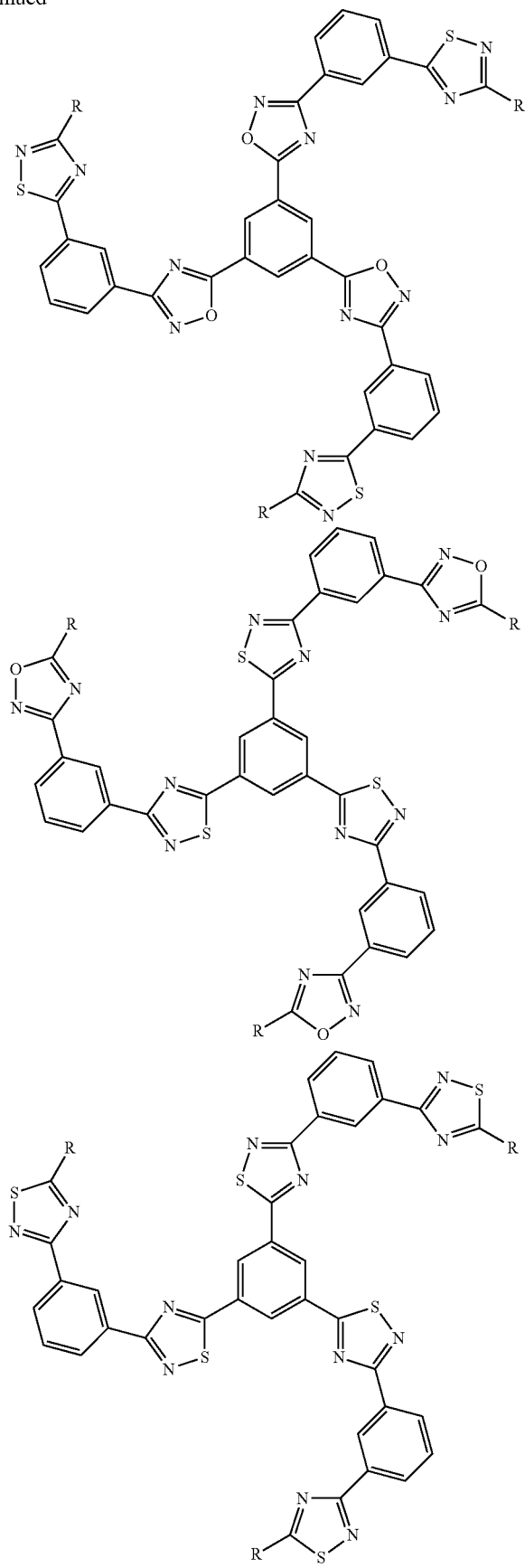

27
28
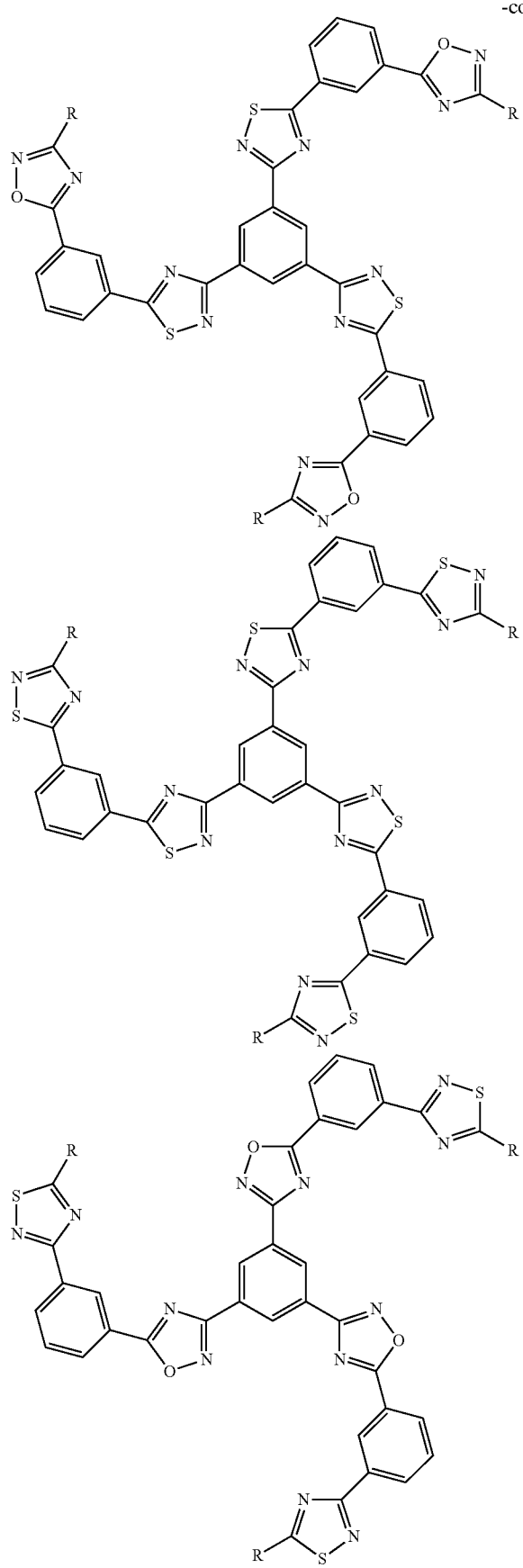
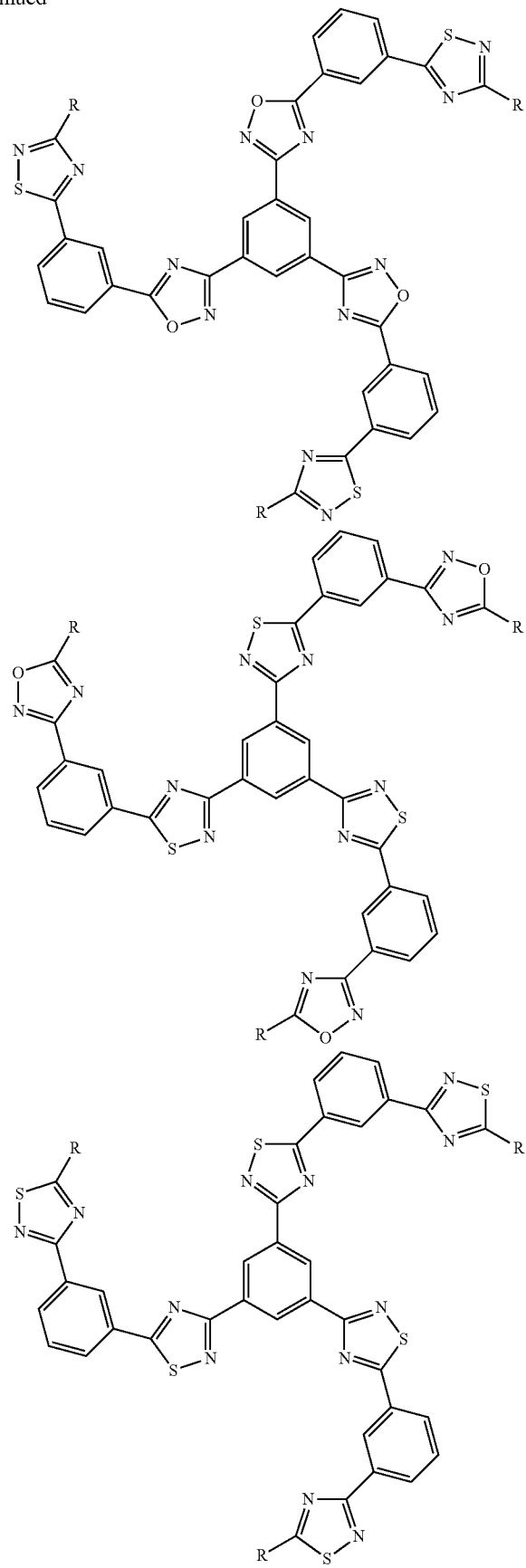

29 30
-continued
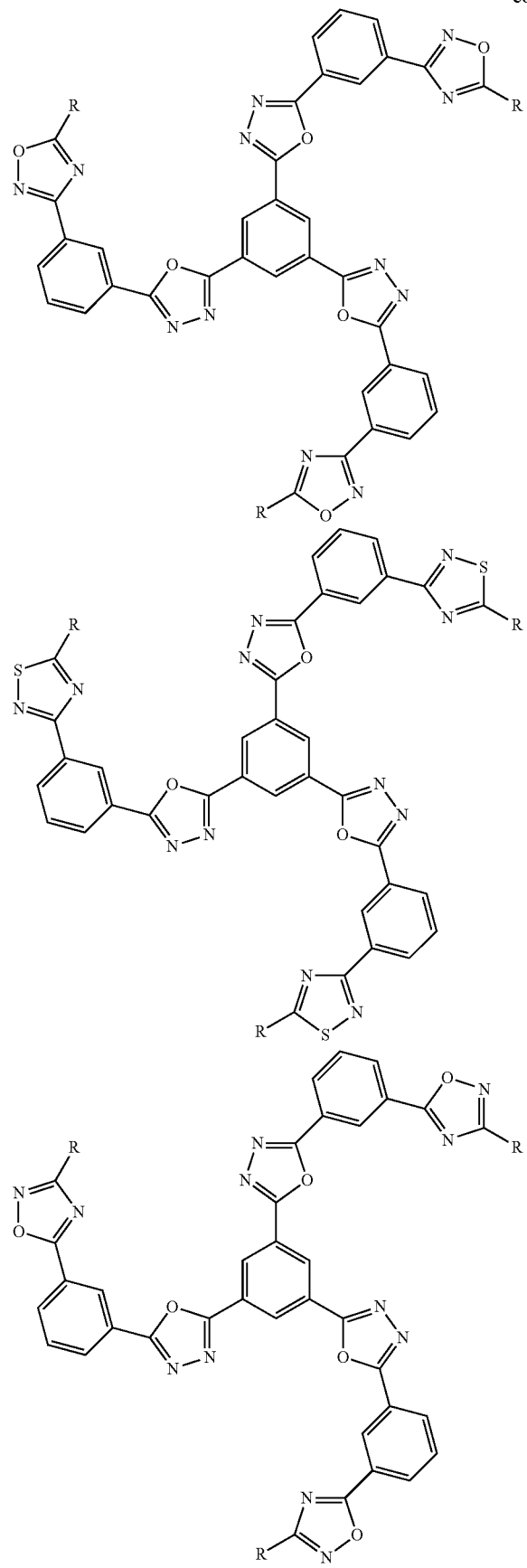

-continued
31
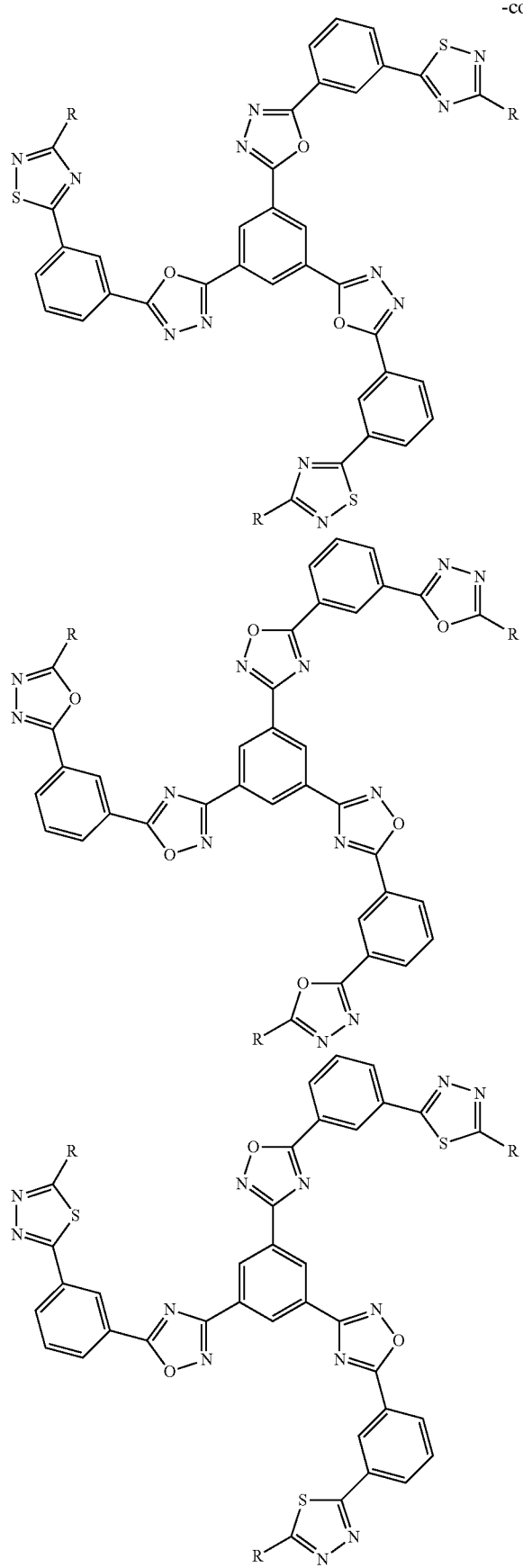
32
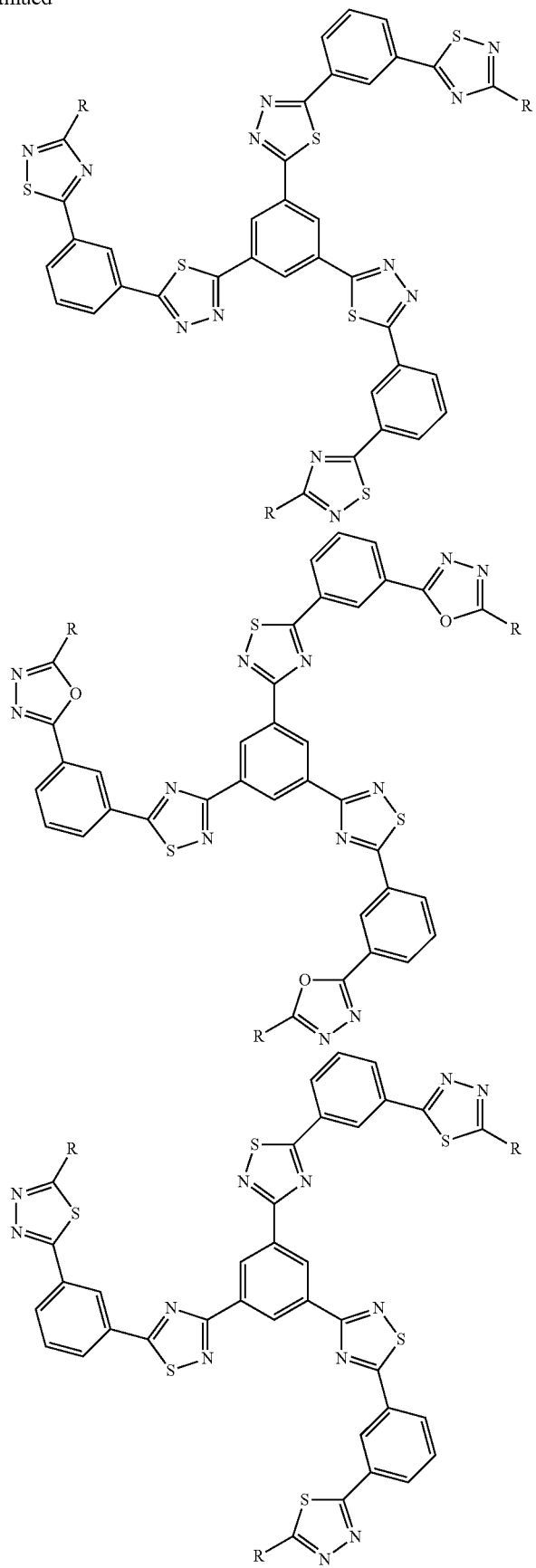

-continued
33
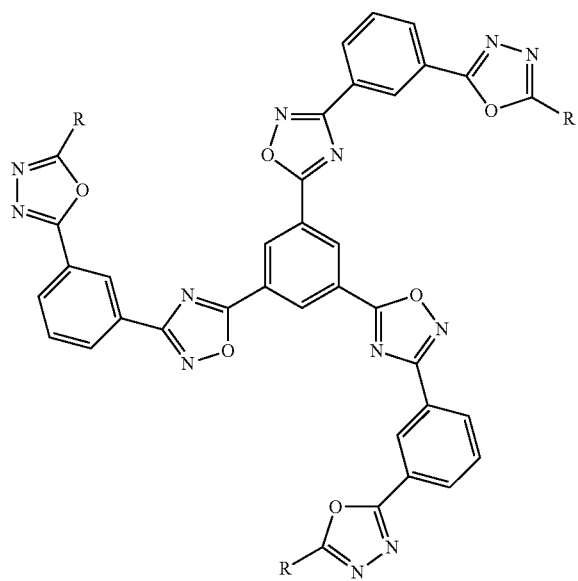
34
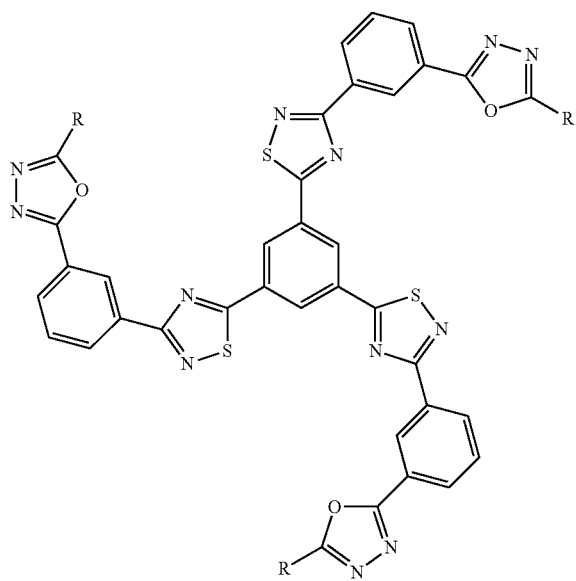
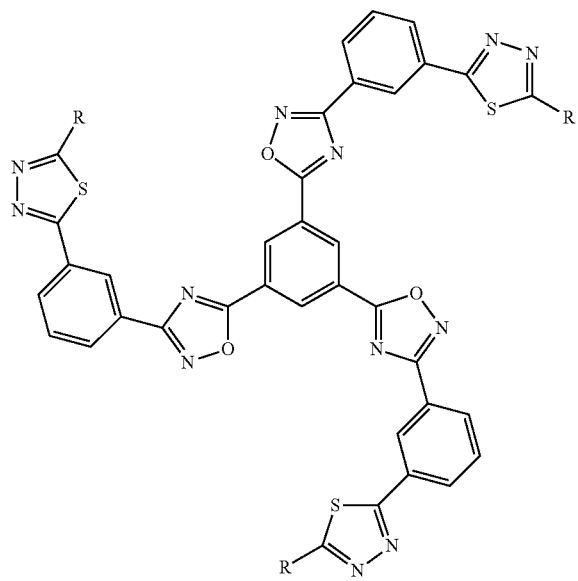
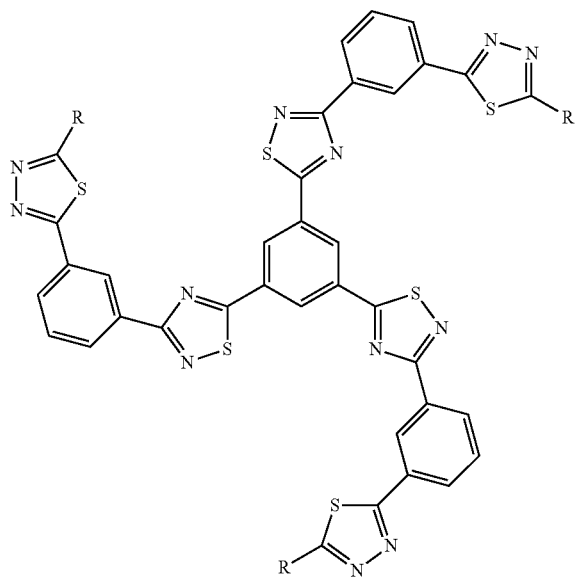
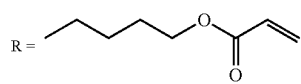

-continued
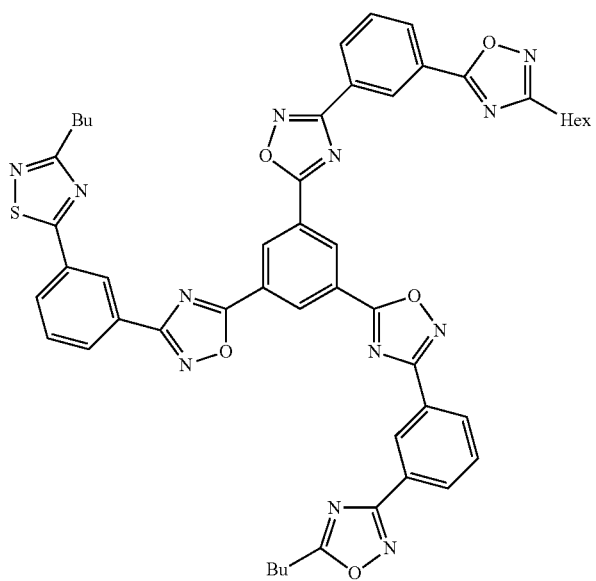
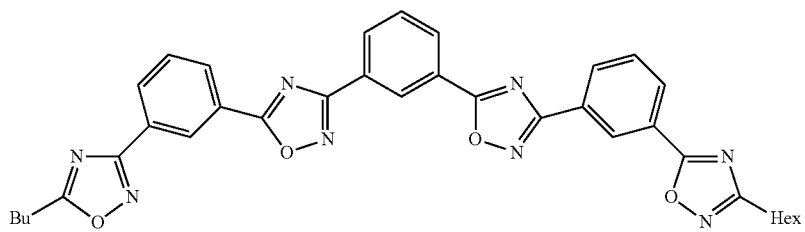
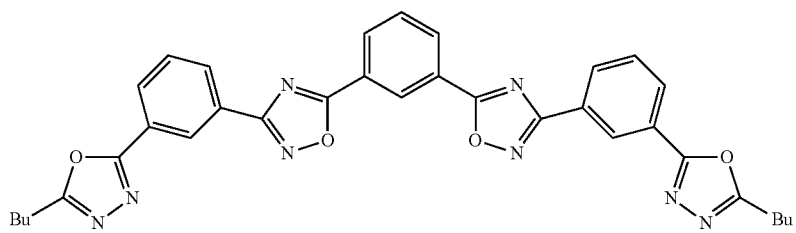
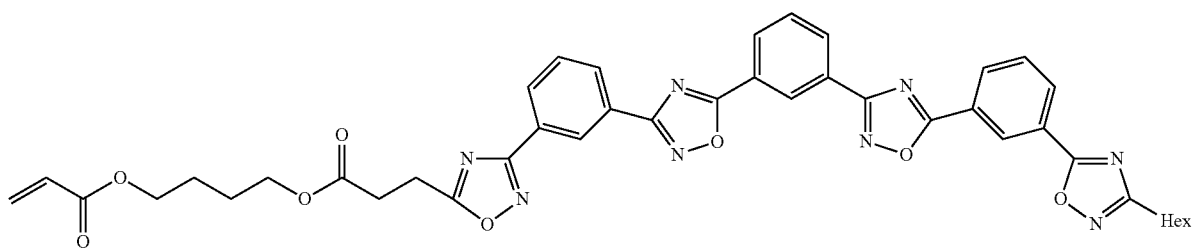
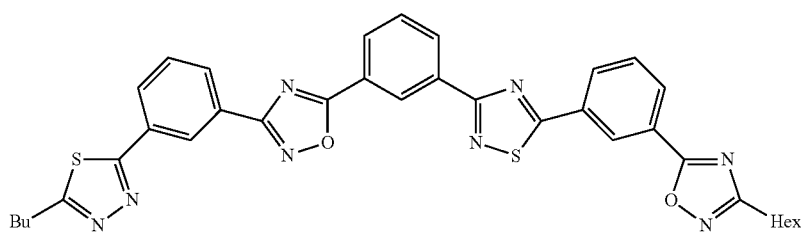

-continued

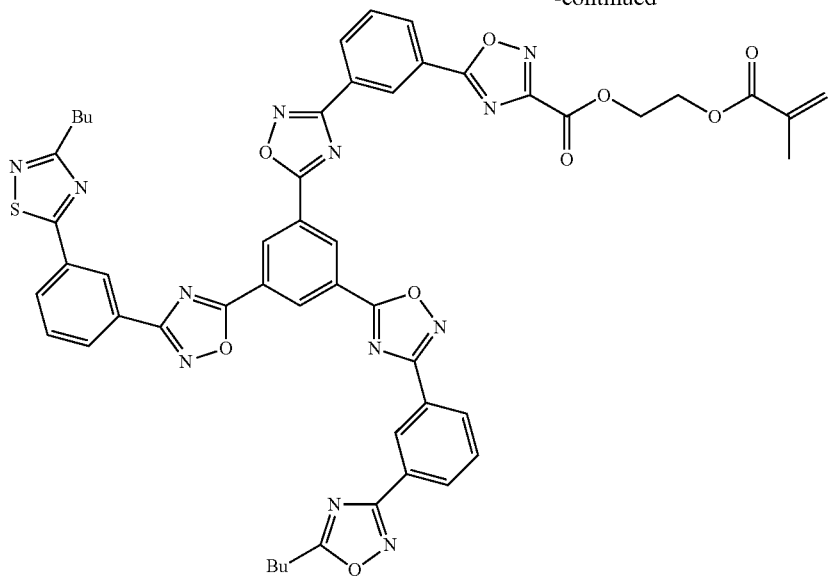

Examples of the compound represented by formula (1) include liquid crystal compounds having a liquid crystal phase such as a discotic nematic liquid crystal phase. One feature of the liquid crystal compound resides in having high Δn and a high temperature at which it starts to exhibit the liquid crystal phase and a wide temperature range in which it continues to exhibit the liquid crystal phase. For example, some compounds represented by formula (1) have higher Δn and a higher temperature at which it starts to exhibit the liquid crystal phase and a wider temperature range in which it continues to exhibit the liquid crystal phase, compared with any compounds having no 5-membered heterocyclic group as $L^{11}$, $L^{21}$ or $L^{31}$ in (1) and (1a). Therefore, by using the compound represented by formula (1) or (1a), an optical film having optical properties based on high Δn of the compound can be produced stably with a wide latitude Preferable examples of the compound represented by formula (1) or (1a) include discotic liquid crystal compounds exhibiting a discotic nematic liquid crystal phase at the temperature within the range from 0 to 300 degrees Celsius. The compounds exhibiting a discotic nematic liquid crystal phase at the temperature within the range from 20 to 250 degrees Celsius are more preferable. However, the temperature range is not limited to the above-mentioned range.

(1)-2 Method of Producing Compound of Formula (1) or (1a)

The compound represented by formula (1) or (1a) can be produced by combining two or more organic synthetic steps. More specifically, the compound may be produced with reference to the methods described in JPA Nos. 2006-76992 and 2007-2220.

The compound represented by formula (1) or (1a) can be produced by using a compound represented by formula (1b) shown below as a reagent.

The present invention relates also to the compound represented by formula (1b) which is useful for producing the compound represented by formula (1) or (1a).

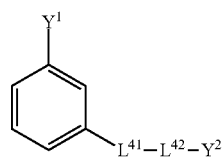

(1b)

In formula (1b), $L^{41}$ represents formula (D), (E) or (F).

(D)

(E)

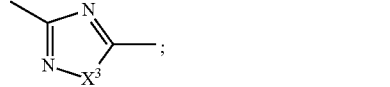

(F)

In formula (1b), $X^1$, $X^2$ and $X^3$ each independently represent an oxygen atom, a sulfur atom, methylene or imino. Preferable examples of $X^1$, $X^2$ and $X^3$ are same as those exemplified as preferable examples of $X^1$, $X^2$ and $X^3$ in formula (1).

In formula (1b), $Y^1$ represents CN, COOH or amidoxime.

Examples of the compound represented by formula (1b) include compounds represented by formula (1b-1), (1b-2), and (1b-3) shown below.

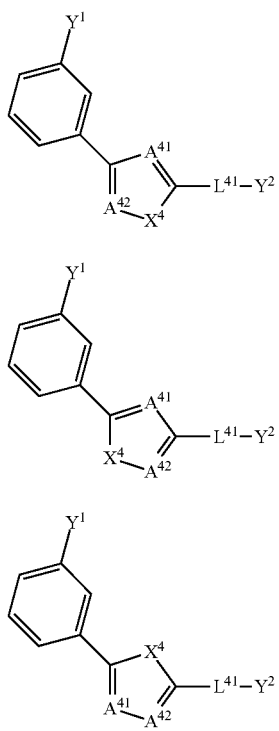

(1b-1)

(1b-2)

(1b-3)

In the formulae, $A^{41}$ and $A^{42}$ each independently represent a nitrogen atom or methine; $X^4$ each represents an oxygen atom, a sulfur atom, methylene or imino; $Y^1$ each represents CN, COOH or amidoxime; $Y^2$ each represents COOH, OH, $C_{1-4}$ alkyl, a halogen atom or a hydrogen atom; $L^{41}$ each represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —SO$_2$—, —NR—, —NRSO$_2$— and —SO$_2$NR— where R represents a hydrogen atom or a $C_{1-4}$ alkyl, or provided that one hydrogen atom or two or more hydrogen atoms in the alkylene or the alkenylene may be replaced with one halogen atom or two or more halogen atoms.

The compound represented by formula (1b) can be produced by combining two or more organic synthetic steps.

The methods with the compound represented by formula (1b) for producing the compound represented by formula (1) or (1a) are as follows.

According to the method with the compound of formula (1b) in which $Y^1$ is amidoxime group, the amidoxime group is reacted with an activated carboxyl group to give a 1,2,4-oxadiazole derivative as shown in the following scheme. Then, if necessary, the 1,2,4-oxadiazole derivative may be reacted with other reagent(s) to give the compound represented by formula (1) or (1a).

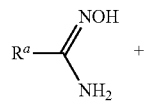

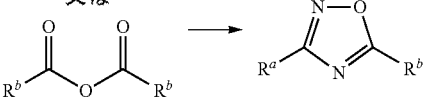

According to the method with the compound of formula (1b) in which $Y^1$ is a cyano group, after the cyano group is converted into an amidoxide group, the amidoxime group is reacted with an activated carboxyl group to give a 1,2,4-oxadiazole derivative as shown in the above-described scheme. Then, if necessary, the 1,2,4-oxadiazole derivative may be reacted with other reagent(s) to give the compound represented by formula (1) or (1a).

According to the method with the compound of formula (1b) in which $Y^1$ is a carboxyl group, after the carboxyl group, COOH, is converted into an acid chloride or the like, the acid chloride is reacted with an amidoxime derivative or hydrazine derivative to give a 1,2,4-oxadiazole derivative or 1,3,4-oxadiazole derivative as shown in the above-described scheme. Then, if necessary, the 1,2,4- or 1,3,4-oxadiazole derivative may be reacted with other reagent(s) to give the compound represented by formula (1) or (1a).

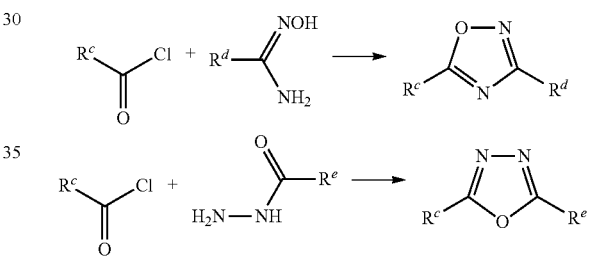

As shown above, by using the compound represented by formula (1b), which is a intermediate of the compound represented by formula (1), 1,2,4- or 1,3,4-oxadiazole derivative can be produced according to a typical and simple method.

In formula (1b), $Y^2$ corresponds to $Q^{11}$, $Q^{21}$ or $Q^{31}$ in formula (1) or (1a), and, if necessary, any reaction for converting $Y^2$ into desirable $Q^{11}$, $Q^{21}$ or $Q^{31}$ may be carried out.

The compound represented by formula (1b) can be produced by combining two or more organic synthetic steps. For example, the compound of formula (1b) can be produced by using the compound of formula (1c) as a starting material.

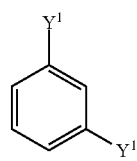

(1c)

In formula (1c), $Y^1$ has same meaning as that in formula (1b), that is, $Y^1$ represents CN, COOH or amidoxime. $Y^1$ may be converted into -$L^{41}$-$L^{42}$-$Y^2$ according to the above-described method.

Examples of the compound represented by formula (1b) include, however are not limited to, those shown below.
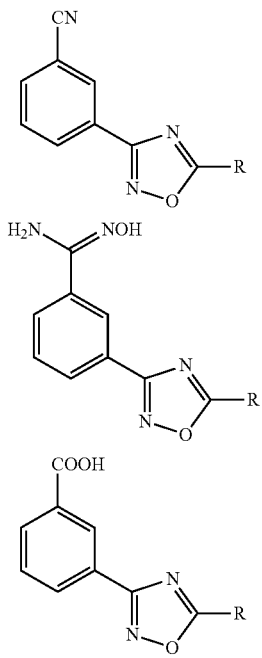
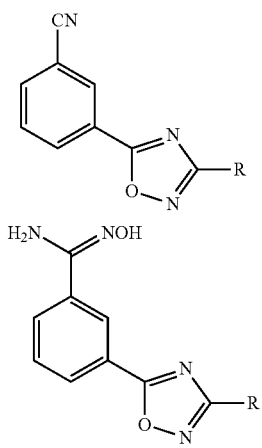
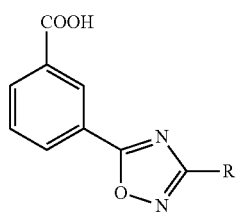
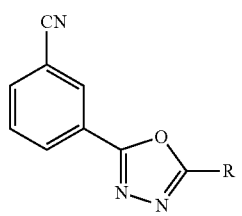
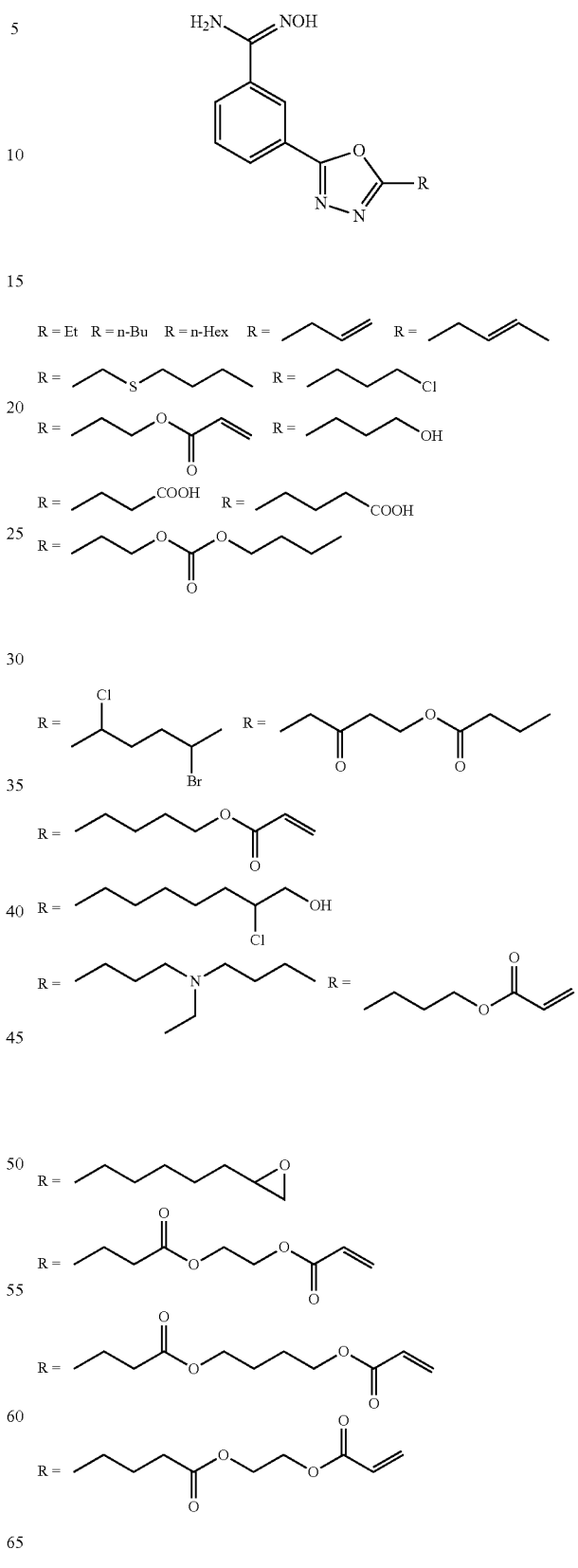

-continued
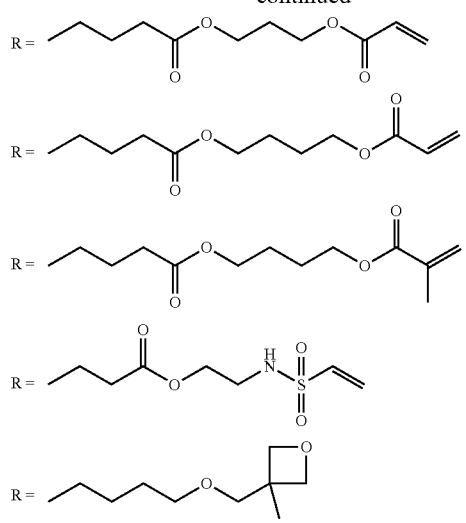
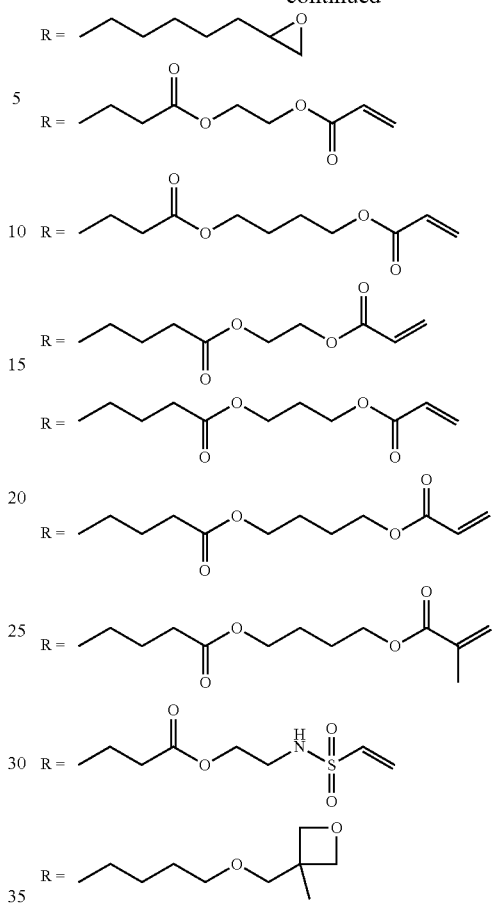
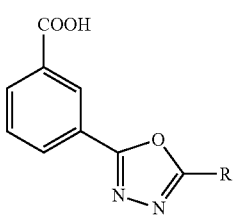
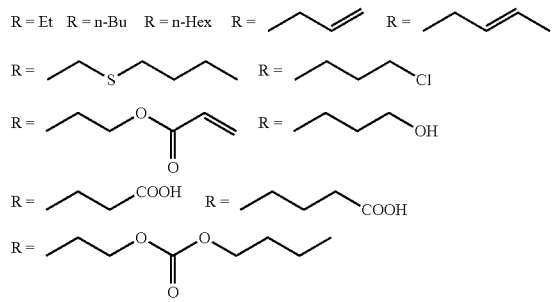
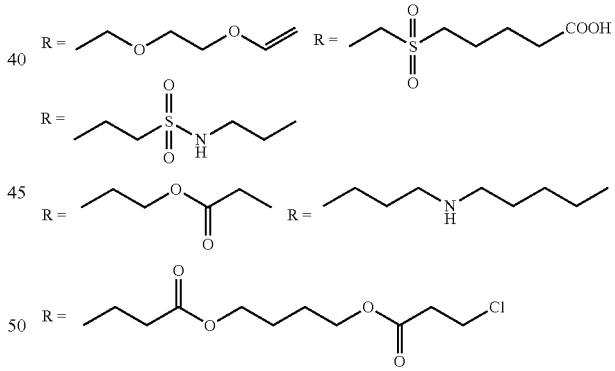
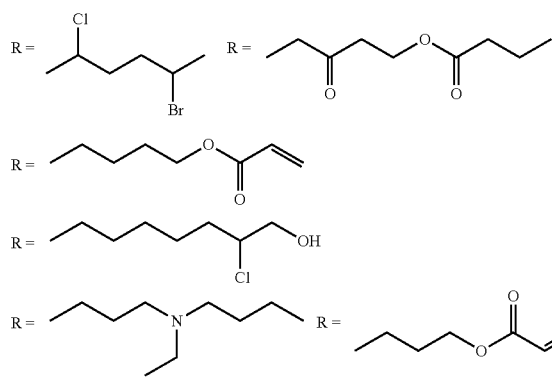
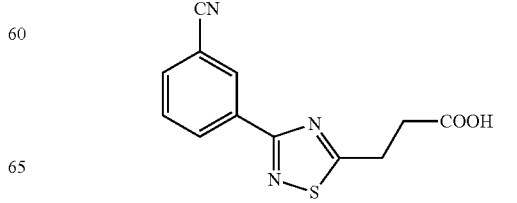

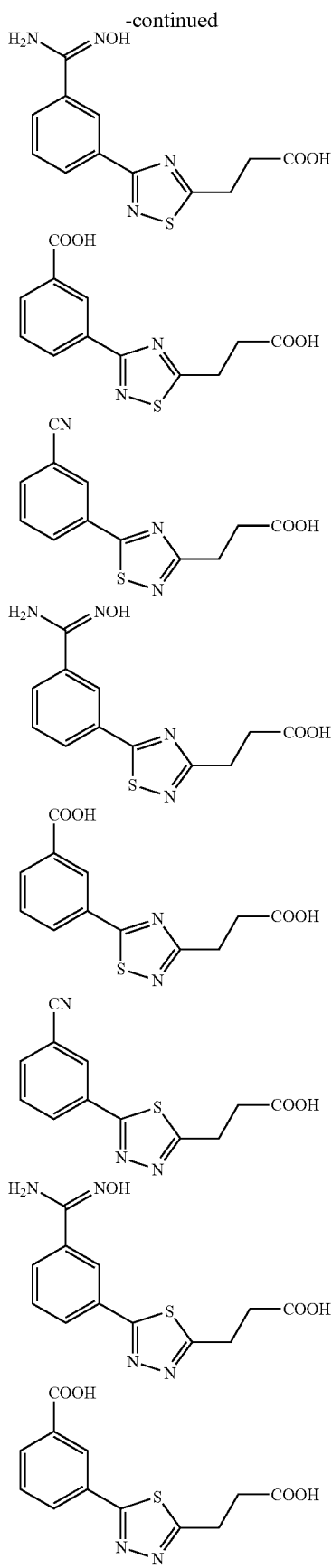

(1)-3 Additive

One example of the present invention is an optical film formed of a composition containing at least one compound represented by formula (1) or (1a). The optical film may be any self-supportable film or not self-supportable film such as a cured film to be supported by a substrate. One example of the composition is a liquid crystal composition exhibiting liquid crystallinity. Preferably, the composition contains the compound of formula (1) or (1a) as a main ingredient, and more specifically, the composition preferably contains the compound of formula (1) or (1a) in an amount of equal to or more than 50% by mass. The composition may contain at least one liquid crystal compound other than the compound of formula (1). Examples of the liquid crystal compound which can be used in the present invention include rod-like liquid crystals and discotic liquid crystals. The composition may contain also at least one additive in combination with the compound of formula (1). An agent capable of controlling alignment at the air-interface, an agent capable of reducing defects, a polymerization initiator and a polymerizable monomer are described in detail below as an example of the additive which can be used in the present invention.

Agent Capable of Controlling Alignment at the Air-Interface:

The composition may be aligned with the air-interface tilt angle at the air-interface. The tilt angle may be varied depending on the types of the liquid crystal compounds or the additives to be used in the composition, and thus, it may be necessary to be adjusted to the appropriate range depending on the purpose.

The tilt angle may be controlled by application of an external force such as an electric and magnetic fields or addition of any additive(s). Adding any additive(s) is preferable. Examples of such an additive include compounds having at least one, preferably two or more, substituted or non-substituted $C_{6-40}$ aliphatic group(s) in a molecule and compounds having at least one, preferably two or more, substituted or non-substituted $C_{6-40}$ aliphatic oligosiloxanoxy group(s) in a molecule. For example, the hydrophobic compounds having an effect of excluding-volume disclosed in JPA No. 2002-20363 can be used as an agent capable of controlling alignment at the air-interface.

The amount of the agent capable of controlling alignment at the air-interface to be added to the composition is preferably from 0.001 to 20% by mass, more preferably from 0.01 to 10% by mass, and much more preferably from 0.1 to 5% by mass with respect to the total mass of the composition (if the composition is a coating liquid or the like, the total mass is the solid total mass, and hereinafter, the term has the same meaning).

Agent Capable of Reducing Defects:

Usually, any polymer may be added to the composition for preventing any defects occurring in a coating step. The polymer to be used is not limited unless adding the polymer to the composition would change the tilt angle or inhibit the alignment of the composition remarkably.

Examples of the polymer include those described in JPA No. 8-95030; and among these, cellulose acylates are preferable. Examples of the cellulose acylate which can be used in the invention include cellulose acetate, cellulose acetate propionate, hydroxy propyl cellulose and cellulose acetate butyrate.

In terms of avoiding inhibition of the alignment, the amount of the polymer to be added to the composition is preferably from 0.1 to 10% by mass, more preferably from 0.1 to 8% by mass, and much more preferably from 0.1 to 5% by mass with respect to the total mass of the composition.

Polymerization Initiator:

When an optically anisotropic layer is prepared by using the composition, for example, the composition may be heated by the temperature at which the composition exhibits a liquid crystal phase and be then cooled while the alignment is maintained. In this way, the optically anisotropic layer formed of the fixed alignment of composition may be obtained without losing the alignment state. Alternatively, the layer may be obtained as follows. The composition containing a polymerization initiator may be heated by the temperature at which the composition exhibits a liquid crystal phase, be polymerized and then be cooled, thereby to fix the alignment. In the invention, the latter manner, that is, the manner employing polymerization is preferable for fixing the alignment state. Examples of the polymerization reaction include thermal polymerization reactions using a thermal polymerization initiator, photo-polymerization reactions using a photo-polymerization initiator and polymerizations with irradiation of electron beam. Photo-polymerization reactions and polymerizations with irradiation of electron beam are preferred in terms of avoiding deformation or degradation of the support or the like.

Examples of photo-polymerization initiators include alpha-carbonyl compounds (described in U.S. Pat. Nos. 2,367,661 and 2,367,670), acyloin ethers (described in U.S. Pat. No. 2,448,828), alpha-hydrocarbon-substituted aromatic acyloin compounds (described in U.S. Pat. No. 2,722,512), polynuclear quinone compounds (described in U.S. Pat. Nos. 3,046,127 and 2,951,758), combinations of triarylimidazole dimers and p-aminophenyl ketone (described in U.S. Pat. No. 3,549,367), acridine and phenazine compounds (described in Japanese Laid-Open Patent Publication (Tokkai) Showa No. 60-105667 and U.S. Pat. No. 4,239,850) and oxadiazole compounds (described in U.S. Pat. No. 4,212,970).

The amount of the photo-polymerization initiator to be added to the composition is preferably 0.01 to 20% by mass, more preferably 0.5 to 5% by mass with respect to the total mass of the composition.

Polymerizable Monomer:

The composition may contain polymerizable monomer(s). The polymerizable monomer which can be used in the invention is not limited so far as the monomer is compatible with the compound of formula (1) and doesn't inhibit the alignment of the composition remarkably. Polymerizable ethylenic unsaturated groups such as vinyl, vinyloxy, acryloyl and methacryloyl are preferable.

The amount of the polymerizable monomer to be added to the composition is preferably 0.5 to 50% by mass, and more preferably 1 to 30% by mass with respect to the total mass of the composition. Using any monomer having two or more reactive groups in a molecule is preferable in terms of improvement in the adhesion to the alignment layer.

The composition may be prepared as a coating liquid. The solvent which is used for preparing the coating liquid is desirably selected from organic solvents. Examples of the organic solvent include amides such as N,N-dimethylformamide, sulfoxides such as dimethylsulfoxide, heterocyclic compounds such as pyridine, hydrocarbons such as benzene or hexane, alkyl halides such as chloroform or dichloromethane, esters such as methyl acetate or butyl acetate, ketones such as acetone or methylethyl ketone and ethers such as tetrahydrofuran or 1,2-dimethoxyethane. Among these, esters and ketones are preferable; and ketones are more preferable. Plural types of organic solvents may be used in combination.

1.-(4) Method for Producing Optical Film

The optical film of the invention may be produced by fixing the alignment of the composition. The optical film is useful as an optical element such as a retardation plate.

One example of the method for producing the optical film is described below. However, the method is not limited to the method described below.

At first, the composition containing the compound of formula (1) is applied to a surface of a support or an alignment layer formed on the support. If necessary, the composition is heated, and then aligned in a desired alignment state. Next, polymerization is carried out to fix the alignment state. In this way, the optical film of the invention can be produced. Examples of the additive which can be added to the composition include the agent capable of controlling alignment at the air-interface, the agent capable of reducing defects, the polymerization initiator and the polymerizable monomer described above.

The coating liquid may be applied to a surface according to various techniques (e.g., wire bar coating, extrusion coating, direct gravure coating, reverse gravure coating and die coating).

For achieving a uniform alignment, an alignment layer is preferably used. However, for achieving an alignment in which an optical direction is along with the normal direction of the layer plane, that is, homeotropic alignment, any alignment layer may not be necessary.

The alignment layer that can be employed in the present invention may be provided by rubbing a layer formed of an organic compound (preferably a polymer), oblique vapor deposition, the formation of a layer with microgrooves, or the deposition of organic compounds (for example, omega-tricosanoic acid, dioctadecylmethylammonium chloride, and methyl stearate) by the Langmuir-Blodgett (LB) film method. Further, alignment layers imparted with orientation functions by exposure to an electric or magnetic field or irradiation with light are also known.

The alignment layer is not limited so far as it can control the alignment of the composition. In the invention, the alignment layer prepared by a rubbing treatment or by irradiation with light is preferable. The alignment layer prepared by a rubbing treatment is especially preferable. Usually, the rubbing treatment is carried out by rubbing a surface of a polymer layer with a paper or cloth several times along a same direction. In the invention, for example, the rubbing treatment may be carried out according to the method described in EKISYOU BINRAN (Handbook of Liquid Crystal), published by Maruzen. The thickness of the alignment layer is preferably from 0.01 to 10 micro meters, and more preferably from 0.05 to 3 micro meters.

Next, for fixing the alignment state, preferably, polymerization is carried out. Preferably, the composition containing a polymerization initiator is used and polymerization of the composition is carried out under irradiation with light. UV light is preferably used. The irradiation energy is preferably 10 mJ/cm$^2$ to 50 J/cm$^2$, more preferably 50 mJ/cm$^2$ to 800 mJ/cm$^2$. Irradiation may be carried out under heating to accelerate the photo-polymerization reaction. The concentration of oxygen in the atmosphere may influence the polymerization degree. Therefore, when the desired polymerization degree is not achieved during the polymerization under air, preferably, the concentration of oxygen is lowered by replacing air with nitrogen gas. The concentration of oxygen is preferably equal to or less than 10%, more preferably equal to or less than 7% and even more preferably equal to or less than 3%.

In the present invention, the meaning of "a fixed alignment state" is a typical and most preferable state, that is, a state maintaining the alignment; however, it is not limited to the typical state. More specifically, the meaning of "a fixed alignment state" indicates the state which has no fluidity at a temperature within the range from 0 to 50 degrees Celsius, or, under severer condition, from −30 to 70 degrees Celsius, is not changed depending on any external field or any external force and is stably kept. It is to be noted that after the optically anisotropic layer is formed by fixing the alignment state, the composition has any liquid crystallinity no longer. For example, the liquid crystal compound may lose any liquid crystallinity after it is polymerized by polymerization or crosslinking-reaction under irradiation with heat or light.

2. Retardation Plate

The present invention relates also to a retardation plate comprising a transparent support and at least one optically anisotropic layer thereon, wherein the at least one optically anisotropic layer is an optical film of the invention.

The materials or methods for producing the optical film are same as those described above, and their preferable examples are also same as those described above.

As the transparent support, a substrate having light transmissivity of 80% or more may be used. Polymer films and glass plates are preferable. Examples of the polymer that constitutes the polymer film include cellulose acylates (e.g., cellulose diacetate and cellulose triacetate), norbornene polymers and poly(meth)acrylate esters. Commercially-available polymers may also be used. Among these, in terms of optical properties, cellulose acylates are preferable and cellulose esters with any low-fatty acid are more preferable. The low-fatty acid is a C6 or shorter fatty acid, and the number of carbon atoms in the low-fatty acid is preferably 2 (cellulose acetate), 3 (cellulose propionate) or 4 (cellulose butyrate). Cellulose triacetate is especially preferable. Esters of mixed fatty acids such as cellulose acetate propionate and cellulose acetate butyrate are preferable. A cellulose acylate film produced according to a solvent cast method is preferable. In addition, even conventional polycarbonates, polysulfones and other polymers that may readily express birefringence may also be used, so far as their birefringence expression is controlled through modification of their molecules as in WO00/26705.

The polymer film to be used as a support may be optically isotropic or anisotropic. Depending on the application of the optical film, the polymer film may be selected from various polymers having optical properties respectively. An alignment layer, which may be used for preparing an optically anisotropic layer, may be disposed between the support and the optically anisotropic layer.

The retardation plate of the invention may be used as an optical compensation film which contributes to improving the viewing-angle properties of a liquid crystal display device. The retardation plate may be incorporated into a liquid crystal display device as an independent member. Or the retardation plate of the invention may be incorporated into a liquid crystal display device as a partial member of an elliptical polarizing plate together with a linear polarizing film.

Hereinafter, the elliptical polarizing plate having the retardation plate of the invention will be described in detail.

3. Elliptical Polarizing Plate

An elliptical polarizing plate can be produced by combining the retardation plate of the invention and a linear polarizing film (referred to as "polarizing film" hereinafter). In the description, the term "an elliptically polarizing plate" is used as a meaning including a circularly polarizing plate as well as usual.

The polarizing film includes an iodine-based polarizing film, a dichroic dye-containing polarizing film and a polyene-type polarizing film. The iodine-based polarizing film and the dye-containing polarizing film may be produced generally by the use of polyvinyl alcohol films. The polarization axis of the polarizing film corresponds to the direction perpendicular to the stretching direction of the film.

Preferably, the polarizing film is disposed on the optically anisotropic layer of the retardation plate. And a protective film is disposed on the other surface of the polarizing film. The protective film is preferably a transparent protective film having a light transmittance of at least 80%. The transparent protective film is generally a cellulose acylate film, preferably a triacetyl cellulose film. The cellulose acylate film is preferably formed according to a solvent casting method. The thickness of the protective film is preferably from 20 to 500 micro meters more preferably from 50 to 200 micro meters.

4. Liquid Crystal Display Device

The present invention relates to a liquid crystal display device having at least the retardation plate and/or the elliptical polarizing plate of the invention. It is possible to provide a liquid crystal display device of which viewing angle is widened by using the retardation plate of the invention. The retardation plates (optical compensation sheets) to be used for optical compensation of TN-mode liquid crystal cells are described in JPA No. 6-214116, U.S. Pat. Nos. 5,583,679 and 5,646,703 and Germany Patent Publication No. 3911620A[1]. The retardation plates (optical compensation sheets) to be used for optical compensation of IPS- or FLC-mode liquid crystal cells are described in JPA No. 10-54982. The retardation plates (optical compensation sheets) to be used for optical compensation of OCB- or HAN-mode liquid crystal cells are described in U.S. Pat. No. 5,805,253 and International Publication WO96/37804 pamphlet. The retardation plates (optical compensation sheets) to be used for optical compensation of STN-mode liquid crystal cells are described in JPA No. 9-26572. The retardation plates (optical compensation sheets) to be used for optical compensation of VA-mode liquid crystal cells are described in Japanese Patent No. 2866372.

According to the invention, various retardation plates (optical compensation sheets) to be used for optical compensation of liquid crystal cells employing any mode may be produced with reference to the above-described publications. The retardation plate of the invention may be used in various liquid crystal display device employing any mode such as TN (Twisted Nematic), IPS (In-Plane Switching), FLC (Ferroelectric Liquid Crystal), OCB (Optically Compensatory Bend), STN (Super Twisted Nematic), VA (Vertically Aligned) and HAN(Hybrid Aligned Nematic).

Usually, the liquid crystal display device usually at least has a liquid crystal cell, a polarizing element and a retardation plate (optical compensation film). The polarizing element usually contains a polarizing film and a protective film. The polarizing film and protective film which are described above as those in the elliptical polarizing plate can be used.

EXAMPLES

Paragraphs below will further specifically explain the present invention referring to Examples and Comparative Examples, without limiting the present invention. The lubricant compositions in Examples and Comparative Examples were evaluated according to the methods described below.

Example 1

Synthesis of Compound (1)

Compound (1) was prepared in the manner as shown in the following scheme.

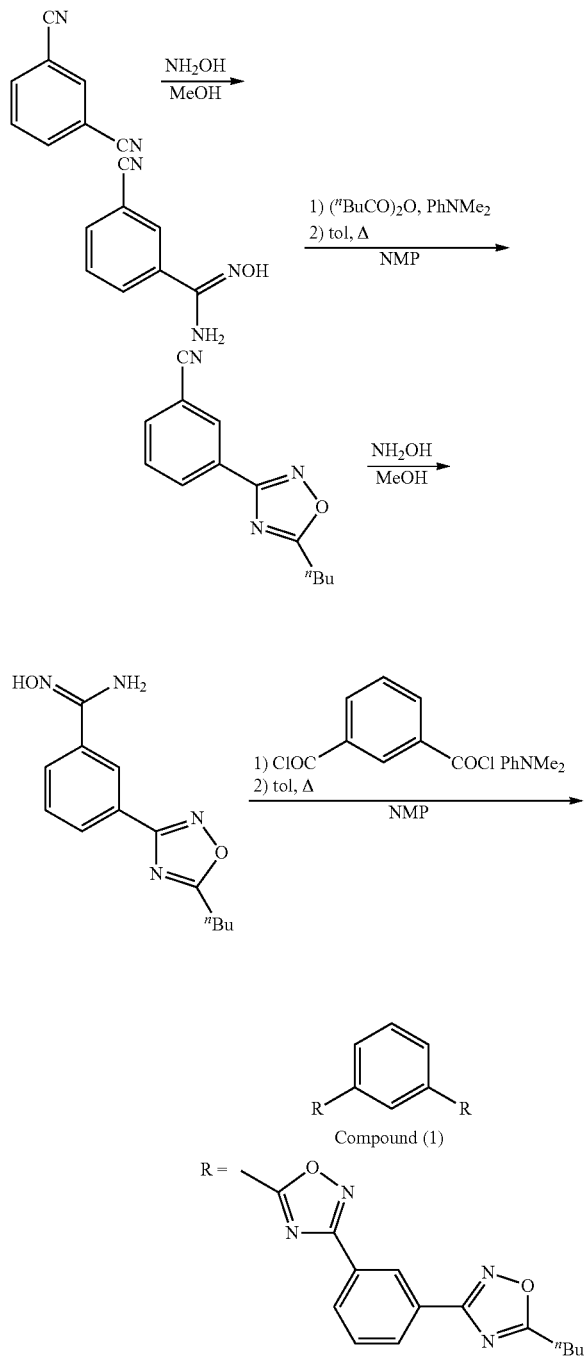

Compound (1)

Isophthalonitrile (20 g) was added to a mixture of THF (300 mL) and methanol (150 mL), was added dropwise with hydroxylamine (11 mL) at 40 degrees Celsius, and then was reacted for an hour. After that, the reaction mixture was cooled with ices, added dropwise with valeric acid anhydride (30.3 mL), and was stirred for two hours at the room temperature. The mixture was added with 400 mL of ethyl acetate, was washed with dilute hydrochloric acid, saturated sodium bicarbonate water and saturated salt solution, was condensed, and then was dehydrated by azeotropy in a mixture of NPM (100 mL) and toluene (100 mL) for two hours. The resultant was added with 400 mL of ethyl acetate, was washed with dilute hydrochloric acid, saturated sodium bicarbonate water and saturated salt solution, and was condensed to give a reaction mixture. The reaction mixture was added with 150 mL of methanol, was added dropwise with hydroxylamine (13 mL), and was reacted for an hour. After being added with 500 mL of water and being subjected to decantation, the resultant was washed with aqueous solution of citric acid and water, and then was dried with magnesium sulfate. Carrying out column-purification, 20.3 g of an amidoxime derivative was obtained with a yield constant of 50% with respect to isophthalonitrile. To NMP (50 mL), 8.9 g of the amidoxime derivative and N,N-dimethyl aniline (5.2 mL) were added, then added dropwise with NMP solution (10 mL) of isophthalonitrile (3.2 g) while being cooled with ices, and was stirred for two hours at the room temperature. The mixture was added with toluene (50 mL), and was dehydrated by azeotropy for three hours. After toluene was distilled away, the resultant was poured into dilute hydrochloric acid, was filtered, was washed with water, then was dried, and then was purified according to a column chromatography to give 9 g (95% yield constant) of a target compound, Compound (1). The identification of the compound was carried out by $^1$H-NMR.

$^1$H-NMR (CDCl$_3$) δ: 1.00 (6H, t), 1.45~1.62 (4H, m), 1.85~2.00 (4H, m), 3.00 (4H, t), 7.65 (2H, t), 7.80 (1H, t), 8.27 (2H, d), 8.38 (2H, d), 8.52 (2H, d), 8.95 (2H, s), 9.12 (1H, s).

The phase transition temperature of the obtained Compound (1) was studied by texture observation of the compound with polarization microscope. Raising the temperature to around 130 degrees Celsius, the phase was changed from the crystal phase to the discotic nematic phase; and further raising the temperature to more than 164 degrees Celsius, the phase was changed to the isotropic liquid phase. That is, from these results, it can be understood that Compound (1) exhibits a discotic nematic phase at a temperature within the range from 130 to 164 degrees Celsius.

Example 2

Synthesis of Compound (2)

Compound (2) was prepared in the manner as shown in the following scheme.

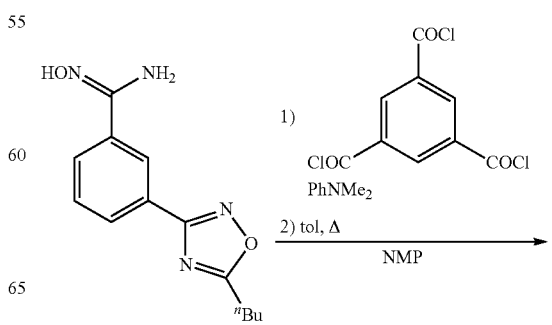

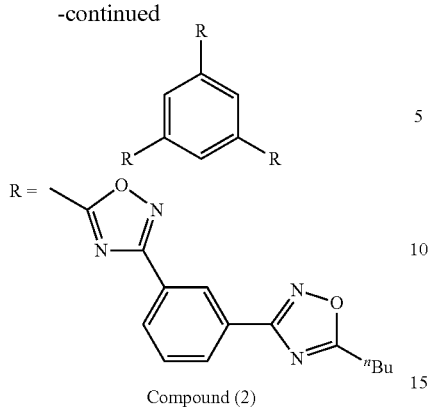

Compound (2)

To NMP (50 mL), 8.9 g of the amidoxime derivative and N,N-dimethyl aniline (5.2 mL) were added, then added dropwise with NMP solution (10 mL) of trimesic acid chloride (2.6 g) while being cooled with ices, and was stirred for two hours at the room temperature. The mixture was added with toluene (50 mL), and was dehydrated by azeotropy for three hours. After toluene was distilled away, the resultant was poured into dilute hydrochloric acid, was filtered, was washed with water, then was dried, and then was purified according to a column chromatography to give 8 g (88% yield constant) of a target compound, Compound (2). The identification of the compound was carried out by $^1$H-NMR.

$^1$H-NMR (CDCl$_3$) δ: 1.01 (9H, t), 1.43~1.60 (6H, m), 1.85~1.98 (6H, m), 3.05 (6H, t), 7.70 (3H, t), 8.30 (3H, d), 8.45 (3H, d), 8.95 (3H, s), 9.28 (3H, s).

The phase transition temperature of the obtained Compound (2) was studied by texture observation of the compound with polarization microscope. Raising the temperature to around 201 degrees Celsius, the phase was changed from the crystal phase to the discotic nematic phase; and further raising the temperature to more than 268 degrees Celsius, the phase was changed to the isotropic liquid phase. That is, from these results, it can be understood that Compound (2) exhibits a discotic nematic phase at a temperature within the range from 210 to 268 degrees Celsius.

Example 3

Synthesis of Compound (3)

Compound (3) was prepared in the manner as shown in the following scheme.

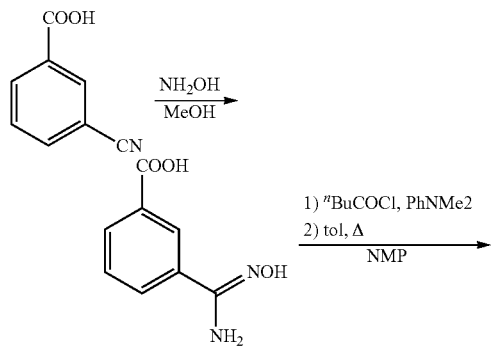

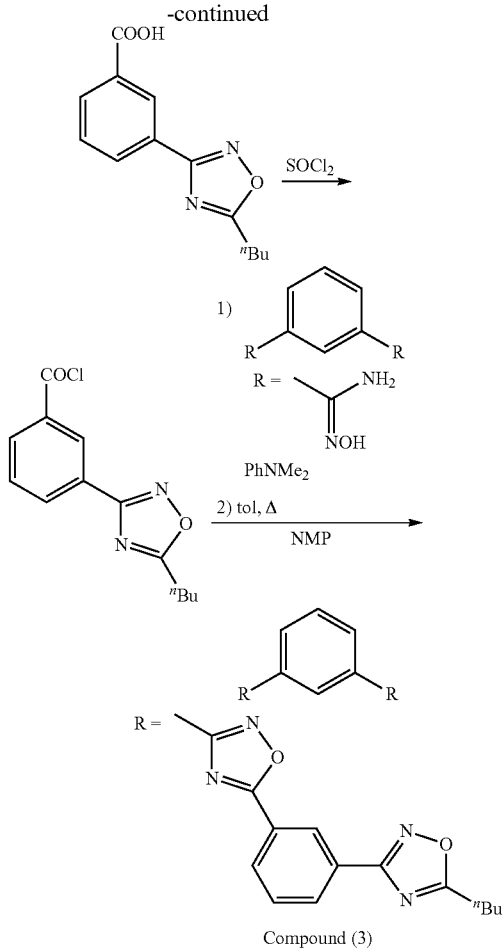

Compound (3)

3-cyano benzoic acid (4.1 g) was added with methanol (50 mL), and was added dropwise with 50% hydroxylamine (6 mL) at 40 degrees Celsius. An hour later, the mixture was neutralized with dilute hydrochloric acid, was filtered, was washed with water, and was dried to give 5 g (99% yield constant) of an amidoxime derivative. After being added with NMP (50 mL) and being cooled with ices, 5 g of the amidoxime derivative was added dropwise with valeric acid chloride (3.4 g), and was added dropwise with N,N-dimethyl aniline (5.3 mL). After being stirred for two hours at the room temperature, the mixture was added with 50 mL of toluene, and then was dehydrated by azeotropy for three hours. After toluene was distilled away, the resultant was poured into dilute hydrochloric acid, was filtered, was washed with water, and then was dried to give 6.5 g (yield constant 96%) of an oxadiazole derivative.

Next, 6.5 g of the oxadiazole derivative and thionyl chloride (3 mL) were reacted in toluene (50 mL) at 60 degrees Celsius for three hours. After toluene was distilled away, 6.8 g (99% yield constant) of an acid chloride derivative was obtained. An NMP solution (50 mL) of Isophthalodiamidoxime (1 g), which was prepared according to the method described in Macromolecules, 1968, 1, 318-324, was added with the obtained acid chloride derivative (3 g) while being cooled with ices, and further was added dropwise with N,N-dimethylaniline (1.8 mL). The mixture was stirred at the room temperature for two hours, then was added with toluene (50 mL) and was dehydrated by azeotropy for three hours. After toluene was distilled away, the resultant was poured into dilute hydrochloric, was filtered, was washed with water, was dried, and was purified according to column chromatography to give 2.4 g (75% yield constant) of a target compound, Compound (3). The identification of the compound was carried out by ¹H-NMR.

¹H-NMR (CDCl₃) δ: 1.01 (6H, t), 1.47~1.60 (4H, m), 1.87~1.98 (4H, m), 3.03 (4H, t), 7.66~7.75 (3H, m), 8.32~8.48 (6H, m), 8.98 (2H, s), 9.07 (1H, s).

The phase transition temperature of the obtained Compound (3) was studied by texture observation of the compound with polarization microscope. Raising the temperature to around 122 degrees Celsius, the phase was changed from the crystal phase to the discotic nematic phase; and further raising the temperature to more than 162 degrees Celsius, the phase was changed to the isotropic liquid phase. That is, from these results, it can be understood that Compound (3) exhibits a discotic nematic phase at a temperature within the range from 122 to 162 degrees Celsius.

Example 4

Synthesis of Compound (4)

Compound (4) was prepared in the manner as shown in the following scheme.

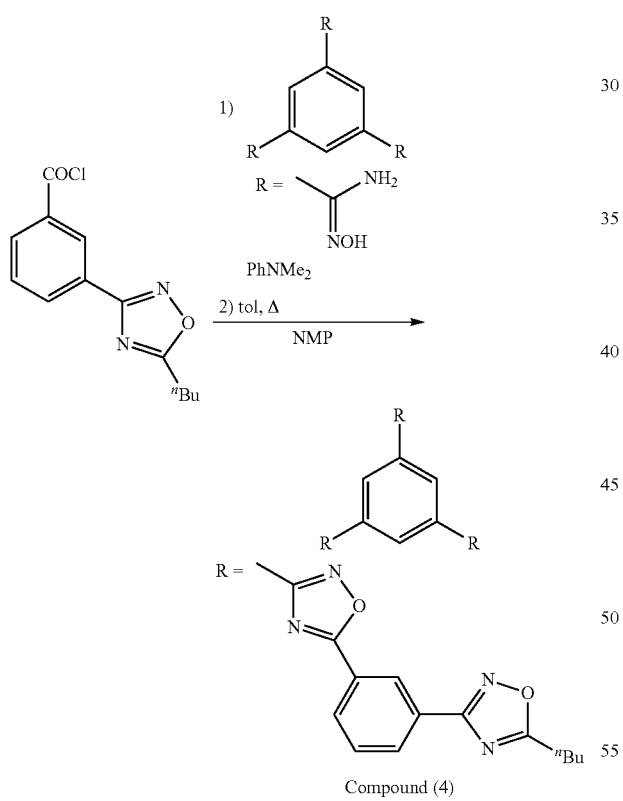

Compound (4)

An NMP solution (30 mL) of triamidoxime derivative (1 g), which was prepared according to the method described in Medical Chemistry, 1972, 15, 1198-1200, was added with an acid chloride derivative (3.5 g) while being cooled with ices, and further was added dropwise with N,N-dimethylaniline (2 mL). The mixture was stirred at the room temperature for two hours, then was added with toluene (30 mL) and was dehydrated by azeotropy for three hours. After toluene was distilled away, the resultant was poured into dilute hydrochloric, was filtered, was washed with water, was dried, and was purified according to column chromatography to give 2.3 g (65% yield constant) of a target compound, Compound (4). The identification of the compound was carried out by ¹H-NMR.

¹H-NMR (CDCl₃) δ: 1.01 (9H, t), 1.43~1.59 (6H, m), 1.87~1.98 (6H, m), 3.05 (6H, t), 7.75 (3H, m), 8.34 (3H, d), 8.45 (3H, d), 8.97 (3H, s), 9.18 (3H, s).

The phase transition temperature of the obtained Compound (4) was studied by texture observation of the compound with polarization microscope. Raising the temperature to around 180 degrees Celsius, the phase was changed from the crystal phase to the discotic nematic phase; and further raising the temperature to more than 259 degrees Celsius, the phase was changed to the isotropic liquid phase. That is, from these results, it can be understood that Compound (4) exhibits a discotic nematic phase at a temperature within the range from 180 to 259 degrees Celsius.

Example 5

Synthesis of Compound (5)

Compound (5) was prepared in the manner as shown in the following scheme.

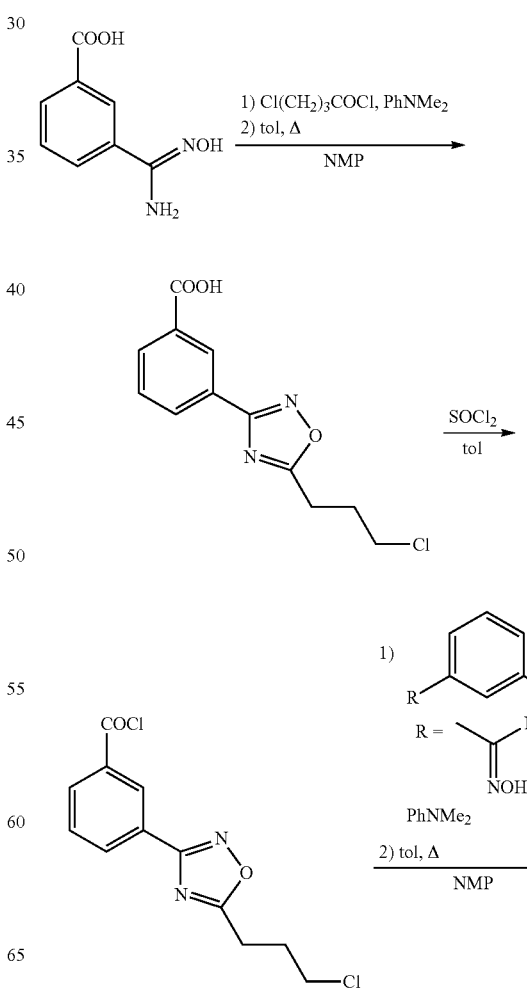

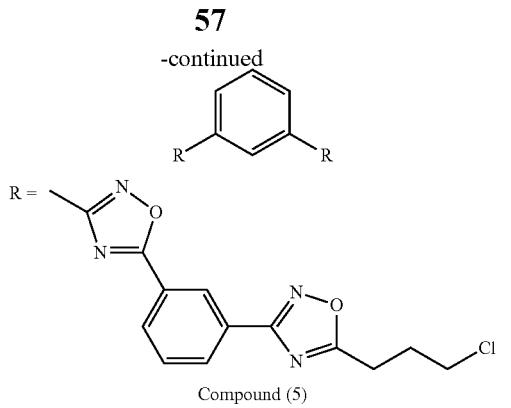

Compound (5)

The amidoxime derivative (10 g), which was prepared in the above-described example, was added with NMP (50 mL) while being cooled with ices, then was added dropwise with 4-chloro butyric acid chloride (6.2 mL), and further added dropwise with N,N-dimethyl aniline (8.5 mL). The mixture was stirred at the room temperature for two hours, then was added with toluene (50 mL) and was dehydrated by azeotropy for three hours. The resultant was added with 400 mL of ethyl acetate, was washed with dilute hydrochloric acid, saturated sodium bicarbonate water and saturated salt solution, and was condensed to give 10.7 g (72% yield constant) of an oxadiazole derivative.

Next, 5.8 g of the oxadiazole derivative and thionyl chloride (3 mL) were reacted in toluene (50 mL) at 60 degrees Celsius for three hours. After toluene was distilled away, 6.2 g (99% yield constant) of an acid chloride derivative was obtained. An NMP solution (50 mL) of Isophthalodiamidoxime (950 mg) was added with the obtained acid chloride derivative (3.1 g) while being cooled with ices, and further was added dropwise with N,N-dimethylaniline (2.1 mL). The mixture was stirred at the room temperature for two hours, then was added with toluene (50 mL) and was dehydrated by azeotropy for three hours. After toluene was distilled away, the resultant was poured into dilute hydrochloric, and was condensed to give 700 mg (22% yield constant) of a target compound, Compound (5). The identification of the compound was carried out by $^1$H-NMR.

$^1$H-NMR (CDCl$_3$) δ: 2.40~2.50 (4H, m), 3.24 (4H, t), 3.77 (4H, t), 7.70~7.80 (3H, m), 8.30~8.45 (6H, m), 8.95 (2H, s), 9.08 (1H, s).

The phase transition temperature of the obtained Compound (5) was studied by texture observation of the compound with polarization microscope. Raising the temperature to around 146 degrees Celsius, the phase was changed from the crystal phase to the discotic nematic phase; and further raising the temperature to more than 178 degrees Celsius, the phase was changed to the isotropic liquid phase. That is, from these results, it can be understood that Compound (5) exhibits a discotic nematic phase at a temperature within the range from 146 to 178 degrees Celsius.

Example 6

Synthesis of Compound (6)

Compound (6) was prepared in the manner as shown in the following scheme.

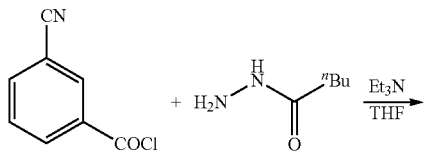

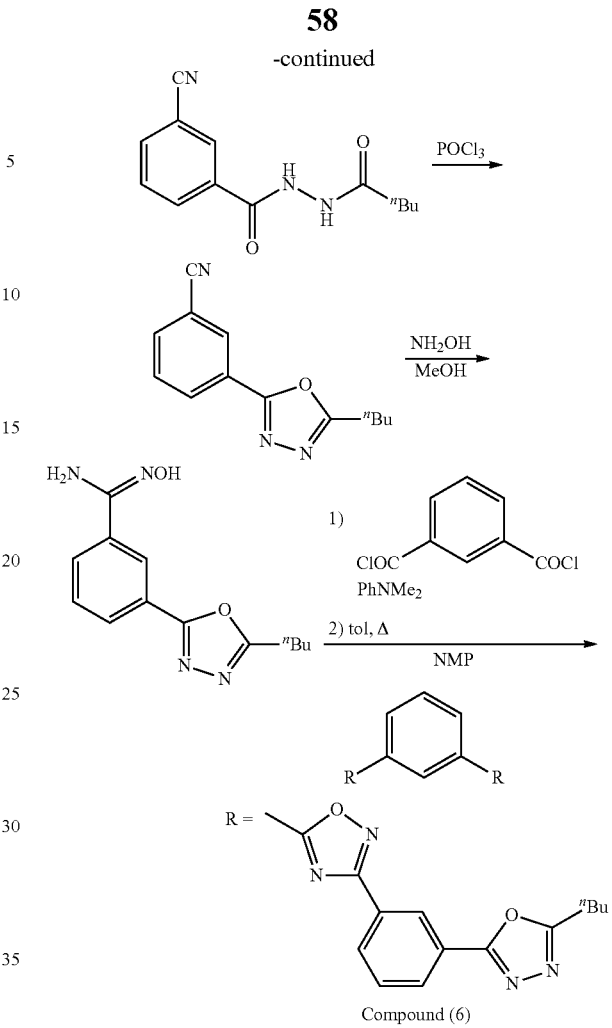

Compound (6)

At first, m-cyano benzoic acid chloride (1.4 g) was added with THF (20 mL), was added with a mixture of THF (15 mL), triethyl amine (1.3 mL) and butyric acid hydrazide (1.0 g), which was prepared according to the method described in J. Med. Chem. 2001, 44, 1268, and was stirred at the room temperature for an hour. The mixture was added with 200 mL of ethyl acetate, was washed with dilute hydrochloric acid, saturated sodium bicarbonate water and saturated salt solution, was dried, and was condensed to give 1.7 g (81% yield constant) of a hydrazine derivative.

The hydrazine derivative (1.7 g) was added with oxy phosphorous chloride (4 mL), and was stirred at 120 degrees Celsius for four hours. The resultant was poured into distilled water (40 mL) and was extracted with ethyl acetate (200 mL). The extract was dried and condensed to give 1.1 g (71% yield constant) of an oxadiazole derivative.

The oxadiazole derivative (1.1 g) was added with methanol (10 mL) and was added dropwise with 50% hydroxylamine (0.6 mL) at 40 degrees Celsius. Two hours later, the resultant was added with distilled water, was filtered, was washed with water and was dried to give 1.1 g (88% yield constant) of an amidoxime derivative.

An NMP solution (3 mL) of the amidoxime derivative (0.52 g) and pyridine (0.12 mL) was added dropwise with acetonitrile solution (0.2 mL) of isophthaloyl dichloride (0.18 g), and was stirred at the room temperature for an hour. After that, the resultant was added with toluene (10 mL) and was dehydrated by azeotropy for three hours. The resultant was added with 100 mL of ethyl acetate, was washed with dilute hydrochloric acid, saturated sodium bicarbonate water and saturated salt solution, and was condensed to give 400 mg (74% yield constant) of a target compound, that is, Compound (6). The identification of the compound was carried out by $^1$H-NMR.

$^1$H-NMR (CDCl$_3$) δ: 1.00 (6H, t), 1.45~1.62 (4H, m), 1.85~1.95 (4H, m), 2.96 (4H, t), 7.68 (2H, t), 7.83 (1H, t), 8.27 (2H, d), 8.42 (2H, d), 8.55 (2H, d), 8.93 (2H, s), 9.12 (1H, s).

The phase transition temperature of the obtained Compound (6) was studied by texture observation of the compound with polarization microscope. Raising the temperature to around 201 degrees Celsius, the phase was changed from the crystal phase to the isotropic liquid phase. Next, gradually decreasing the temperature from 201 degrees Celsius to around 190 degrees Celsius, the phase was changed to the discotic nematic phase. That is, from these results, it can be understood that Compound (6) exhibits a discotic nematic phase as the temperature is decreased.

Comparative Example 1

Synthesis of Comparative Compound 1

Comparative Compound 1 was prepared in the manner as shown in the following scheme.

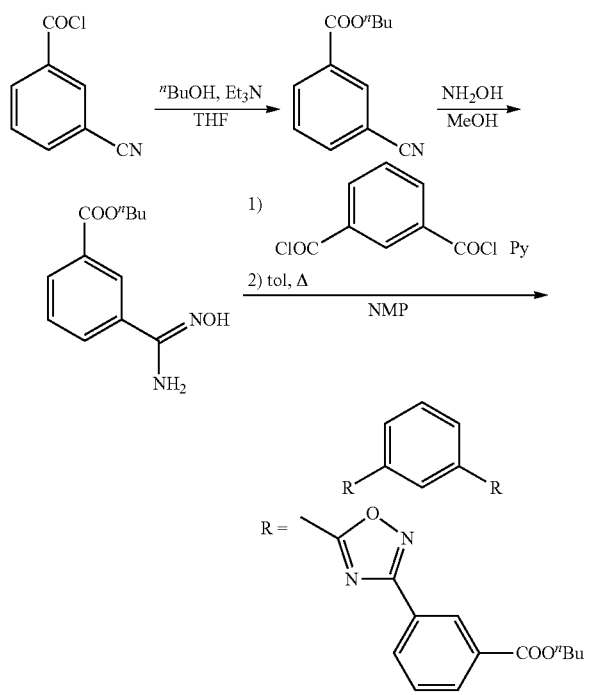

At first, m-cyano benzoic acid chloride (2 g) was added with THF (20 mL), was added with a mixture of THF (15 mL), triethyl amine (2.6 mL) and n-butanol (1.7 mL), and was stirred at the room temperature for two hours. The mixture was added with 200 mL of ethyl acetate, was washed with dilute hydrochloric acid, saturated sodium bicarbonate water and saturated salt solution, was dried, and was condensed to give 2.4 g (96% yield constant) of a butyl ester derivative.

The butyl ester derivative (2.4 g) was added with methanol (50 mL) and was added dropwise with 50% hydroxylamine (1.2 mL) at 40 degrees Celsius. Two hours later, the resultant was added with 400 mL of ethyl acetate, was washed with dilute hydrochloric acid, saturated sodium bicarbonate water and saturated salt solution, was dried, and was condensed to give 2.8 g (99% yield constant) of an amidoxime derivative.

An NMP solution (5 mL) of the amidoxime derivative (1.0 g) and pyridine (0.3 mL) was added dropwise with acetonitrile solution (0.4 mL) of isophthaloyl dichloride (0.39 g), and was stirred at the room temperature for an hour. After that, the resultant was added with toluene (10 mL) and was dehydrated by azeotropy for three hours. The resultant was added with 100 mL of ethyl acetate, was washed with dilute hydrochloric acid, saturated sodium bicarbonate water and saturated salt solution, and was condensed to give 840 mg (77% yield constant) of a target compound, that is, Comparative Compound 1. The identification of the compound was carried out by $^1$H-NMR.

$^1$H-NMR (CDCl$_3$) δ: 1.00 (6H, t), 1.50~1.60 (4H, m), 1.75~1.90 (4H, m), 4.40 (4H, t), 7.66 (2H, t), 7.84 (1H, t), 8.23 (2H, d), 8.44 (2H, d), 8.52 (2H, d), 8.84 (2H, s), 9.12 (1H, s).

The phase transition temperature of the obtained Comparative Compound 1 was studied by texture observation of the compound with polarization microscope. Raising the temperature to around 116 degrees Celsius, the phase was changed from the crystal phase to the discotic nematic phase; and further raising the temperature to more than 131 degrees Celsius, the phase was changed to the isotropic liquid phase. That is, from these results, it can be understood that Comparative Compound 1 exhibits a discotic nematic phase at a temperature within the range from 116 to 131 degrees Celsius.

Comparative Example 2

Synthesis of Comparative Compound 2

Comparative Compound 2 was prepared in the manner as shown in the following scheme.

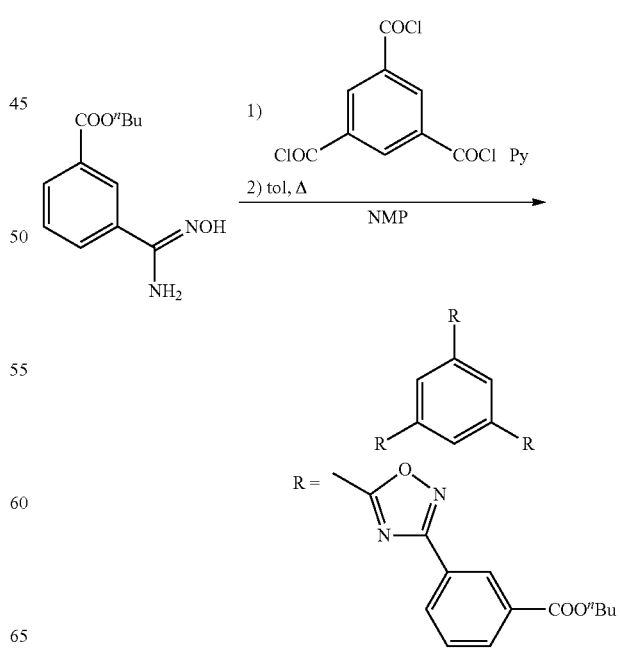

An NMP solution (5 mL) of the amidoxime derivative (1.0 g), which was prepared in Comparative Example 1, and pyridine (0.3 mL) was added dropwise with acetonitrile solution (0.4 mL) of trimesic acid chloride (0.35 g), and was stirred at the room temperature for an hour. After that, the resultant was added with toluene (10 mL) and was dehydrated by azeotropy for three hours. The resultant was added with 100 mL of ethyl acetate, was washed with dilute hydrochloric acid, saturated sodium bicarbonate water and saturated salt solution, and was condensed to give 840 mg (77% yield constant) of a target compound, that is, Comparative Compound 2. The identification of the compound was carried out by $^1$H-NMR.

$^1$H-NMR (CDCl$_3$) δ: 1.01 (9H, t), 1.50~1.65 (6H, m), 1.80~1.90 (6H, m), 4.42 (6H, t), 7.68 (3H, t), 8.28 (3H, d), 8.48 (3H, d), 8.85 (3H, s), 9.28 (3H, s).

The phase transition temperature of the obtained Comparative Compound 2 was studied by texture observation of the compound with polarization microscope. Raising the temperature to around 145 degrees Celsius, the phase was changed from the crystal phase to the discotic nematic phase; and further raising the temperature to more than 228 degrees Celsius, the phase was changed to the isotropic liquid phase. That is, from these results, it can be understood that Comparative Compound 2 exhibits a discotic nematic phase at a temperature within the range from 145 to 228 degrees Celsius.

Comparative Example 3

Synthesis of Comparative Compound 3

Comparative Compound 3 was prepared in the manner as shown in the following scheme.

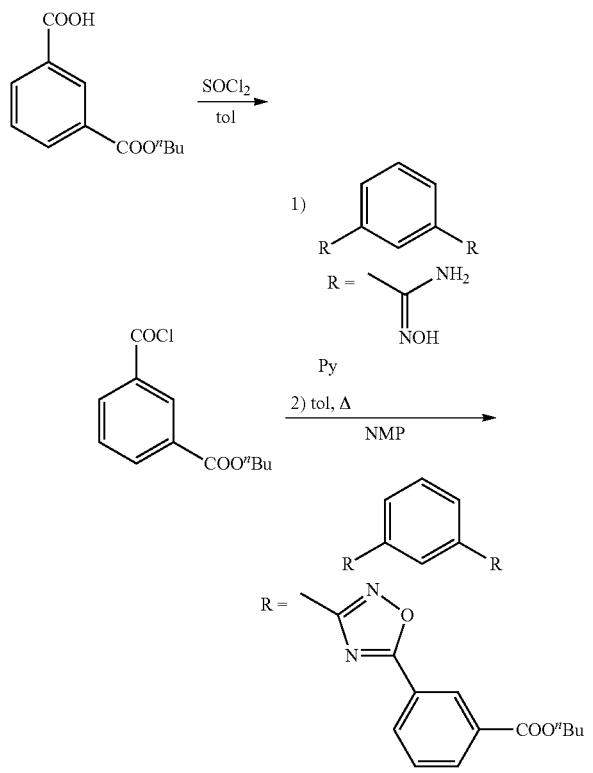

Monobutyl Isophthalate (3 g), which was prepared according to the method described in Chem. Europ. J. 2005, 11, 3591, and thionyl chloride (2.4 mL) were reacted in toluene (50 mL) at 60 degrees Celsius for three hours. After toluene was distilled away, 3.3 g (99% yield constant) of an acid chloride derivative was obtained.

An NMP solution (10 mL) of Isophthalodiamidoxime (0.6 g) was added dropwise with the obtained acid chloride derivative (1.7 g) while being cooled with ices, further was added dropwise with pyridine (0.6 mL), was stirred at the room temperature for two hours, then was added with toluene (50 mL), and was dehydrated by azeotropy for three hours. After toluene was distilled away, the resultant was poured into dilute hydrochloric, was filtered, was washed with water, was dried, and was purified according to column chromatography to give 1.6 g (90% yield constant) of a target compound, Comparative Compound 3. The identification of the compound was carried out by $^1$H-NMR.

$^1$H-NMR (CDCl$_3$) δ: 1.02 (6H, t), 1.50~1.60 (4H, m), 1.80~1.95 (4H, m), 7.65~7.75 (3H, m), 7.33 (2H, d), 7.38 (2H, d), 8.48 (2H, d), 8.87 (2H, s), 9.15 (1H, s).

The phase transition temperature of the obtained Comparative Compound 3 was studied by texture observation of the compound with polarization microscope. Raising the temperature to around 126 degrees Celsius, the phase was changed from the crystal phase to the discotic nematic phase; and further raising the temperature to more than 127 degrees Celsius, the phase was changed to the isotropic liquid phase. That is, from these results, it can be understood that Comparative Compound 3 exhibits a discotic nematic phase at a temperature within the range from 126 to 127 degrees Celsius.

Comparative Example 4

Synthesis of Comparative Compound 4

Comparative Compound 4 was prepared in the manner as shown in the following scheme.

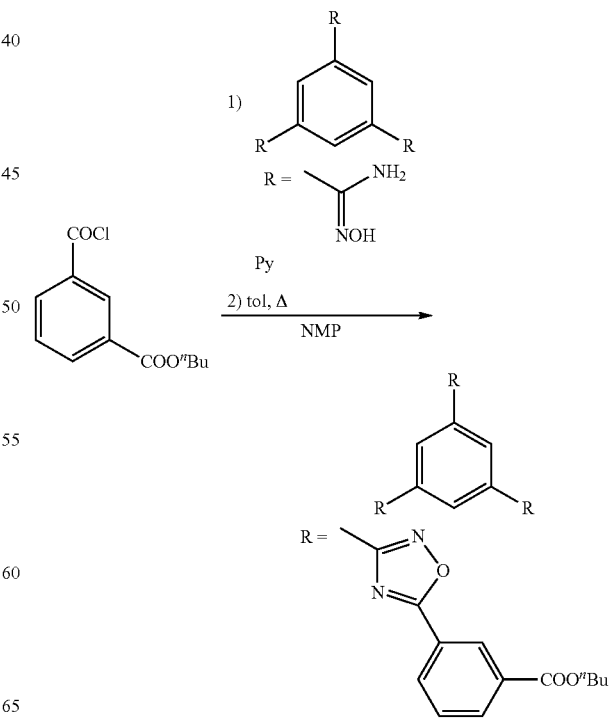

An NMP solution (10 mL) of triamidoxime (530 mg) was added dropwise with the acid chloride derivative (1.7 g), which was obtained in Comparative Example 3, while being cooled with ices, further was added dropwise with pyridine (0.6 mL). The resultant was stirred at the room temperature for two hours, then was added with toluene (50 mL), and was dehydrated by azeotropy for three hours. The resultant was poured into dilute hydrochloric, was filtered, was washed with water, and was dried to give 1.4 g (85% yield constant) of a target compound, Comparative Compound 4. The identification of the compound was carried out by $^1$H-NMR.

$^1$H-NMR (CDCl$_3$) δ: 1.01 (9H, t), 1.50~1.60 (6H, m), 1.80~1.90 (6H, m), 4.45 (6H, t), 7.70 (3H, t), 8.32 (3H, d), 8.52 (3H, d), 8.95 (3H, s), 9.18 (3H, s).

The phase transition temperature of the obtained Comparative Compound 4 was studied by texture observation of the compound with polarization microscope. Raising the temperature to around 148 degrees Celsius, the phase was changed from the crystal phase to the discotic nematic phase; and further raising the temperature to more than 224 degrees Celsius, the phase was changed to the isotropic liquid phase. That is, from these results, it can be understood that Comparative Compound 4 exhibits a discotic nematic phase at a temperature within the range from 148 to 224 degrees Celsius.

Regarding the obtained compounds of formula (1) and the obtained comparative compounds, the obtained data are summarized in the following table.

TABLE 1

| | Compound | Cry→ND*1 (degrees Celsius) | ND→Iso*2 (degrees Celsius) | Temperature Range of ND phase (degrees Celsius) |
|---|---|---|---|---|
| Examples of Invention | Compound (1) | 130 | 164 | 34 |
| | Compound (3) | 122 | 162 | 40 |
| | Compound (5) | 146 | 178 | 32 |
| Comparative Examples | Comparative Compound 1 | 116 | 131 | 15 |
| | Comparative Compound 3 | 126 | 127 | 1 |

*1: the phase transition temperature from a crystal phase to a discotic nematic phase
*2: the phase transition temperature from a discotic nematic phase to an isotropic phase

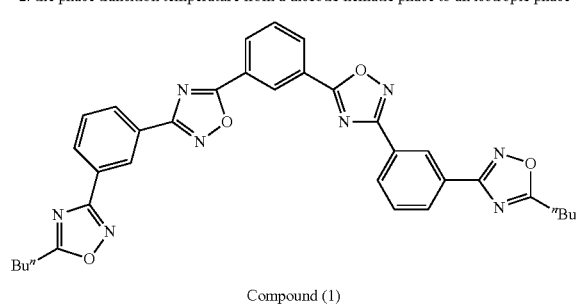

Compound (1)

TABLE 1-continued

| | Cry→ND*1 (degrees Celsius) | ND→Iso*2 (degrees Celsius) | Temperature Range of ND phase (degrees Celsius) |
|---|---|---|---|
| Compound | | | |

Compound (3)

Compound (5)

Comparative Compound 1

Comparative Compound 3

TABLE 2

| | Compound | Cry→ND*1 (degrees Celsius) | ND→Iso*2 (degrees Celsius) | Temperature Range of ND phase (degrees Celsius) |
|---|---|---|---|---|
| Examples of Invention | Compound (2) | 210 | 268 | 58 |
| | Compound (4) | 180 | 259 | 79 |

TABLE 2-continued

| Compound | | Cry→ND*1 (degrees Celsius) | ND→Iso*2 (degrees Celsius) | Temperature Range of ND phase (degrees Celsius) |
|---|---|---|---|---|
| Comparative Examples | Comparative Compound 2 | 145 | 228 | 83 |
| | Comparative Compound 4 | 148 | 224 | 76 |

*1: the phase transition temperature from a crystal phase to a discotic nematic phase
*2: the phase transition temperature from a discotic nematic phase to an isotropic phase Compound (2)

Compound (4)

Comparative Compound 2

Comparative Compound 4

Next, some examples of producing the compounds having any polymerizable group(s) are described below.

Example 7

Synthesis of Compound (7)

Compound (7) was prepared in the manner as shown in the following scheme.

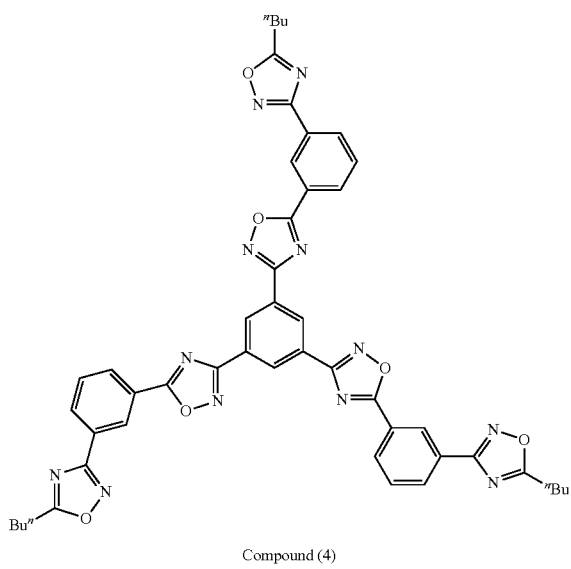

-continued

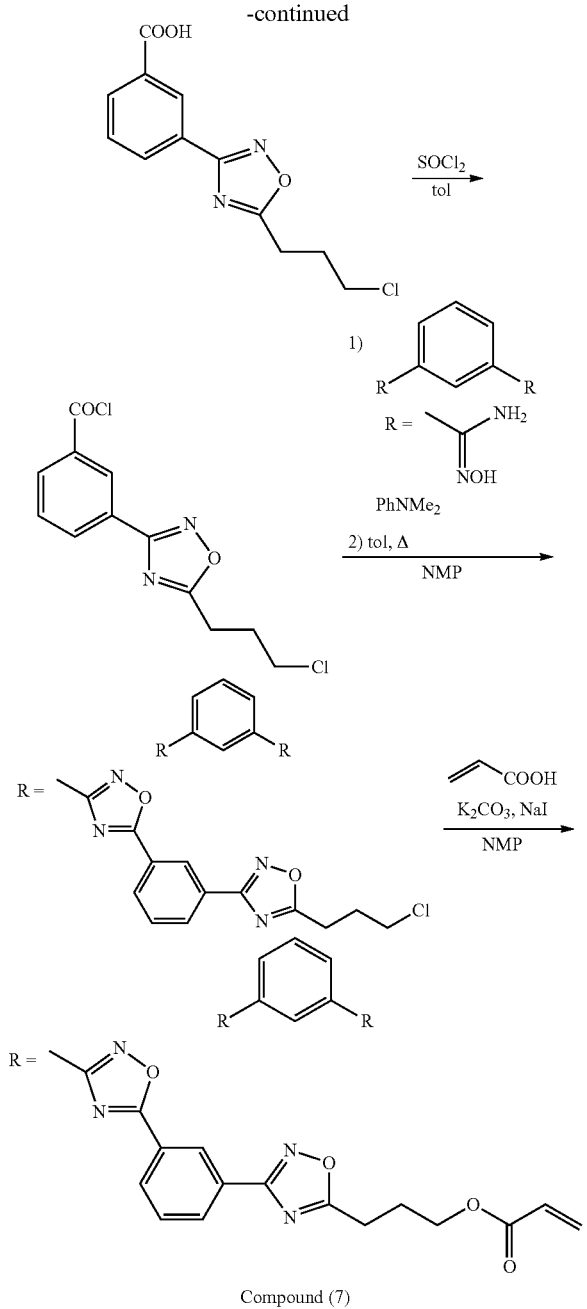

Compound (7)

3-cyano benzoic acid (8.2 g) was added with methanol (100 mL), and was added dropwise with 50% hydroxylamine (12 mL) at 40 degrees Celsius. An hour later, the mixture was neutralized with dilute hydrochloric acid, was filtered, was washed with water, and was dried to give 10 g (99% yield constant) of an amidoxime derivative. After being added with NMP (50 mL) and being cooled with ices, 10 g of the amidoxime derivative was added dropwise with 4-chlorobutyric acid chloride (6.2 mL), and was added dropwise with N,N-dimethyl aniline (8.5 mL). After being stirred for two hours at the room temperature, the mixture was added with 50 mL of toluene, and then was dehydrated by azeotropy for three hours. The resultant was added with 400 mL of ethyl acetate, was washed with water, and then was condensed to give 10.7 g (yield constant 72%) of an oxadiazole derivative.

Next, 5.8 g of the oxadiazole derivative and thionyl chloride (3 mL) were reacted in toluene (50 mL) at 60 degrees Celsius for three hours. After toluene was distilled away, 6.2 g (99% yield constant) of an acid chloride derivative was obtained. An NMP solution (50 mL) of Isophthalodiamidoxime (950 mg) was added with the obtained acid chloride derivative (3 g) while being cooled with ices, and further was added dropwise with N,N'-dimethylaniline (2.1 mL). The mixture was stirred at the room temperature for two hours, then was added with toluene (50 mL) and was dehydrated by azeotropy for three hours. The resultant was added with 400 mL of ethyl acetate, was washed with water, and then was condensed to give 700 mg of a dichloride derivative. To the dichloride derivative (700 mg), NMP (10 mL), potassium carbonate (610 mg), acrylic acid (320 mg), sodium Iodide (330 mg) and "IRGANOX1010" (20 mg), provided by Ciba-Geigy, and was stirred at 85 degrees Celsius for three hours. The resultant was poured into dilute hydrochloric, was filtered, was washed with water, was dried, and was purified according to column chromatography to give 690 mg (86% yield constant) of a target compound, that is, Compound (7). The identification of the compound was carried out by $^1$H-NMR.

$^1$H-NMR (CDCl$_3$) δ: 2.30~2.40 (4H, m), 3.13 (4H, t), 4.35 (4H, t), 5.82 (2H, d), 6.13 (2H, dd), 6.42 (2H, d), 7.70~7.80 (3H, m), 8.30~8.50 (6H, m), 8.95 (2H, s), 9.05 (1H, s).

The phase transition temperature of the obtained Compound (7) was studied by texture observation of the compound with polarization microscope. Raising the temperature to around 121 degrees Celsius, the phase was changed from the crystal phase to the discotic nematic phase; and further raising the temperature to more than 140 degrees Celsius, the phase was changed to the isotropic liquid phase. That is, from these results, it can be understood that Compound (7) exhibits a discotic nematic phase at a temperature within the range from 121 to 140 degrees Celsius.

Example 8

Synthesis of Compound (8)

Compound (8) was prepared in the same manner as described above.

Compound (8)

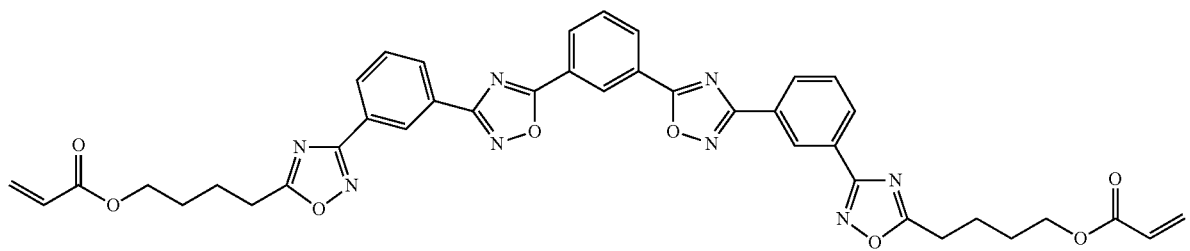

molecular weight: 754.75

The identification of the compound was carried out by ¹H-NMR.

¹H-NMR (CDCl₃) δ: 1.82~1.92 (4H, m), 2.04~2.11 (4H, m), 3.07 (4H, t), 4.25 (4H, t), 5.82 (2H, d), 6.13 (2H, dd), 6.42 (2H, d), 7.65~7.75 (3H, m), 8.30~8.50 (6H, m), 8.95 (2H, s), 9.05 (1H, s).

The phase transition temperature of the obtained Compound (8) was studied by texture observation of the compound with polarization microscope. Raising the temperature to around 106 degrees Celsius, the phase was changed from the crystal phase to the discotic nematic phase; and further raising the temperature to more than 129 degrees Celsius, the phase was changed to the isotropic liquid phase. That is, from these results, it can be understood that Compound (8) exhibits a discotic nematic phase at a temperature within the range from 106 to 129 degrees Celsius.

Example 9

Synthesis of Compound (9)

Compound (9) was prepared in the manner as shown in the following scheme.

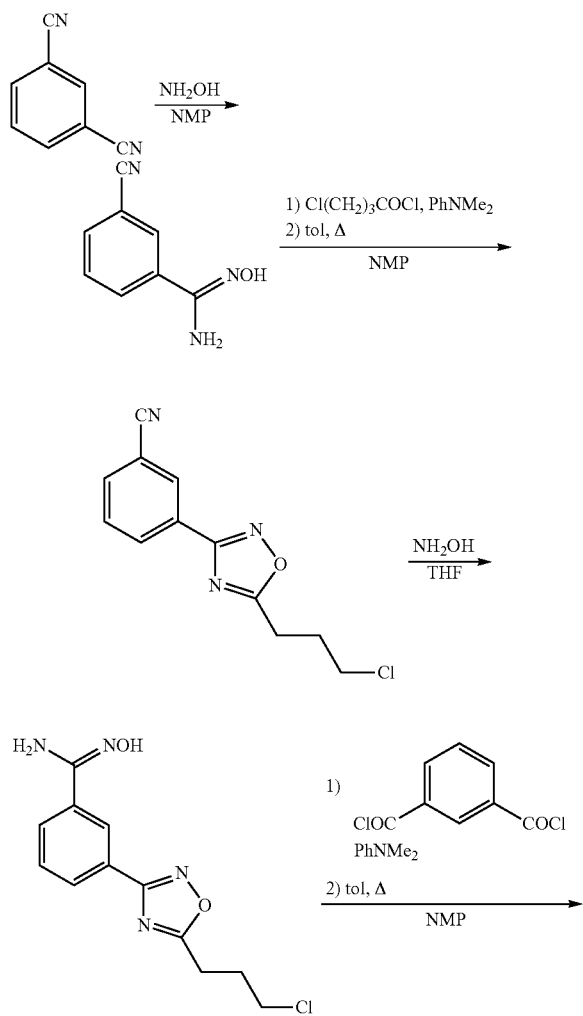

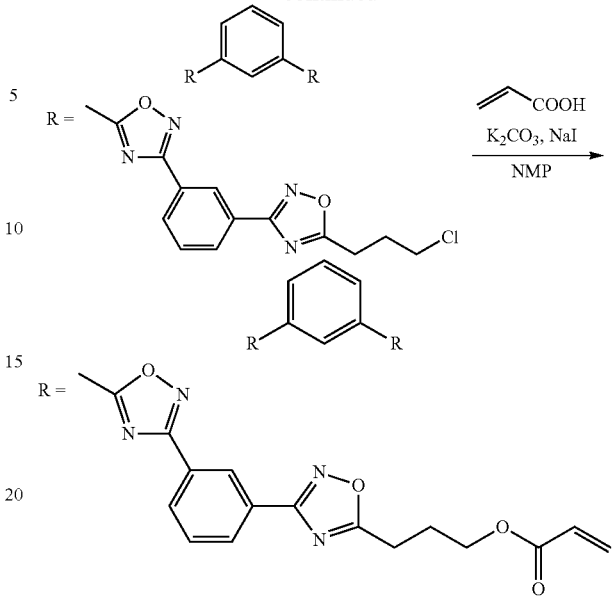

Compound (9)

Isophthalonitrile (5.12 g) was added to NMP (20 mL). The mixture was added dropwise with 50% hydroxylamine (2.64 g) at 40 degrees Celsius. After being stirred at 50 degrees Celsius for four hours, the mixture was added with 100 mL of ethyl acetate, was washed with water, was dried with magnesium sulfate to give an ethyl acetate solution containing monoamidoxime derivative. The solution was added dropwise with 4-chlorobutyric acid chloride (3.7 g) while being cooled with ices, and further was added dropwise with N,N-dimethylaniline (3.7 mL). After being stirred at the room temperature for two hours, the mixture was added with a mixture of NMP (50 mL) and toluene (50 mL), and then was dehydrated by azeotropy for three hours. The resultant was added with 400 mL of ethyl acetate, was washed with dilute hydrochloric acid, saturated sodium bicarbonate water and saturated salt solution, was condensed, and was purified according to column chromatography to give 4.5 g (45% yield constant) of a oxadiazole derivative. The oxadiazole derivative (4.5 g) was added with THF (20 mL), was added dropwise with 50% hydroxylamine (1.2 g), was stirred for four hours, was added with 100 mL of ethyl acetate, and was washed with saturated salt solution to give an ethyl acetate layer. The ethyl acetate layer was purified according to column chromatography to give 4.5 g (88% yield constant) of an amidoxime derivative. The amidoxime derivative (4.5 g) was added with NEP (50 mL), was added dropwise with an ethyl acetate solution (10 mL) of isophthalic acid chloride (1.5 g) while being cooled with ices, and was further added dropwise with N,N-dimethyl aniline (2.3 mL). After being stirred at the room temperature for two hours, the mixture was added with toluene (50 mL), and was dehydrated by azeotropy for three hours. The resultant was added with 400 mL of ethyl acetate, and was washed with dilute hydrochloric acid, saturated sodium bicarbonate water and saturated salt solution, and was condensed to give 4.1 g of a dichloride derivative. To the dichloride derivative (700 mg), NMP (10 mL), potassium carbonate (610 mg), acrylic acid (320 mg), sodium Iodide (330 mg) and "IRGANOX1010" (20 mg), provided by Ciba-Geigy, and was stirred at 85 degrees Celsius for three hours. The resultant was poured into dilute hydrochloric, was filtered, was washed with water, was dried, and was purified according to column chromatography to give 714 mg (89% yield constant) of a target compound, that is, Compound (9). The identification of the compound was carried out by $^1$H-NMR.

$^1$H-NMR (CDCl$_3$) δ: 2.30~38 (4H, m), 3.13 (4H, t), 4.38 (4H, t), 5.82 (2H, d), 6.13 (2H, dd), 6.42 (2H, d), 7.69 (2H, t), 7.85 (1H, t), 8.28 (2H, d), 8.38 (2H, d), 8.51 (2H, d), 8.92 (2H, s), 9.13 (1H, s).

The phase transition temperature of the obtained Compound (9) was studied by texture observation of the compound with polarization microscope. Raising the temperature to around 128 degrees Celsius, the phase was changed from the crystal phase to the discotic nematic phase; and further raising the temperature to more than 141 degrees Celsius, the phase was changed to the isotropic liquid phase. That is, from these results, it can be understood that Compound (9) exhibits a discotic nematic phase at a temperature within the range from 128 to 141 degrees Celsius.

Example 10

Synthesis of Compound (10)

Compound (10) was prepared in the same manner as described above.

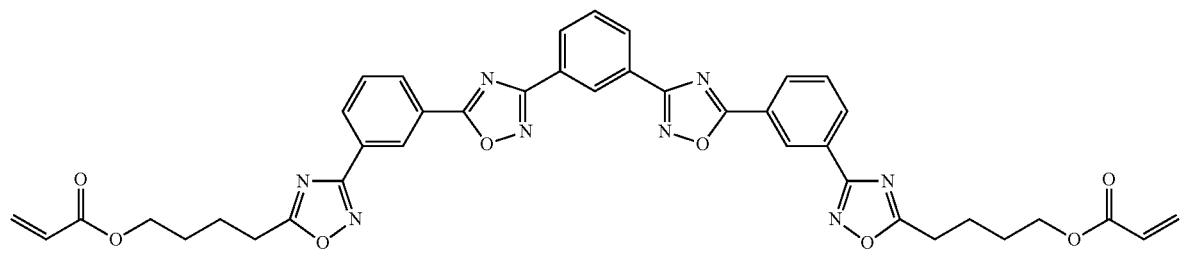

Compound (10)

molecular weight: 754.75

The identification of the compound was carried out by $^1$H-NMR.

$^1$H-NMR (CDCl$_3$) δ: 1.85~1.92 (4H, m), 2.02~2.11 (4H, m), 3.07 (4H, t), 4.25 (4H, t), 5.82 (2H, d), 6.13 (2H, dd), 6.42 (2H, d), 7.69 (2H, t), 7.83 (1H, t), 8.30 (2H, d), 8.41 (2H, d), 8.55 (2H, d), 8.92 (2H, s), 9.13 (1H, s).

The phase transition temperature of the obtained Compound (10) was studied by texture observation of the compound with polarization microscope. Raising the temperature to around 114 degrees Celsius, the phase was changed from the crystal phase to the discotic nematic phase; and further raising the temperature to more than 128 degrees Celsius, the phase was changed to the isotropic liquid phase. That is, from these results, it can be understood that Compound (10) exhibits a discotic nematic phase at a temperature within the range from 114 to 128 degrees Celsius.

Example 11

Synthesis of Compound (11)

Compound (11) was prepared in the manner as shown in the following scheme.

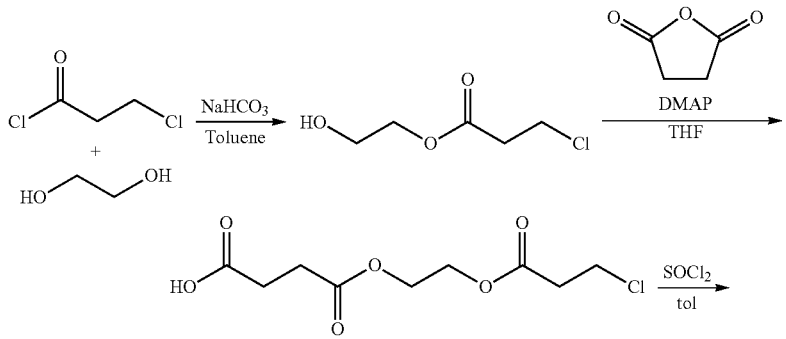

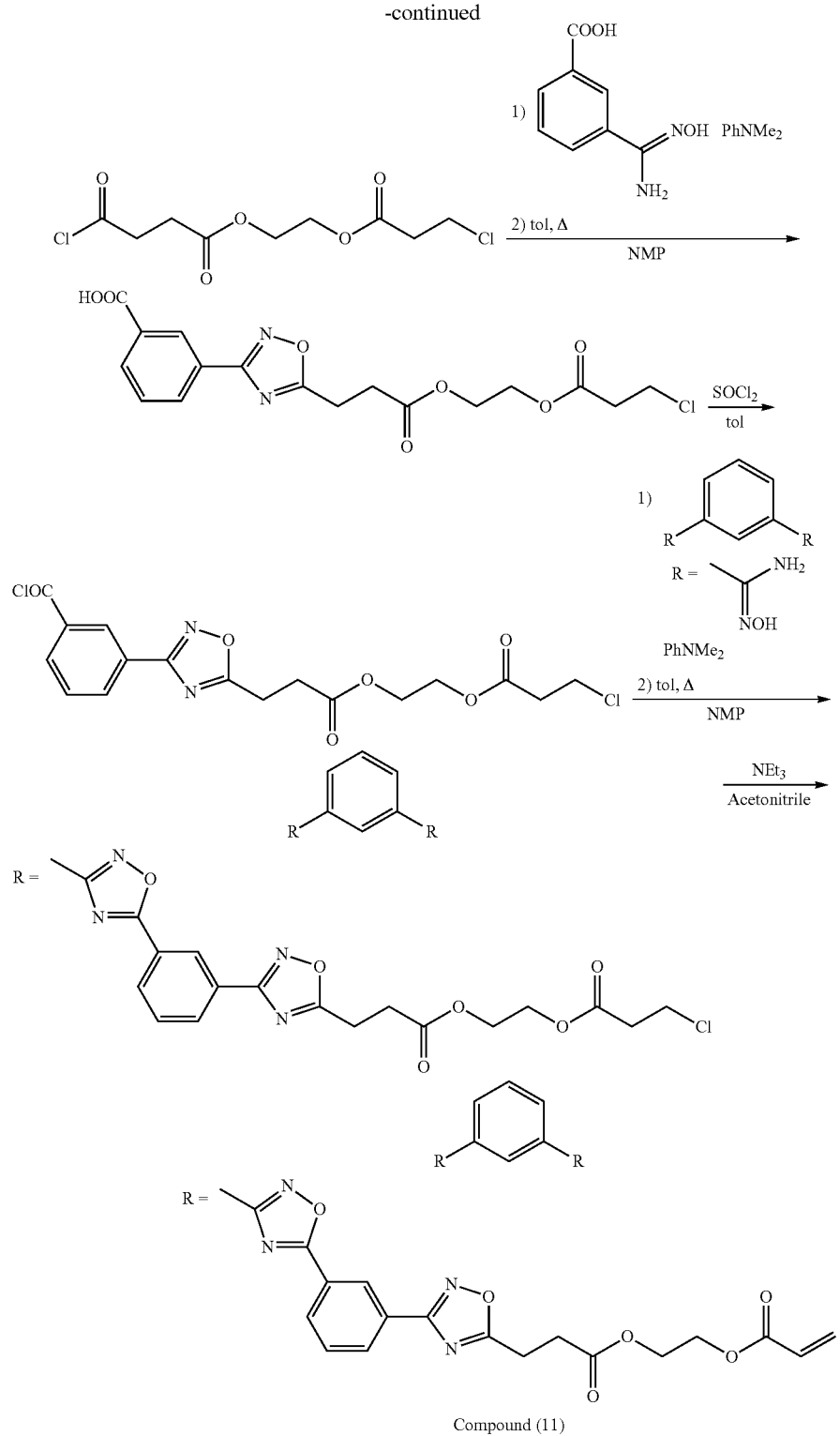

Compound (11)

1,2-ethane diol (12.4 g) was added with sodium hydrogen carbonate (21 g), and was added dropwise with 3-chloro propionic acid chloride (25.4 g) while being cooled with ices. After being stirred at 25 degrees Celsius for three hours, the resultant was purified according to column chromatography to give about 200 g of a mixture containing a half alcohol derivative. The mixture (20 g), containing the half alcohol derivative, was added with THF (100 mL) and succinic acid anhydrate (11.5 g), was added dropwise with pyridine (10.2 mL) while being cooled with ices, and then was stirred at a temperature for two hours. After that, the reactant was added with ethyl acetate (200 mL), was washed with dilute hydrochloric acid, and then was extracted inversely with saturated sodium hydrogen carbonate. Furthermore, the water layer was acidified with dilute hydrochloric acid, was extracted with ethyl acetate, was dried and was condensed to give 20.4 g (40% yield constant) of a half carboxylic acid derivative.

The half carboxylic acid derivative (20.4 g) was added with toluene (100 mL) and thionyl chloride (8.8 mL), and was condensed under heat at 100 degrees Celsius for two hours to give an acid chloride derivative. The acid chloride derivative was added dropwise to a mixed liquid of the amidoxime derivative (14.6 g), NMP (100 mL) and N,N-dimethylaniline (15.4 mL) while being cooled with ices, and then was stirred at the room temperature for two hours. After that, the resultant was added with toluene (100 mL), and was heated at 120 degrees Celsius for two hours. After that, the resultant was added with ethyl acetate (400 mL), was washed with dilute hydrochloric acid and saturated salt solution, was dried, and then was purified according to column chromatography to give 15 g (47% yield constant) of an oxadiazole derivative.

The oxadiazole derivative (3.5 g) was added with toluene (50 mL) and thionyl chloride (1 mL), and was condensed under heat at 100 degrees Celsius for two hours to give an acid chloride derivative. The acid chloride derivative was added dropwise to a mixed liquid of the diamidoxime derivative (850 mg), NMP (50 mL) and N,N-dimethylaniline (1.7 mL) while being cooled with ices, and then was stirred at the room temperature for two hours. After that, the resultant was added with toluene (50 mL), and was stirred under the azeotropy-dehydrate condition for two hours. After being cooled, toluene was distilled away, and the resultant was added with acetonitrile (20 mL) and triethyl amine (1.8 mL), and was stirred at 60 degrees Celsius for two hours. After that, the resultant was added with ethyl acetate (400 mL), was washed with dilute hydrochloric acid and saturated salt solution, was dried, and then was purified according to column chromatography to give 15 g (47% yield constant) of an oxadiazole derivative. After being cooled, the resultant was added with ethyl acetate (200 mL), was washed with dilute hydrochloric acid and saturated salt solution, was dried, and then was purified according to column chromatography to give 1.4 g (35% yield constant) of a target compound, that is, Compound (11). The identification of the compound was carried out by $^1$H-NMR.

$^1$H-NMR (CDCl$_3$) δ: 3.13 (4H, t), 3.35 (4H, t), 4.38~4.48 (8H, m), 5.82 (2H, d), 6.13 (2H, dd), 6.42 (2H, d), 7.65~7.80 (3H, m), 8.30~8.50 (6H, m), 8.95 (2H, s), 9.05 (1H, s).

The phase transition temperature of the obtained Compound (11) was studied by texture observation of the compound with polarization microscope. Raising the temperature to around 91 degrees Celsius, the phase was changed from the crystal phase to the discotic nematic phase; and further raising the temperature to more than 108 degrees Celsius, the phase was changed to the isotropic liquid phase. That is, from these results, it can be understood that Compound (11) exhibits a discotic nematic phase at a temperature within the range from 91 to 108 degrees Celsius.

Example 12

Synthesis No. 1 of Compound (12)

Compound (12) was prepared in the manner as shown in the following scheme.

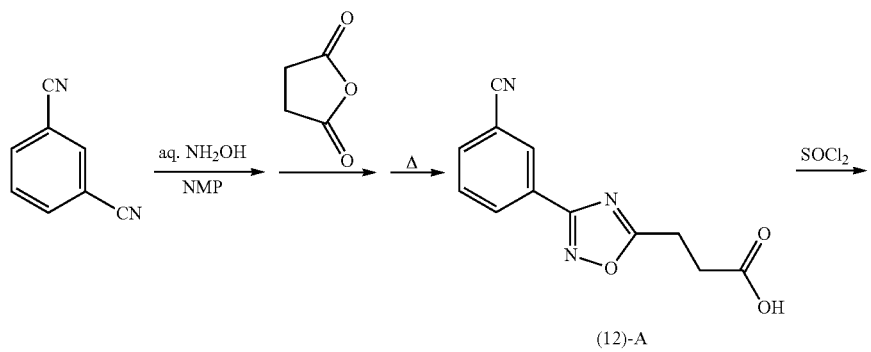

(12)-A

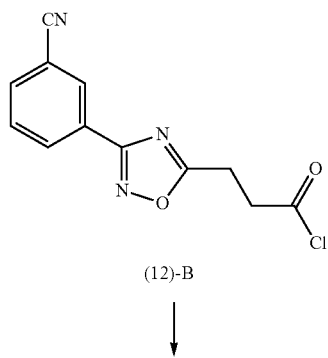

(12)-B

-continued
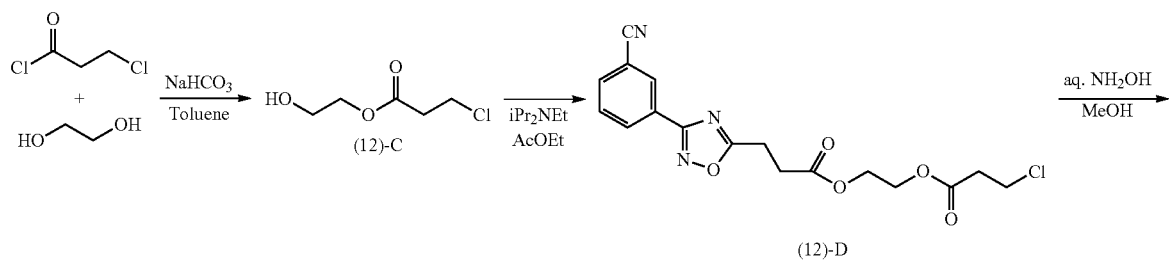
(12)-C
(12)-D
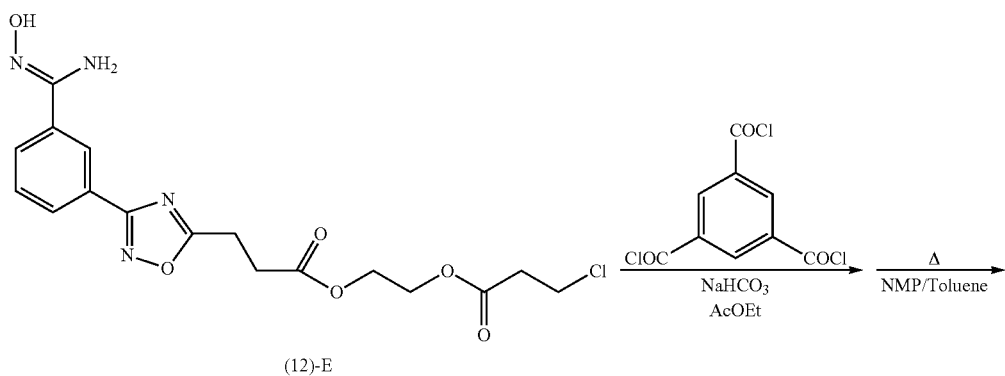
(12)-E
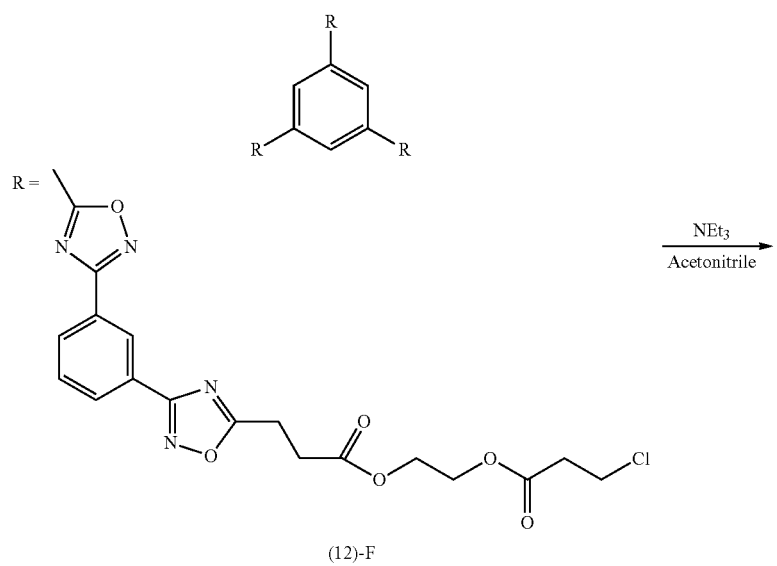
(12)-F

-continued

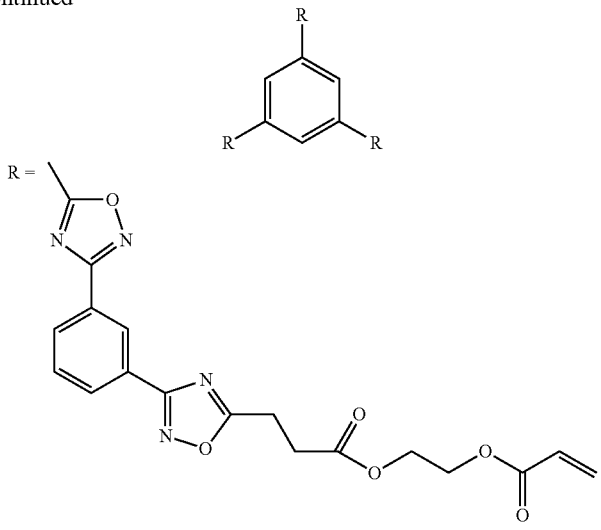

Compound (12)

Isophthalonitrile (5.12 g) was added to NMP (20 mL). The mixture was added dropwise with 50% hydroxylamine (2.42 g) at 40 degrees Celsius. After being stirred at 50 degrees Celsius for four hours, the mixture was added with succinic acid anhydride (4.41 g) fractionally, and then was stirred under heat at 120 degrees Celsius for five hours. After being cooled, the resultant was added with 100 mL of ethyl acetate, was washed with water, and was extracted with an aqueous solution of potassium carbonate (5.56 g) to give a water layer. The water layer was neutralized with hydrochloric acid, and was extracted with 100 mL of ethyl acetate. The ethyl acetate layer was washed with water, was dried, and condensed to give about 6.8 g of a solid mixture containing Compound (12)-A.

1,2-ethane diol (12.4 g) was added with sodium hydrogen carbonate (21.0 g), and was added dropwise with 3-chloro propionic acid chloride (25.4 g) while being cooled with ices. After being stirred at 25 degrees Celsius for three hours, the resultant was purified according to column chromatography to give 17.5 g of Compound (12)-C.

The mixture (5.2 g) containing Compound (12)-A was added with toluene (10 mL), DMF (10 mg) and thionyl chloride (2.6 mL), and was stirred for two hours at 50 degrees Celsius. After being cooled, excess thionyl chloride and toluene were distilled away, thereby giving a mixture containing Compound (12)-B. The mixture containing Compound (12)-B was added with ethyl acetate (100 mL) and Compound (12)-C (3.6 g), and was added dropwise with diisopropyl ethyl amine (5.3 mL). After being stirred at 25 degrees Celsius for an hour, the resultant was washed with dilute hydrochloric acid and saturated salt aqueous solution, was dried, and then was condensed to give a mixture containing Compound (12)-D. The mixture was purified according to column chromatography to give 7.1 g of Compound (12)-D.

Compound (12)-D (7.1 g) was added with methanol (20 mL), and was added dropwise with 50% hydroxylamine (1.9 g) at 40 degrees Celsius. After being stirred for four hours, the resultant was added with 100 mL of ethyl acetate, and was washed with saturated salt aqueous solution to give an ethyl acetate layer. The ethyl acetate layer was purified according to column chromatography to give 6.6 g (85% yield constant) of Compound (12)-E.

Compound (12)-E (6.6 g) was added with ethyl acetate (70 mL) and 70 mL of an aqueous solution of sodium hydrogen carbonate (1.5 g), and was added dropwise with toluene solution (5 mL) of trimesic acid chloride (1.2 g). After being stirred at the room temperature for three hours, the resultant was added with hexane (200 mL), thereby giving a crystal via filtration. The obtained crystal was added with NMP (20 mL) and toluene (20 mL), and was stirred under the azeotropy-dehydrate condition for two hours. After being cooled, toluene was distilled away, and the resultant was added with acetonitrile (20 ml) and triethylamine (3.0 mL), and was stirred at 60 degrees Celsius for two hours. After being cooled, the resultant was added with ethyl acetate (100 mL), was washed with dilute hydrochloric acid and saturated salt aqueous solution, was dried, and then was condensed to give Compound (12) as a crude product. The crude product was purified according to column chromatography to give 4.7 g (84% yield constant) of a target compound, that is, Compound (12). The identification of the compound was carried out by $^1$H-NMR.

$^1$H-NMR (CDCl$_3$) δ: 3.04 (6H, t), 3.33 (6H, t), 4.35~4.50 (12H, m), 5.82 (3H, d), 6.12 (3H, dd), 6.47 (3H, d), 7.70 (3H, t), 8.27 (3H, d), 8.43 (3H, d), 8.93 (3H, s), 9.30 (3H, s).

The phase transition temperature of the obtained Compound (12) was studied by texture observation of the compound with polarization microscope. Raising the temperature to around 74 degrees Celsius, the phase was changed from the crystal phase to the discotic nematic phase; and further raising the temperature to more than 170 degrees Celsius, the phase was changed to the isotropic liquid phase. That is, from these results, it can be understood that Compound (12) exhibits a discotic nematic phase at a temperature within the range from 74 to 170 degrees Celsius.

Example 13

Synthesis No. 2 of Compound (12)

Compound (12) was prepared in the manner as shown in the following scheme.

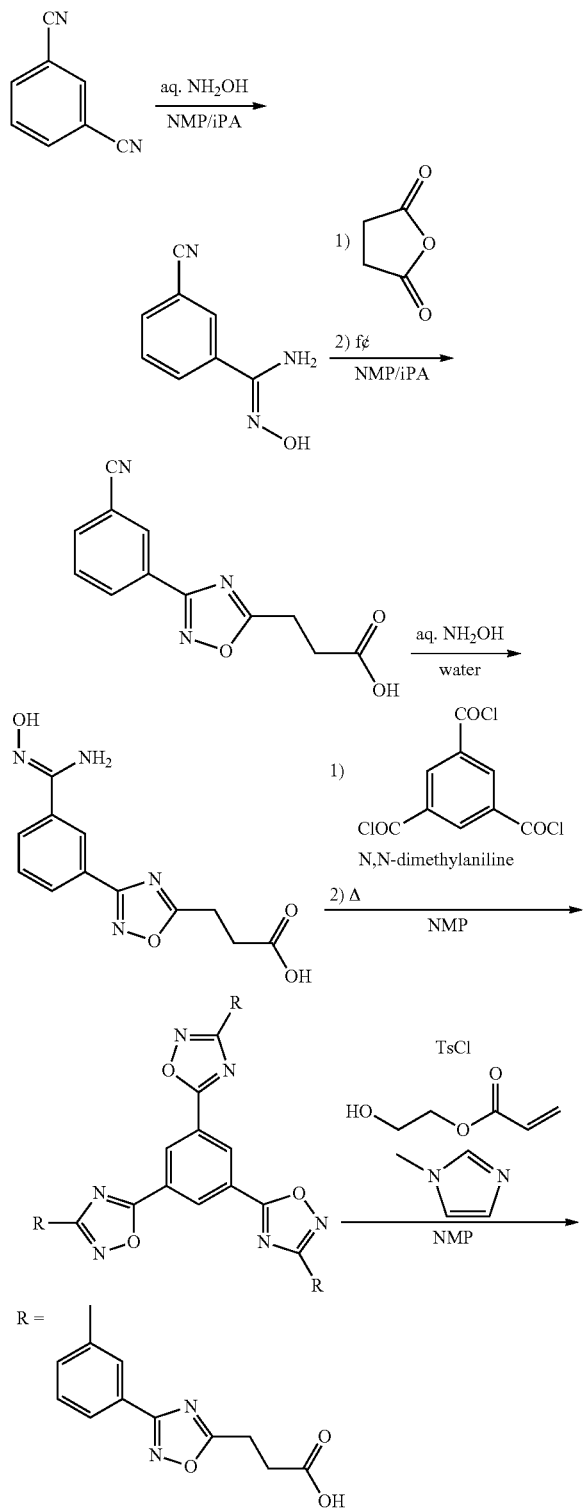

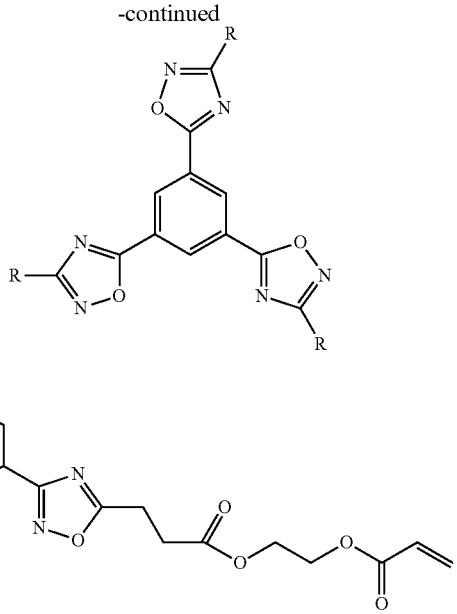

Compound (12)

Isophthalonitrile (5.12 g) was added to NMP (20 mL). The mixture was added dropwise with 50% hydroxylamine (2.64 g) at 40 degrees Celsius. The mixture was stirred at 50 degrees Celsius for four hours to give a solution of a mixture containing a monoamidoxime derivative. The solution was added with succinic acid anhydride (4.41 g) fractionally, and then was stirred under heat at 120 degrees Celsius for five hours. After being cooled, the resultant was added with 50 mL of ethyl acetate, was washed with 1 N HCl, and was extracted inversely with a saturated sodium bicarbonate water to give an aqueous solution of a mixture containing an oxadiazole derivative. The solution was added dropwise with 50% hydroxylamine (4.84 g) at 40 degrees Celsius, and then stirred at 50 degrees Celsius for four hours. After being cooled, the resultant was neutralized with 1N HCl to give a precipitation via filtration. The precipitation was washed with water to give about 7.3 g of a solid mixture containing an amidoxime derivative.

The solid mixture (7.3 g) containing the amidoxime derivative was added with NMP (20 mL) and trimesic acid chloride (1.3 g), and was added with N,N-diemthylaniline (4.1 mL) while being cooled with ices. After that, the reaction solution was stirred at the room temperature for an hour, and was further stirred at 100 degrees Celsius for two hours. After being cooled, crystallized with 1N HCl and purified according to column chromatography, 4 g of a tricarboxylic acid derivative was obtained.

The tricarboxylic acid derivative (4 g) was added with NMP (20 mL), 2-hydroxy ethyl acrylate (1.8 mL), and tosyl acid chloride (3.3 g), and was added dropwise with N-methyl imidazole (2.8 mL) while being cooled. After being stirred at the room temperature for two hours, the resultant was poured into methanol (200 mL), thereby giving a precipitation. The precipitation was obtained via filtration, and then was washed with methanol. The resultant was purified according to column chromatography to give 3.2 g (61% yield constant) of a target compound, that is, Compound (12). The identification of the compound was carried out by $^1$H-NMR.

$^1$H-NMR (CDCl$_3$) δ: 3.04 (6H, t), 3.33 (6H, t), 4.35~4.50 (12H, m), 5.82 (3H, d), 6.12 (3H, dd), 6.47 (3H, d), 7.70 (3H, t), 8.27 (3H, d), 8.43 (3H, d), 8.93 (3H, s), 9.30 (3H, s).

The phase transition temperature of the obtained Compound (12) was studied by texture observation of the compound with polarization microscope. Raising the temperature to around 74 degrees Celsius, the phase was changed from the crystal phase to the discotic nematic phase; and further raising the temperature to more than 170 degrees Celsius, the phase was changed to the isotropic liquid phase. That is, from these results, it can be understood that Compound (12) exhibits a discotic nematic phase at a temperature within the range from 74 to 170 degrees Celsius.

Example 14

Synthesis No. 1 of Compound (13)

Compound (13) was prepared in the manner as shown in the following scheme.

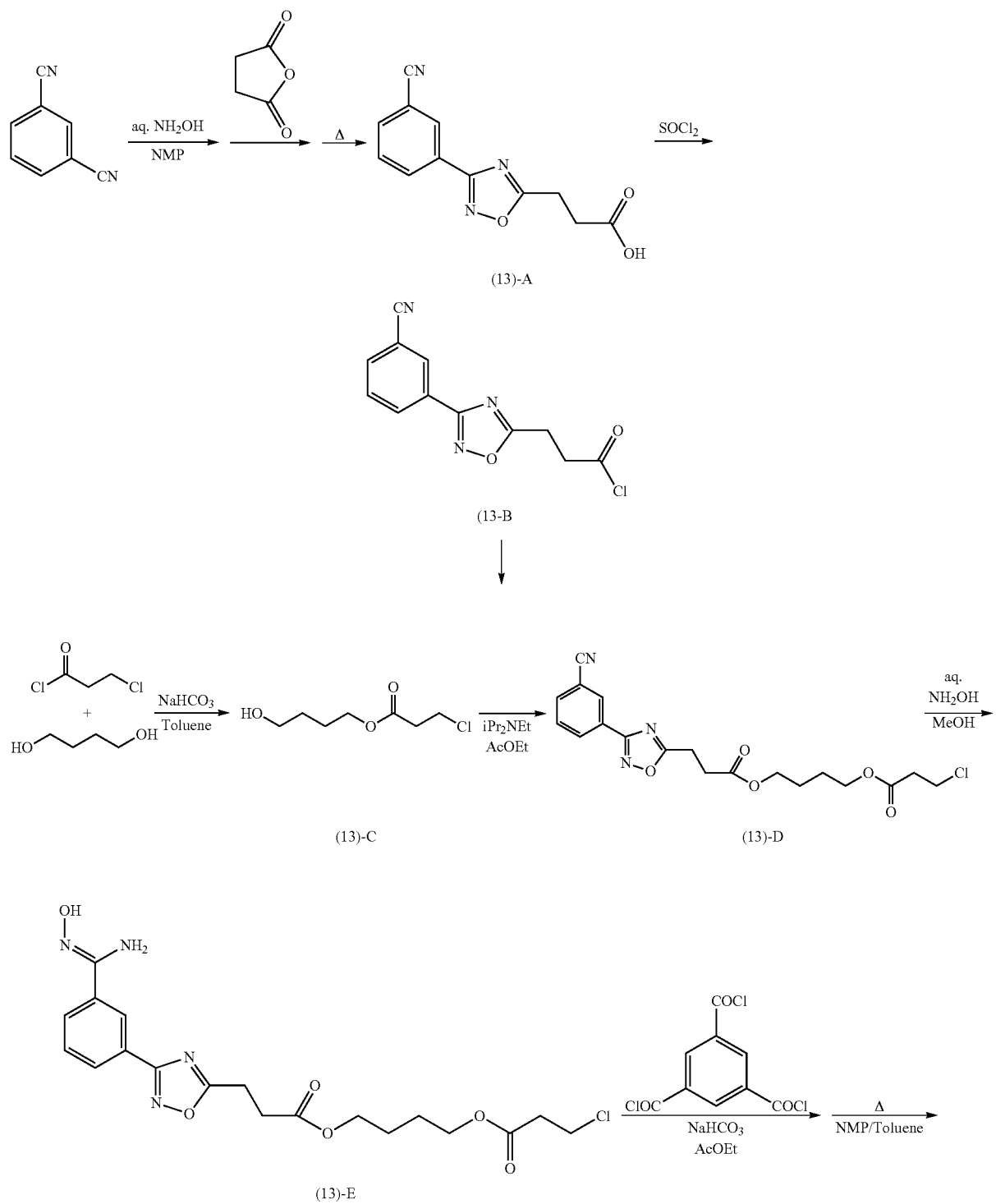

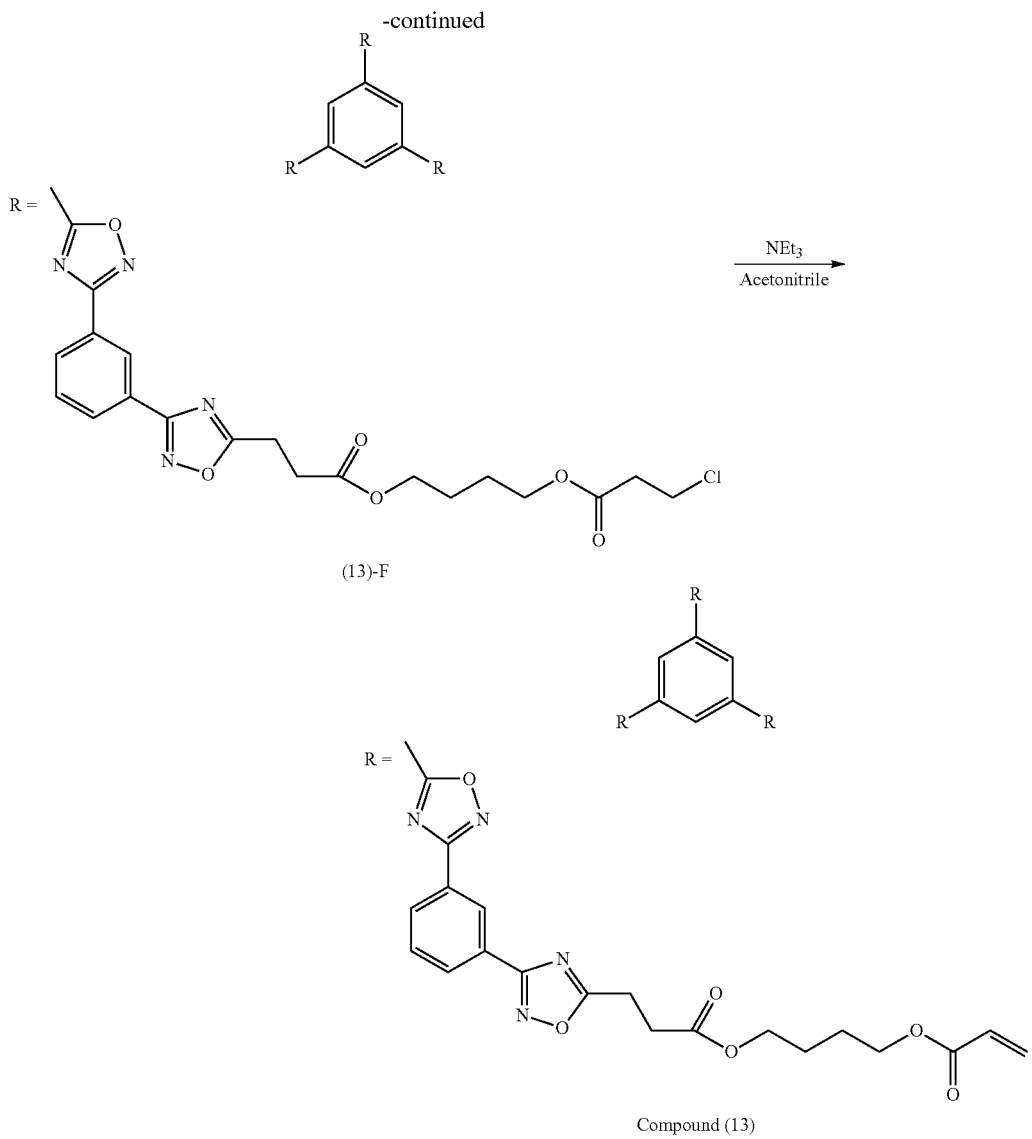

Isophthalonitrile (5.12 g) was added to NMP (20 mL). The mixture was added dropwise with 50% hydroxylamine (2.42 g) at 40 degrees Celsius. After being stirred at 50 degrees Celsius for four hours, the mixture was added with succinic acid anhydride (4.41 g) fractionally, and then was stirred under heat at 120 degrees Celsius for five hours. After being cooled, the resultant was added with 100 mL of ethyl acetate, was washed with water, and was extracted with an aqueous solution of potassium carbonate (5.56 g) to give a water layer. The water layer was neutralized with hydrochloric acid, and was extracted with 100 mL of ethyl acetate. The ethyl acetate layer was washed with water, was dried, and condensed to give about 6.8 g of a solid mixture containing Compound (13)-A.

1,2-butane diol (28.4 g) was added with sodium hydrogen carbonate (12.8 g), and was added dropwise with 3-chloro propionic acid chloride (16.0 g) while being cooled with ices. After being stirred at 25 degrees Celsius for three hours, the resultant was purified according to column chromatography to give about 16.1 g of a mixture containing Compound (13)-C.

The mixture (5.2 g) containing Compound (13)-A was added with toluene (10 mL), DMF (10 mg) and thionyl chloride (2.6 mL), and was stirred for two hours at 50 degrees Celsius. After being cooled, excess thionyl chloride and toluene were distilled away, thereby giving a mixture containing Compound (13)-B. The mixture containing Compound (13)-B was added with ethyl acetate (100 mL) and the mixture (8.4 g) containing Compound (13)-C, and was added dropwise with diisopropyl ethyl amine (5.3 mL). After being stirred at 25 degrees Celsius for an hour, the resultant was washed with dilute hydrochloric acid and saturated salt aqueous solution, was dried, and then was condensed to give a mixture containing Compound (13)-D. The mixture was purified according to column chromatography to give 4.89 g of Compound (13)-D.

Compound (13)-D (4.89 g) was added with methanol (20 mL), and was added dropwise with 50% hydroxylamine (0.95 g) at 40 degrees Celsius. After being stirred for four hours, the resultant was added with 100 mL of ethyl acetate, and was washed with saturated salt aqueous solution to give an ethyl acetate layer. The ethyl acetate layer was purified according to column chromatography to give 4.63 g (88% yield constant) of Compound (13)-E.

Compound (13)-E (4.63 g) was added with ethyl acetate (70 mL) and 70 mL of an aqueous solution of sodium hydrogen carbonate (1.06 g), and was added dropwise with toluene solution (5 mL) of trimesic acid chloride (0.91 g). After being stirred at the room temperature for three hours, the resultant was added with hexane (200 mL), thereby giving a crystal via filtration. The obtained crystal was added with NMP (20 mL) and toluene (20 mL), and was stirred under the azeotropy-dehydrate condition for two hours. After being cooled, toluene was distilled away, and the resultant was added with acetonitrile (20 ml) and triethylamine (3.0 mL), and was stirred at 60 degrees Celsius for two hours. After being cooled, the resultant was added with ethyl acetate (100 mL), was washed with dilute hydrochloric acid and saturated salt aqueous solution, was dried, and then was condensed to give Compound (13) as a crude product. The crude product was purified according to column chromatography to give 3.8 g (85% yield constant) of a target compound, that is, Compound (13). The identification of the compound was carried out by $^1$H-NMR.

$^1$H-NMR (CDCl$_3$) δ: 1.70~1.80 (12H, m), 3.00 (6H, t), 3.32 (6H, t), 4.10~4.20 (12H, m), 5.82 (3H, d), 6.12 (3H, dd), 6.40 (3H, d), 7.68 (3H, t), 8.25 (3H, d), 8.40 (3H, d), 8.93 (3H, s), 9.27 (3H, s).

The phase transition temperature of the obtained Compound (13) was studied by texture observation of the compound with polarization microscope. Raising the temperature to around 70 degrees Celsius, the phase was changed from the crystal phase to the discotic nematic phase; and further raising the temperature to more than 141 degrees Celsius, the phase was changed to the isotropic liquid phase. That is, from these results, it can be understood that Compound (13) exhibits a discotic nematic phase at a temperature within the range from 70 to 141 degrees Celsius.

Example 15

Synthesis No. 2 of Compound (13)

Studying $^1$H-NMR and the phase transition temperatures, it was confirmed that Compound (13) was prepared in the same manner as the synthesis No. 2 of Compound (12) shown in the following scheme.

Example 16

Synthesis of Compound (14)

Compound (14), shown below, was prepared according to the method similar to the above-described method.

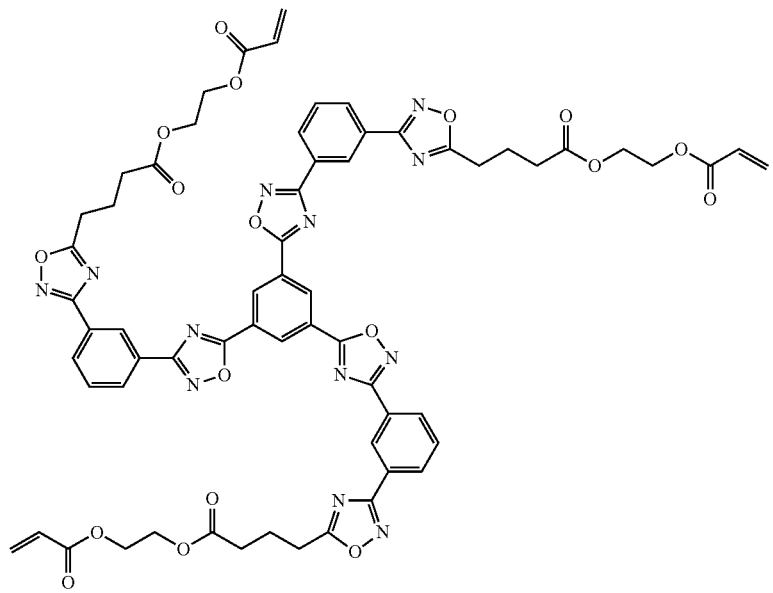

Compound (14)

molecular weight: 1267.17

The identification of the compound was carried out by $^1$H-NMR.

$^1$H-NMR (CDCl$_3$) δ: 2.20~2.35 (6H, m), 2.61 (6H, t), 3.12 (6H, t), 4.30~4.45 (12H, m), 5.82 (3H, d), 6.12 (3H, dd), 6.47 (3H, d), 7.71 (3H, t), 8.25 (3H, d), 8.45 (3H, d), 8.93 (3H, s), 9.27 (3H, s).

The phase transition temperature of the obtained Compound (14) was studied by texture observation of the compound with polarization microscope. Raising the temperature to around 76 degrees Celsius, the phase was changed from the crystal phase to the discotic nematic phase; and further raising the temperature to more than 166 degrees Celsius, the phase was changed to the isotropic liquid phase. That is, from these results, it can be understood that Compound (14) exhibits a discotic nematic phase at a temperature within the range from 76 to 166 degrees Celsius.

Example 17

Synthesis of Compound (15)

Compound (15), shown below, was prepared according to the method similar to the above-described method.

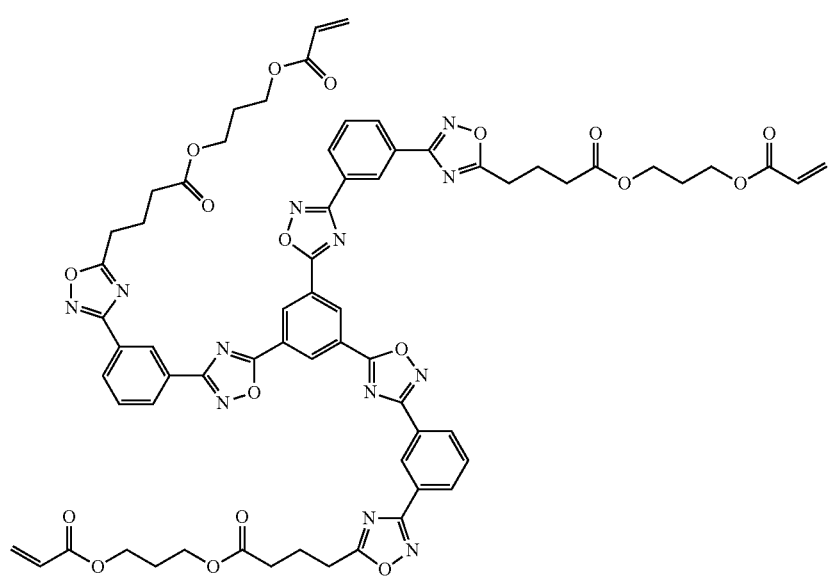

Compound (15)

molecular weight: 1309.25

The identification of the compound was carried out by $^1$H-NMR.

$^1$H-NMR (CDCl$_3$) δ: 1.95~2.10 (6H, m), 2.22~2.35 (6H, m), 2.58 (6H, t), 3.12 (6H, t), 4.20~4.30 (12H, m), 5.85 (3H, d), 6.15 (3H, dd), 6.42 (3H, d), 7.71 (3H, t), 8.30 (3H, d), 8.45 (3H, d), 8.95 (3H, s), 9.30 (3H, s).

The phase transition temperature of the obtained Compound (15) was studied by texture observation of the compound with polarization microscope. Raising the temperature to around 81 degrees Celsius, the phase was changed from the crystal phase to the discotic nematic phase; and further raising the temperature to more than 150 degrees Celsius, the phase was changed to the isotropic liquid phase. That is, from these results, it can be understood that Compound (15) exhibits a discotic nematic phase at a temperature within the range from 81 to 150 degrees Celsius.

Example 18

Synthesis of Compound (16)

Compound (16), shown below, was prepared according to the method similar to the above-described method.

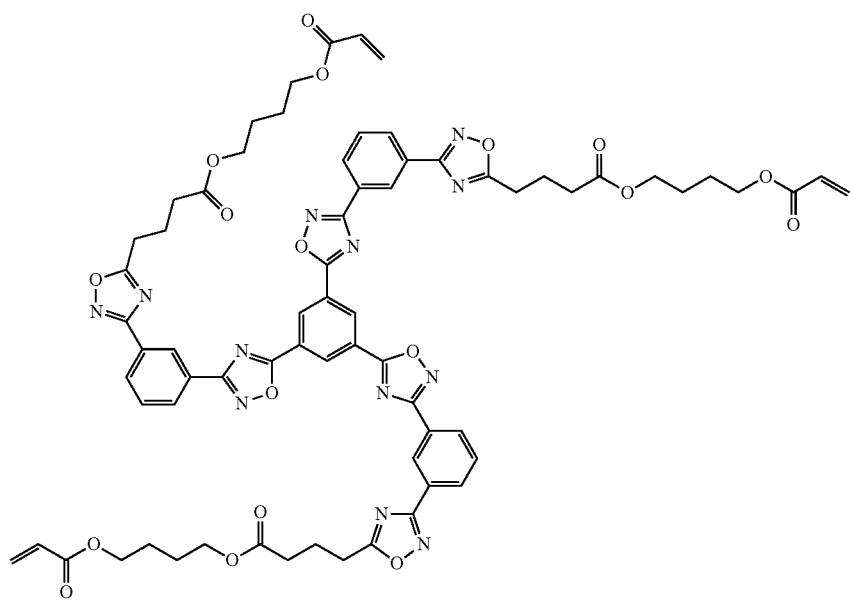

Compound (16)

molecular weight: 1351.33

The identification of the compound was carried out by $^1$H-NMR.

$^1$H-NMR (CDCl$_3$) δ: 1.70~1.85 (12H, m), 2.32~2.45 (6H, m), 2.67 (6H, t), 3.13 (6H, t), 4.15~4.23 (12H, m), 5.80 (3H, d), 6.14 (3H, dd), 6.40 (3H, d), 7.68 (3H, t), 8.25 (3H, d), 8.38 (3H, d), 8.93 (3H, s), 9.27 (3H, s).

The phase transition temperature of the obtained Compound (16) was studied by texture observation of the compound with polarization microscope. Raising the temperature to around 90 degrees Celsius, the phase was changed from the crystal phase to the discotic nematic phase; and further raising the temperature to more than 132 degrees Celsius, the phase was changed to the isotropic liquid phase. That is, from these results, it can be understood that Compound (16) exhibits a discotic nematic phase at a temperature within the range from 90 to 132 degrees Celsius.

Example 19

Preparation of a Film of Uniformly Aligned Compound (13)

An aqueous solution of PVA-1003 (provided by Kuraray) was applied to a surface of a glass substrate, and was dried at 100 degrees Celsius for three minutes to give a PVA-103 film. The thickness of the PVA-103 film was 0.5 micro meters. A coating liquid having the formulation shown below was applied to the surface of the film according to a spin coating method, was left in a constant temperature reservoir of 100 degrees Celsius for a minute, and then was irradiated with 600 mJ ultraviolet light to fix the alignment state. After being cooled down to the room temperature, the alignment state was observed with a polarization microscope, and it was confirmed that the discotic liquid crystal compound was aligned in a homeotropic alignment without any defects. The thickness of the layer was 3.6 micro meters.
(Coating Liquid)

| Compound (13) | 100 parts by mass |
| Agent V-(2) for controlling the alignment at the airt-interface shown below | 0.2 parts by mass |
| Irgacure 907, provided by Ciba-Geigy | 3.0 parts by mass |
| Diethyl thioxanthone | 1.0 parts by mass |
| Methyl ethyl ketone | 250 parts by mass. |

Agent V-(2) for controlling the alignment at the airt-interface

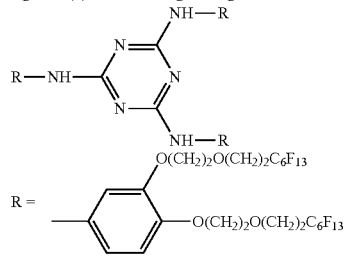

Example 20

Preparation of a Film of Uniformly Aligned Compound (14)

An aqueous solution of PVA-1003 (provided by Kuraray) was applied to a surface of a glass substrate, and was dried at 100 degrees Celsius for three minutes to give a PVA-103 film. The thickness of the PVA-103 film was 0.5 micro meters. A coating liquid having the formulation shown below was applied to the surface of the film according to a spin coating method, was left in a constant temperature reservoir of 100 degrees Celsius for a minute, and then was irradiated with 600 mJ ultraviolet light to fix the alignment state. After being cooled down to the room temperature, the alignment state was observed with a polarization microscope, and it was confirmed that the discotic liquid crystal compound was aligned in a homeotropic alignment without any defects. The thickness of the layer was 3.4 micro meters.
(Coating Liquid)

| Compound (14) | 100 parts by mass |
| Agent V-(2) shown above | 0.2 parts by mass |
| Irgacure 907, provided by Ciba-Geigy | 3.0 parts by mass |
| Diethyl thioxanthone | 1.0 parts by mass |
| Methyl ethyl ketone | 250 parts by mass. |

[Measurement of Δn and Wavelength Dispersion]

The optical properties of each of the obtained films were measured as follows.

In this description, Re(λ) and Rth(λ) are retardation in plane (nm) and retardation along the thickness direction (nm), respectively, at a wavelength of λ.

Re(λ) is measured by applying light having a wavelength of λ nm to a film in the normal direction of the film, using KOBRA (by Oji Scientific Instruments). Rth(λ) is calculated by KOBRA based on three values. One of them is Re(λ), and other two values are measured for incoming light of a wavelength λ nm in two directions which are +40° and −40° with respect to the normal direction of a sample film using an in-plane slow axis, which is decided by KOBRA, as an inclination axis (a rotation axis). In the above-described measurement, the hypothetical value of mean refractive index is available from values listed in catalogues of various optical films in Polymer Handbook (John Wiley & Sons, Inc.). Those having the mean refractive indices unknown can be measured using an Abbe refract meter. Mean refractive indices of some major optical films are listed below:

cellulose acylate (1.48), cycloolefin polymer (1.52), polycarbonate (1.59), polymethylmethacrylate (1.49) and polystyrene (1.59).

The wavelength-dispersion value (Re(478)/Re(748)) of the films of Examples 19 and 20 were calculated by measuring retardation values for the light incoming along the 40°-oblique direction at wavelengths of 478 nm and 748 nm with KOBRA (by Oji Scientific Instruments).

And Δn was calculated by dividing the Rth(589) value of each of the films according to the above-described method with KOBRA (by Oji Scientific Instruments) by the thickness of each of the films. The results are shown in the following table.

| | | Δn | Wavelength dispersion |
|---|---|---|---|
| Example 19 | Liquid Crystal Compound (13) | 0.15 | 1.10 |
| Example 20 | Liquid Crystal Compound (14) | 0.14 | 1.10 |

Hereinafter, some examples of producing an optical compensation film for an OCB-mode liquid crystal display device with the compound of Formula (1) are described in detail.

Example 21

Producing Optical Compensation Film (Preparation of Support)

The composition having the following formulation was poured in a mixing tank, stirred under heating so as to dissolve the individual components, to thereby prepare a cellulose acetate solution.

Formulation of Cellulose Acetate Solution

| | |
|---|---|
| Cellulose acetate having an acetylation degree of 60.9% | 100 parts by mass |
| Triphenyl phosphate (plasticizer) | 7.8 parts by mass |
| Biphenyl diphenyl phosphate (plasticizer) | 3.9 parts by mass |
| Methylene chloride (first solvent) | 300 parts by mass |
| Methanol (second solvent) | 45 parts by mass |
| Dye (360FP provided by SUMICA FINE CHEM) | 0.0009 parts by mass |

In another mixing tank, 16 parts by mass of the retardation increasing agent shown below, 80 parts by mass of methylene chloride and 20 parts by mass of methanol are placed, stirred under heat, to thereby prepare a retardation increasing agent solution.

The cellulose acetate solution in an amount of 464 parts by mass was mixed with 36 parts by mass of the retardation increasing agent solution and 1.1 parts by mass of silica fine particles (R972 provided by AEROGIL), and thoroughly mixed to thereby prepare a dope. The amount of addition of the retardation increasing agent was 5.0 parts by mass weight for 100 parts by weight of cellulose acetate, and the amount of the silica fine particles was 0.15 parts by mass for 100 parts by weight of cellulose acetate.

Retardation increasing agent

Thus obtained dope was cast using a band stretching machine employing a band with a width of 2 m and a length of 65 m. After a film temperature on the band of 40° C. was reached, the film was dried for one minute, and was stretched along the width direction by 28% using a tenter while being applied with dry air of 140 degrees Celsius. The film was further dried with dry air of 135 degrees Celsius for 20 minutes to give a film containing 0.3% by mass of a residual solvent. The film was used as a support (PK-1).

The width of the obtained support (PK-1) was 1340 mm, and the thickness thereof was 92 micro meters. Thus-produced cellulose acetate film was then subjected to measurement of Re retardation value and Rth retardation value at a wavelength of 590 nm, using an ellipsometer (M-150, product of JASCO). Re was 38 nm at a wavelength 590 nm, and Rth was 175 nm at a wavelength 590 nm.

Potassium hydroxy was dissolved in a solvent (water/isopropyl alcohol/propylene glycol=692. parts by mass/15 parts by mass/15.8 parts by mass) to give a 1.0 mol/L solution of potassium hydroxy. The solution was applied to the band-side surface of the support (PK-1) by 10 ml/m$^2$, was left at 40 degrees Celsius for 30 seconds, was wiped off alkali liquid, was washed with water, and was wiped off drops of water by an air-knife. After that, the support was dried at 100 degrees Celsius for 15 seconds. The pure-water contact angle of the PK-1 was 42°.

(Preparation of Alignment Layer)

To a surface of the cellulose acetate film (PK-1), a coating liquid having the formulation below was applied using a #16 wire bar coater in an amount of 28 mL/m$^2$. The obtained layer was dried with a 60° C. air for 60 seconds, and was further dried with a 90° C. air for 150 seconds.

Formulation of Coating Liquid for Alignment Layer

| | |
|---|---|
| Modified polyvinyl alcohol shown below | 10 parts by mass |
| Water | 371 parts by mass |
| Methanol | 119 parts by mass |
| Glutaraldehyde (crosslinking agent) | 0.5 part by mass |
| Citric acid ester (AS3 provided by Sankyo Chemical) | 0.35 parts by mass |

Modified Polyvinyl Alcohol $$-(CH_2-CH)_{96.3}-(CH_3-CH)_2-(CH_3-CH)_{1.7}-$$
$$\quad\quad\quad | \quad\quad\quad\quad\quad | \quad\quad\quad\quad\quad\quad |$$
$$\quad\quad\quad OH \quad\quad\quad O-CO-CH_3 \quad\quad O-CO-NH-CH_2CH_2O-CO-C(CH_3)=CH_2$$

(Rubbing Treatment)

The film (PK-1) was conveyed by a rate of 20 m/min so as to be subjected to a rubbing treatment along the direction of 45° relative to the long direction with a rubbing roll, having a diameter of 300 mm and rotating by a rate of 640 rpm.

(Preparation of Optically Anisotropic Layer)

A coating liquid having the following formulation was continuously applied to the surface of the alignment layer by a #3.0 wire bar rotating by 470 rpm along the conveying direction of the film (PK-1) which was conveyed by a rate of 20 m/min.

(Coating Liquid for Optically Anisotropic Layer)

| | |
|---|---|
| Compound (13) | 100.00 parts by mass |
| Photo-polymerization initiator (Irgacure 907, provided by Ciba-Geigy) | 3.0 parts by mass |
| Sensitizer (Kayacure DETX, provided by Nippon Kayaku) | 1.00 parts by mass |
| Fluoroaliphatic group-containing copolymer (Megafac F780, provided by Dainippon Ink and Chemicals) | 0.40 parts by mass |
| Methyl ethyl ketone | 500.00 parts by mass |

The coated layer was continuously heated from the room temperature to 100 degrees Celsius while the solvent was evaporated, and was heated at 100 degrees Celsius for about 90 seconds, so that the discotic liquid crystal molecules were aligned. Next, the film was conveyed into the heat zone at 80 degrees Celsius, and was irradiated with 600 mW-UV light for four seconds using a 160 W/cm high pressure mercury lamp having an emission length of 1.6 m, when the temperature of the layer plane was 90 degrees Celsius; and reaction of the discotic molecules was carried out, thereby that the molecules were fixed in the alignment state. After that, the film was cooled down to the room temperature, and then was wound up in a roll form. In this way, a wound-up optical compensation film (KH-1) was produced.

A part of the obtained wound-up optical compensation film (KH-1) was cut off, and was used as a sample for measurement of Re at a wavelength of 546 nm. And Re at 546 nm of the sample was 30 nm. Studying the mean direction of molecular symmetrical axes of the optically anisotropic layer, it was the direction of 45° with respect to the long direction of the optical compensation film (KH-1).

Furthermore, unevenness of the obtained optical compensation film was observed using Cross-Nicol polarizers. As a result, any unevenness was not observed in the normal direction and the oblique direction of 60° relative to the normal direction.

Example 22

An optical compensation film (KH-2) was produced in the same manner as Examples 21, except that a coating liquid having the following formulation was used in place of the above-described coating liquid.
(Coating Liquid for Optically Anisotropic Layer)

| | |
|---|---|
| Compound (14) | 100.00 parts by mass |
| Photo-polymerization initiator (Irgacure 907, provided by Ciba-Geigy) | 3.00 parts by mass |
| Sensitizer (Kayacure DETX, provided by Nippon Kayaku) | 1.00 parts by mass |
| Fluoroaliphatic group-containing copolymer (Megafac F780, provided by Dainippon Ink and Chemicals) | 0.40 parts by mass |
| Methyl ethyl ketone | 500.00 parts by mass |

A part of the obtained wound-up optical compensation film (KH-2) was cut off, and was used as a sample for measurement of Re at a wavelength of 546 nm. And Re at 546 nm of the sample was 29 nm. Studying the mean direction of molecular symmetrical axes of the optically anisotropic layer, it was the direction of 45° with respect to the long direction of the optical compensation film (KH-2).

Furthermore, unevenness of the obtained optical compensation film was observed using Cross-Nicol polarizers. As a result, any unevenness was not observed in the normal direction and the oblique direction of 60° relative to the normal direction.

Example 23

Production of Polarizing Plate

A PVA film (a thickness of 80 micro meters and a width of 2500 mm) of PVA (a mean degree of polymerization of 1700 and a degree of saponification of 99.5 mol %) was stretched eightfold monoaxially in the longitudinal direction, and subsequently was immersed in an aqueous solution containing 0.2 g/L of iodine and 60 g/L of potassium iodide at 30° C. for five minutes, and then in an aqueous solution containing 100 g/L of boric acid and 30 g/L potassium iodide. At the time, the width of the film was 1300 mm and the thickness was 17 micro meters.

After that, the PVA film was immersed in a water bath at 20 degrees Celsius for 10 seconds, and then was immersed in an aqueous solution containing 0.1 g/L of iodine and 20 g/L of potassium iodide at 30° C. for 15 seconds, and dried at the room temperature for 24 hours, to thereby obtain an iodine-base polarizing film (HF-1).

The surface of the support (PK-1) of the optical compensation film (KH-1), which was prepared in Example 21, was adhered to one surface of the polarizing film (HF-1) using a polyvinyl alcohol base adhesive, so that the optical compensation film (KH-1) was combined with the polarizing film (HF-1). An 80-µm-thick cellulose triacetate film (TD-80U, product of FujiFilm) was saponified, and the surface of the saponified film was adhered to another surface of the polarizing film using a polyvinyl alcohol base adhesive.

The three films were combined so that the long directions of the polarizing film, the support (PK-1) and the commercially available triacetyl cellulose film were parallel to each other. In this way, a polarizing plate was produced, and was used as Polarizing plate (HB-1BR).

And the surface of the support (PK-1) of the optical compensation film (KH-1), which was prepared in Example 21, was adhered to one surface of the polarizing film (HF-1) using a polyvinyl alcohol base adhesive, so that the optical compensation film (KH-1) was combined with the polarizing film (HF-1). A film with an antireflective layer (CV-UA, product of FujiFilm) was saponified, and the surface of the saponified film was adhered to another surface of the polarizing film using a polyvinyl alcohol base adhesive.

The three films were combined so that the long directions of the polarizing film, the support (PK-1) and the commercially available film with an antireflective layer were parallel to each other. In this way, a polarizing plate was produced, and was used as Polarizing plate (HB-1BF).

Example 24

Production of Polarizing Plate

Two polarizing plates (HB-2BR and HB-2BF) were produced in the same manner as Example 23 respectively, except that the optical compensation film (KH-2), which was prepared in Example 22, was used in place of the optical compensation film (KH-1).

Example 25

Production of Bend Alignment Mode Liquid Crystal Cell

An alignment layer of polyimide was formed on a glass plate with an ITO electrode, and then was subjected to a rubbing treatment. In this way, two glass substrates were prepared. The substrates were disposed facing each other, so that the rubbing directions thereof were parallel to each other; and the cell-gap between them was 4.5 micro meters. The cell-gap was filled with liquid crystal ("ZLI1132", by Merck), having Δn of 0.1396 to give a 5-inch bend-alignment mode liquid crystal cell.

The polarizing plates (HB-1BF) and (HB-1BR) which were prepared in Example 23 were adhered to the observer side surface and the backlight side surface of the obtained bend-alignment cell respectively. The optically anisotropic layer was disposed inside, that is, faced the cell substrate; and the rubbing direction of the cell substrate was anti-parallel to the rubbing direction of the optically anisotropic layer, which was facing the cell substrate, of the elliptical polarizing plate.

A 55-Hz square-wave pulse voltage was applied to the liquid crystal cell. The cell, employing a normally-white mode, was applied with 2V in the white state and with 5V in the black state. The contrast was calculated as the ratio of the light-transmittance in the white to the light-transmittance in the black state (white state/black state). The viewing angles of 8 stages from the black state (L1) to the white state (L8) were measured using a measuring machine (EZ-Contrast160D, provided by ELDIM). The angle-dependent properties of the displaying color were subjected to visual evaluation. And the contrast in the normal direction (CR: the ratio of brightness in the white state to brightness in the black state) was also measured. The results were shown in the following table.

Example 26

A liquid crystal panel was produced in the same manner as Example 25, except that the polarizing plates HB-2BF and HB-2BR were used as the polarizing plate at the observer side and the backlight side respectively; and was evaluated in the same manner as Example 25.

TABLE 4

| Polarizing Plate used with Bend Alignment Cell | Viewing Angle* | | | CR in the normal direction Upper side |
|---|---|---|---|---|
| | Upper side | Lower side | Right Left | |
| Example 25 | 80 | 80 | 80 | 500 |
| Example 26 | 80 | 80 | 80 | 500 |

*Viewing angle achieving a contrast ratio equal to or more than 10 without gray scale inversion (inversion generating between L1 and L2)

From the results shown in the table, it can be understood that the OCB mode liquid crystal display device having the optically anisotropic layer, which was prepared using Compound (13) or (14), showed the good displaying characteristics.

Next, some examples of the retardation plate for TN-mode having the optical film which was prepared using the compound of formula (1) are described in detail.

Example 27

Preparation of Transparent Support

The composition having the following formulation was poured in a mixing tank, stirred under heating so as to dissolve the individual components, to thereby prepare a cellulose acetate solution (hereinafter, referred to as "dope").

Formulation of Cellulose Acetate Solution

| | |
|---|---|
| Cellulose acetate having an acetylation degree of 60.9% | 100 parts by mass |
| Triphenyl phosphate (plasticizer) | 6.5 parts by mass |
| Biphenyl diphenyl phosphate (plasticizer) | 5.2 parts by mass |
| Retardation increasing agent (1) shown below | 0.1 parts by mass |
| Retardation increasing agent (2) shown below | 0.2 parts by mass |

-continued

| | |
|---|---|
| Methylene chloride (first solvent) | 310.25 parts by mass |
| Methanol (second solvent) | 54.75 parts by mass |
| 1-butanol | 10.95 parts by mass |

Retardation increasing agent (1)

Retardation increasing agent (2)

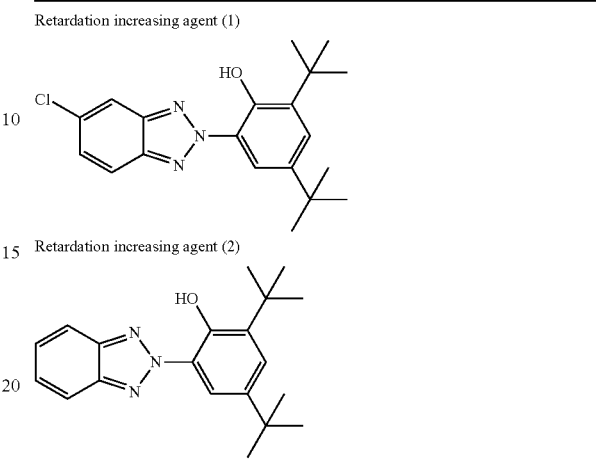

The dope was cast on a drum as cooled at 0° C. from a casting nozzle. The film was stripped off in the state that a solvent content was 70% by weight, and the both ends in the width direction of the film were fixed by a pin tenter and dried while keeping a gap such that the stretching ratio in the transversal direction (the vertical direction to the machine direction) became from 3% in the state of a solvent content of from 3 to 5% by weight. Thereafter, the resulting film was further dried by delivering it between rolls of a heat treatment device. The stretching ratio of the film was adjusted substantially to 0% in the area at a temperature more than 120 degrees Celsius (this was because the film was subjected to a stretching with a stretching ratio of 4% in the machine direction when being peeled off); and the ratio of the stretching ratio in the transversal direction to the stretching ratio in the machine direction was adjusted to 0.75. In this way, a cellulose acetate film having a thickness of 100 micro meters was prepared. The retardation value of the obtained film at a wavelength of 632.8 nm was measured, and it was found that retardation along the thickness direction was 40 nm; and retardation in plane was 4 nm. The cellulose acylate film was used as a support.

(Preparation of First Undercoat Layer)

A coating liquid having the following formulation was applied to a surface of the obtained support by 28 mL/m², and was dried to form a first undercoat layer.

(Formulation of Coating Liquid for First Undercoat Layer)

| | |
|---|---|
| Gelatin | 5.44 parts by mass |
| Formaldehyde | 1.38 parts by mass |
| salicylic acid | 1.62 parts by mass |
| Acetone | 391 parts by mass |
| Methanol | 158 parts by mass |
| Methylene chloride | 406 parts by mass |
| Water | 12 parts by mass |

(Formulation of Coating Liquid for Second Undercoat Layer)

A coating liquid having the following formulation was applied to a surface of the prepared first undercoat by 7 mL/m², and was dried to form a second undercoat layer.

99

(Formulation of Coating Liquid for Second Undercoat Layer)

| Anionic Polymer shown below | 0.77 parts by mass |
|---|---|
| Citric acid mono ester | 10.1 parts by mass |
| Acetone | 200 parts by mass |
| Methanol | 877 parts by mass |
| Water | 40.5 parts by mass |

Anionic Polymer

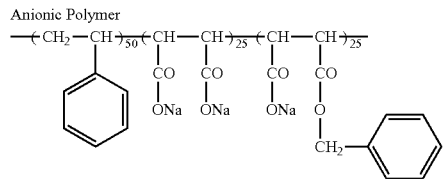

(Preparation of Back Layer)

A coating liquid having the following formulation was applied to another surface of the prepared first undercoat by 25 mL/m², and was dried to form a back layer.
(Formulation of Coating Liquid for Back Layer)

| Cellulose acetate having an acetylation degree of 55% | 6.56 parts by mass |
|---|---|
| Silica Matting Agent (mean particle size of 1 micro meter) | 0.65 parts by mass |
| Acetone | 679 parts by mass |
| Methanol | 104 parts by mass |

(Preparation of Alignment Layer)

A 5% by mass solution was prepared by dissolving a modified polyvinyl alcohol shown below and glutaraldehyde (5% by mass with respect to the mass of the modified polyvinyl alcohol) in a mixed solvent of methanol and water (methanol/water=20/80 volume ratio)

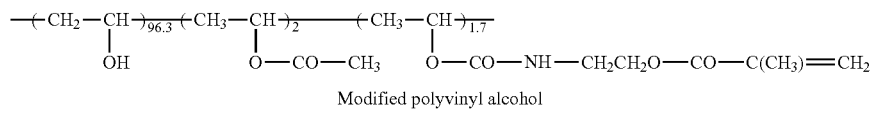

Modified polyvinyl alcohol

To a surface of the second undercoat layer, the solution was applied, was dried at 100 degrees Celsius for 120 seconds, and was subjected to a rubbing treatment, to give an alignment layer. The thickness of the alignment layer was 0.5 micro meters. The rubbing direction was parallel to the casting direction of the support.

(Preparation of Optically Anisotropic Layer)

A coating liquid having the following formulation was continuously applied to the rubbed surface of the alignment layer by a wire bar.

(Coating Liquid for Optically Anisotropic Layer)

| Compound (13) | 100 parts by mass |
|---|---|
| Photo-polymerization initiator (Irgacure 907, provided by Ciba-Geigy) | 2.0 parts by mass |

100

| Agent for controlling alignment at the air-interface (KK-1) shown below | 0.1 parts by mass |
|---|---|
| Chloroform | 270 parts by mass |

Agent for controlling alignment at the air-interface (KK-1)

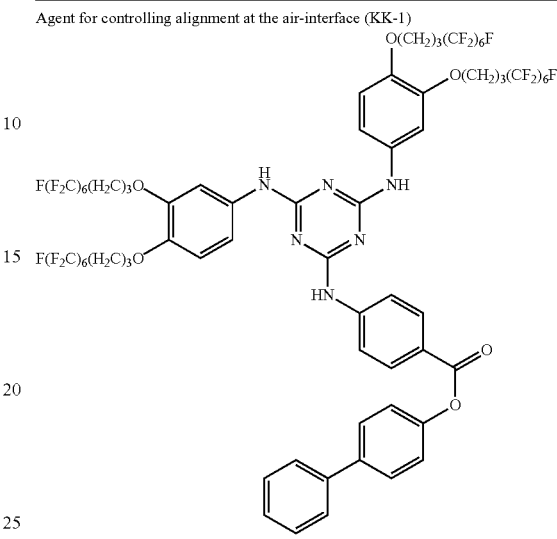

The film having the coated layer was left in a constant-temperature bath of 100 degrees Celsius, so that the liquid crystal molecules were aligned. Then, the coated layer was irradiated with UV light of 200 mJ/cm² to be fixed in the alignment state, and was cooled down to the room temperature. In this way, an optical compensation film was prepared, and used as optical compensation film (KI-1). The thickness of the optically anisotropic layer was 0.65 micro meters.

Example 28

An optical compensation film (kI-2) was prepared in the same manner as Example 27, except that a coating liquid having the following formulation was used for preparing an optically anisotropic layer. The thickness of the layer was 0.66 micro meters.

(Coating Liquid for Optically Anisotropic Layer)

| Compound (14) | 100 parts by mass |
|---|---|
| Photo-polymerization initiator (Irgacure 907, provided by Ciba-Geigy) | 2.0 parts by mass |
| Agent for controlling alignment at the air-interface (KK-1) shown above | 0.1 parts by mass |
| Chloroform | 270 parts by mass |

[Evaluation of Optical Compensation Films]

The optical properties of each of the optical compensation films were measured in the manner as described above.

Re and Rth were measured at a wavelength of 589 nm.

The wavelength dispersion indicates the value of Re(478 nm)/Re(748 nm).

The obtained data were shown in the following table.

An ultra-thin layer of the optically anisotropic layer of each of the films, which was prepared in Examples 27 and 28, was prepared as a sample using a microtome; and the section of the sample was observed using a polarization microscope. And it was found that liquid crystal molecules in the layer were fixed in the hybrid alignment.

(Production of Liquid Crystal Display Device)

An alignment layer of polyimide was formed on a glass plate with an ITO electrode, and then was subjected to a rubbing treatment. In this way, two glass substrates were prepared. The substrates were disposed facing each other, so that the rubbing directions thereof were perpendicular to each other; and the cell-gap between them was 5 micro meters. The cell-gap was filled with rod-like liquid crystal ("ZL4792", by Merck), having Δn of 0.0969 to give a TN-mode liquid crystal cell.

Each of the prepared TN-mode liquid crystal display devices was applied with 2V in the white state and with 5V in the black state. The contrast was calculated as the ratio of the light-transmittance in the white to the light-transmittance in the black state (white state/black state). The viewing angle was determined as an area achieving a contrast equal to or higher than 10 in the vertical direction (up-down) and in the horizontal direction (right-left) without any gray scale inversion. And the angle-dependent properties of the displaying color were subjected to visual evaluation. The results were shown in the table below.

TABLE 5

| | | | | Viewing Angle | | |
| --- | --- | --- | --- | --- | --- | --- |
| | Wavelength Dispersion | Re | Rth | Vertical direction (up-down) | Horizontal direction (right-left) | Variation in color |
| Example 27 | 1.10 | 33 nm | 156 nm | 95° | 147° | Not recognized |
| Example 28 | 1.10 | 33 nm | 156 nm | 95° | 147° | Not recognized |

From the results shown in the table, it can be understood that the TN mode liquid crystal display device having the optically anisotropic layer, which was prepared using Compound (13) or (14), showed the good displaying characteristics.

What is claimed is:

1. A compound represented by formula (1a):

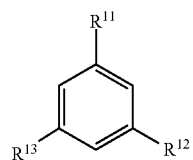

where $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C):

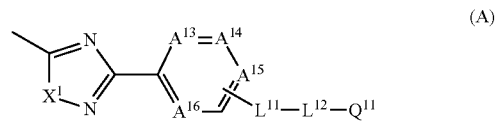

where $A^{13}$, $A^{14}$, $A^{15}$ and $A^{16}$ each independently represent methine, provided that any hydrogen atom(s) in methine may be replaced with a group, $-L^{11}-L^{12}-Q^{11}$; $X^1$ represents an oxygen atom, a sulfur atom, methylene or imino; $L^{11}$ represents a 5-membered heterocyclic group; $L^{12}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{11}$ represents a polymerizable group, a hydrogen atom, OH, COOH or a halogen atom;

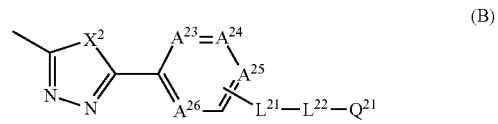

where $A^{23}$, $A^{24}$, $A^{25}$ and $A^{26}$ each independently represent methine, provided that any hydrogen atom(s) in methine may be replaced with a group, $-L^{21}-L^{22}-Q^{21}$; $X^2$ represents an oxygen atom, a sulfur atom, methylene or imino; $L^{21}$ represents a 5-membered heterocyclic group; $L^{22}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{21}$ represents a polymerizable group, OH, COOH or a halogen atom;

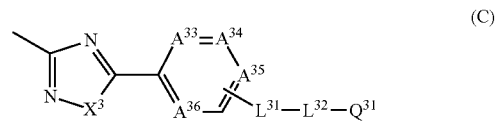

where $A^{33}$, $A^{34}$, $A^{35}$ and $A^{36}$ each independently represent a nitrogen atom or methine, provided that any hydrogen atom(s) in methine may be replaced with a group, $-L^{31}-L^{32}-Q^{31}$; $X^3$ represents an oxygen atom, a sulfur atom, methylene or imino; $L^{31}$ represents a 5-membered heterocyclic group; $L^{32}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{31}$ represents a polymerizable group, a hydrogen atom, OH, COOH or a halogen atom.

2. The compound according to claim 1, wherein the $L^{11}$ in formula (A), $L^{21}$ in formula (B) and $L^{31}$ in formula (C) each independently represent DA any one of the following formulae;

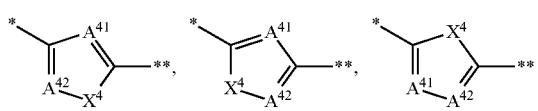

in the formulae, "*" indicates a site binding to the 6-membered ring; "**" indicates a site binding to $L^{12}$, $L^{22}$ or $L^{32}$; A41 and $A^{42}$ each independently represent a nitrogen atom or methine; and $X^4$ represents an oxygen atom, a sulfur atom, methylene or imino.

3. The compound according to claim 1, wherein the polymerizable group is represented by the following formula;

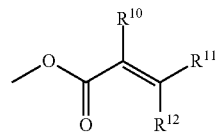

in the formula, $R^{10}$, $R^{11}$ and $R^{12}$ each independently represent a hydrogen atom or an alkyl.

4. A compound represented by formula (1a):

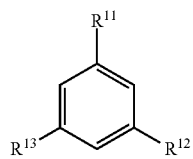

(1a)

where $R^{11}$, $R^{12}$ and $R^{13}$ each independently represent formula (A), (B) or (C) or a hydrogen atom, provided that at least two of $R^{11}$, $R^{12}$ and $R^{13}$ each independently represent formula (A), (B) or (C):

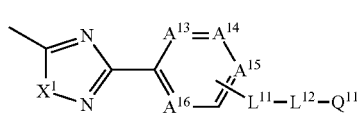

(A)

where $A^{13}$, $A^{14}$, $A^{15}$ and $A^{16}$ each independently represent methine, provided that any hydrogen atom(s) in methine may be replaced with a group, -$L^{11}$-$L^{12}$-$Q^{11}$; $X^1$ represents an oxygen atom, a sulfur atom, methylene or imino; $L^{11}$ represents a 5-membered heterocyclic group; $L^{12}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{11}$ represents a polymerizable group, a hydrogen atom, OH, COOH or a halogen atom;

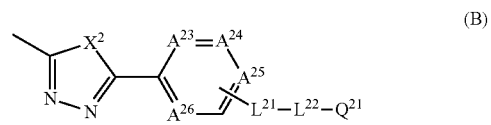

(B)

where $A^{23}$, $A^{24}$, $A^{25}$ and $A^{26}$ each independently represent methine, provided that any hydrogen atom(s) in methine may be replaced with a group, -$L^{21}$-$L^{22}$-$Q^{21}$; $X^2$ represents an oxygen atom, a sulfur atom, methylene or imino; $L^{21}$ represents a 5-membered heterocyclic group; $L^{22}$ represents an alkylene or alkenylene, provided that one $CH_2$ or two or more $CH_2$ not adjacent to each other in the alkylene or alkenylene may be independently replaced with at least one selected from the group consisting of —O—, —COO—, —OCO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{21}$ represents a polymerizable group, a hydrogen atom, OH, COOH or a halogen atom;

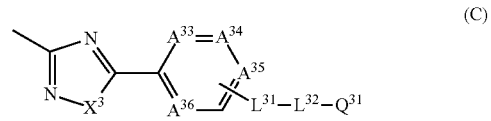

(C)

where $A^{33}$, $A^{34}$, $A^{35}$ and $A^{36}$ each independently represent a nitrogen atom or methine, provided that any hydrogen atom(s) in methine may be replaced with a group, -$L^{31}$-$L^{32}$-$Q^{31}$; $X^3$ represents an oxygen atom, a sulfur atom, methylene or imino; $L^{31}$ represents a 5-membered heterocyclic group; $L^{32}$ represents an alkylene or alkenylene, provided that one $CH_2$ or two or more $CH_2$ not adjacent to each other in the alkylene or alkenylene may be independently replaced with at least one selected from the group consisting of —O—, —COO—, —COO—, —OCOO—, —CO—, —S—, —$SO_2$—, —NR—, —$NRSO_2$— and —$SO_2NR$— where R represents a hydrogen atom or a $C_{1-4}$ alkyl, or provided that one hydrogen atom or two or more hydrogen atoms in the alkylene or the alkenylene may be replaced with one halogen atom or two or more halogen atoms; and $Q^{31}$ represents a polymerizable group, a hydrogen atom, OH, COOH or a halogen atom, wherein the $L^{11}$ in formula (A), $L^{21}$ in formula (B) and $L^{31}$ in formula (C) each independently represent any one of the following formulae;

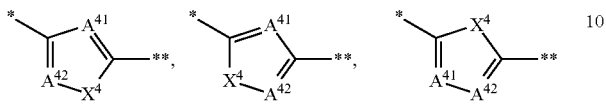

in the formulae, "*" indicates a site binding to the 6-membered ring; "**" indicates a site binding to $L^{12}$, $L^{22}$ or $L^{32}$; $A^{41}$ and $A^{42}$ each independently represent a nitrogen atom or methine; and $X^4$ represents an oxygen atom, a sulfur atom, methylene or imino.

* * * * *